(12) United States Patent
Zlotnick et al.

(10) Patent No.: US 10,006,913 B2
(45) Date of Patent: Jun. 26, 2018

(54) FLUORESCENT-HAP: A DIAGNOSTIC STAIN FOR HBV CORES IN CELLS

(71) Applicant: INDIANA UNIVERSITY RESEARCH AND TECHNOLOGY CORPORATION, Ndianapolis, IN (US)

(72) Inventors: Adam Zlotnick, Bloomington, IN (US); Lichun Li, Bloomington, IN (US); Michael S. Van Nieuwenhze, Bloomington, IN (US); William W. Turner, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 308 days.

(21) Appl. No.: 14/777,636

(22) PCT Filed: Mar. 20, 2014

(86) PCT No.: PCT/US2014/031326
§ 371 (c)(1),
(2) Date: Sep. 16, 2015

(87) PCT Pub. No.: WO2014/153459
PCT Pub. Date: Sep. 25, 2014

(65) Prior Publication Data
US 2016/0274112 A1   Sep. 22, 2016

Related U.S. Application Data

(60) Provisional application No. 61/803,554, filed on Mar. 20, 2013.

(51) Int. Cl.
| | | |
|---|---|---|
| *A61B 5/00* | (2006.01) |
| *A61B 8/00* | (2006.01) |
| *A61B 10/00* | (2006.01) |
| *G01N 33/569* | (2006.01) |
| *C09B 11/08* | (2006.01) |
| *C09B 11/24* | (2006.01) |
| *C09B 23/02* | (2006.01) |
| *C09B 57/00* | (2006.01) |
| *C09B 57/02* | (2006.01) |
| *C09B 57/10* | (2006.01) |
| *C12Q 1/18* | (2006.01) |
| *A61K 49/00* | (2006.01) |

(52) U.S. Cl.
CPC ........ *G01N 33/56983* (2013.01); *C09B 11/08* (2013.01); *C09B 11/24* (2013.01); *C09B 23/02* (2013.01); *C09B 57/00* (2013.01); *C09B 57/02* (2013.01); *C09B 57/10* (2013.01); *C12Q 1/18* (2013.01); *A61K 49/0017* (2013.01); *G01N 2333/02* (2013.01); *G01N 2500/02* (2013.01); *G01N 2500/04* (2013.01); *G01N 2500/10* (2013.01)

(58) Field of Classification Search
None
See application file for complete search history.

(56) References Cited

U.S. PATENT DOCUMENTS

2012/0149695 A1*  6/2012  Li ................. A61K 31/505
514/227.8

\* cited by examiner

*Primary Examiner* — Michael G Hartley
*Assistant Examiner* — Melissa J Perreira
(74) *Attorney, Agent, or Firm* — Faegre Baker Daniels LLP

(57) ABSTRACT

Heteroaryldihydropyrimidine (HAP)-based fluorescent stains (compounds), as well as uses of such stains as diagnostic reagents, viral-tracking agents, and/or tools for drug discovery are described. The present invention relates to heteroaryldihydropyrimidine (HAP)-based fluorescent stains (compounds), as well as uses of such stains as diagnostic reagents, viral-tracking agents, and/or tools for drug discovery.

28 Claims, 4 Drawing Sheets

FLUORESCENT-HAP: A DIAGNOSTIC STAIN FOR HBV CORES IN CELLS

CROSS-REFERENCE TO RELATED APPLICATIONS

This application is a US National Phase filing of PCT/U.S. Ser. No. 14/031,326, filed on Mar. 20, 2014, which claims benefit of U.S. 61/803,554 filed on Mar. 20, 2013. The disclosure of which is expressly incorporated entirely by reference.

GOVERNMENT SUPPORT CLAUSE

This invention was made with government support under AI067417 awarded by the National Institutes of Health. The Government has certain rights in the invention.

TECHNICAL FIELD

The present invention relates to heteroaryldihydropyrimidine (HAP)-based fluorescent stains (compounds), as well as uses of such stains as diagnostic reagents, viral-tracking agents, and/or tools for drug discovery.

BACKGROUND

Hepatitis B Virus (HBV) is endemic worldwide: 2 billion people have been infected with HBV and approximately 400 million people suffer from chronic HBV (1). This year, about 600,000 people will die of HBV-related hepatocellular carcinoma, cirrhosis, and liver failure. The United States alone is home to about 2 million individuals with chronic HBV.

HBV is an enveloped virus with an icoshedral core. The core is assembled in the cytoplasm from core (capsid) protein, viral pregenomic RNA, viral reverse transcriptase, and several host proteins (C. Bourne, et al., 2008, J. Virol., 82:10262-10270). HBV has four open reading frames in its 3200-base pair genome one of which encodes the core protein (HBcAg or Cp), a 183-residue protein 240 copies of which self-assemble as homodimers into a roughly spherical capsid (Bourne, et al., 2008). When packaged with the viral genome and appropriate accessory proteins, the entire complex is referred to as the viral core which plays indispensable roles in viral DNA synthesis (from the pregenome) and intracellular trafficking (Ganem, D., and R. J. Schneider, 2001, Hepadnaviridae: the viruses and their replication, 4th ed. Lippincott Williams & Wilkins, Philadelphia, Pa.). An alternative start codon for the core gene results in expression of the e-antigen, which is identical to core protein except for having an N-terminal extension, a C-terminal truncation, and being secreted into serum as a dimer.

Chronic HBV may vary in its symptoms and its need for treatment. The predominant antiviral treatment strategy against HBV has thus far been to attack viral reverse transcriptase. Not surprisingly, HBV reverse transcriptase inhibitors lead to drug-resistant mutants in HBV (Deres, K., and H. Rubsamen-Waigmann, 1999, Infection 27(Suppl. 2):S45-S51; Tennant, B. C., et al., 1998, Hepatology 28:179-191; Zhang, et al., 2003, J. Med. Virol. 71:24-30) and also in human immunodeficiency virus (Lewis-Hall, F. C, 2007, Re: Important information regarding BARACLUDE (entecavir) in patients co-infected with HIV and HBV. Food and Drug Administration MedWatch Program. Food and Drug Administration, Washington, D.C.). Resistance can have broader consequences because of the extensive gene overlap in HBV, since some reverse transcriptase mutations lead to surface protein that is insensitive to antibodies generated by the HBV vaccine (Torresi, J., et al., 2002, Virology 293: 305-313). During the course of treatment and especially where liver transplant is indicated, it may be necessary to evaluate the activity of HBV and thereby determine the extent of infection in the liver. One way of demonstrating the activity of the virus is to stain liver biopsies for core protein and an HBV surface antigen (HBsAg). Also important are tests for HBV cores, virus and e-antigen in serum. Currently, most HBV activity measurements and/or HBV-related tests are performed using antibody-based assays.

It has been found that heteroaryldihydropyrimidines (HAPs) enhance the rate and extent of HBV capsid protein assembly over a broad concentration range leading to aberrant particles, dominated by hexagonal arrays of capsid protein. HAPs also stabilize viral cores, thereby preventing normal dissociation and release of the viral genome (Stray, S. J., et al., 2005, Proc. Natl. Acad. Sci. USA 102:8138-8143). It is believed that such compounds disrupt HBV assembly, altering either the timing of formation of the capsid, the stability of the capsid, or the geometry of capsid formation, and interfering with viral infection accordingly. Targeting assembly of the HBV capsid protein, which has no human homolog, may therefore be a powerful, general approach for developing anti-HBV therapeutics. A hydrophobic groove, or "HAP pocket," exists as a gap at a protein-protein interface within the HBV core (Bourne et al. 2008). When that groove, or HAP pocket, is filled, either by HAP molecules, propenamides or by core protein mutations, the effect is antiviral. Thus far, all known HBV-specific core protein assembly effectors bind within the HAP pocket. Accordingly, the availability of fluorescent-HAP stains (compounds) having high affinity for the HAP pocket of HBV would enable competitive binding assays as a means by which to identify molecules as antiviral candidates.

Fluorescent-HAP stains (compounds) for core protein would also be of interest to those studying HBV biology, e.g., in tracking HBV cores in cells and organs. The life cycle of HBV is not well defined. Numerous questions exist pertaining to localization of assembly sites, sites where cores accumulate, and core interaction with exocytotic machinery. The availability of fluorescent-HAP stains (compounds) for addition to a culture medium that would diffuse into cells and accumulate at sites where there are HBV cores would allow ready identification of localization sites for HBV cores in cultured cells. In animals (e.g., mice, woodchucks, humans), such stains could be used to identify infected regions of liver and possibly other organs where HBV cores accumulate, as anticipated for "occult" infections.

The signature of an active HBV infection is the presence in serum of HBV cores and core-containing Dane particles (i.e., HBcAg or c-antigen). These are currently detected in clinical assays using antibodies. The availability of fluorescent-HAP stains (compounds) would offer an alternative that is highly specific for HBV cores. Likewise, the presence or absence of e-antigen, i.e., the aforementioned variant of HBV core antigen, is a marker for actively replicating HBV. Infections that are c-antigen positive, e-antigen negative are associated with severe progressive chronic infections. Antibody-based assays for e-antigen have had difficulty with cross-reactivity with HBV cores (i.e., c-antigen). Adjusting the conditions of a serum sample (e.g., raising ionic strength) would be expected to render the e-antigen readily detectable by a fluorescent-HAP stain (compound).

Rapid, effective tests for HBV cores in tissue enabled by the availability of fluorescent-HAP stains (compounds)

would be valuable for examining biopsies and other tissue samples for staging and grading infection liver damage, would have diagnostic value for examining patients with ambiguous clearance of acute infection, would allow evaluation of transplant candidates for the level of infection and for HBV in other targeted organs, and permit examination of samples from recent transplantees for evidence of reinfection. Thus, direct detection of HBV infection in concert with histological examination would be of value for considering treatment options for patients that have liver damage but minimal evidence of ongoing infection.

Notwithstanding the current availability of antibody-based HBV activity measurements and/or HBV-related tests, there remains a need for i) a clinical alternative to antibody-based HBV diagnostic reagents, ii) effective HBV-tracking agents, and iii) new tools for anti-HBV drug discovery, all of which needs would be supported by the availability of fluorescent-HAP stains (compounds).

SUMMARY

Described herein are compounds, compositions, methods, and kits for use in HBV detection and diagnosis, HBV-tracking, and in anti-HBV drug discovery. The compounds described herein are fluorescent-HAP stains, efficiently excitable over a broad excitation and emission range, which readily cross cell membranes, bind to HBV capsid, and thereby concentrate the associated fluorophore to provide brightly fluorescent punctate staining of HBV-expressing cells (up to 120 copies of fluorescent-HAP stain are bound per HBV capsid). The fluorescent-HAP stains (compounds) described herein bind in the HAP pocket of pre-assembled HBV cores with high nanomolar affinity, enhance the rate and extent of HBV capsid assembly, stabilize HBV capsids, and induce aberrant capsid assembly thereby retaining critical properties of HAPs. The fluorescent-HAP stains (compounds) described herein may be used in anti-HBV drug discovery to identify molecules that bind to the HAP pocket and in place of and/or in combination with currently-available antibody-based HBV diagnostic reagents to detect the presence in serum of HBV cores, core-containing Dane particles (i.e., HBcAg or c-antigen), and/or e-antigen. Also described herein are processes for preparing fluorescent-HAP stains (compounds) for use in the disclosed compositions, methods and kits.

In an illustrative embodiment of the present invention, a fluorescent-HAP stain (compound) having the structural formula (I)

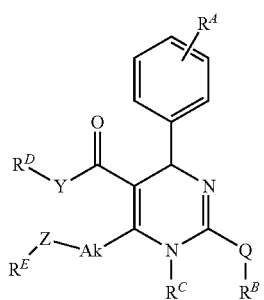

or a salt thereof is described, wherein: Q is $Ar^1$ or $Ak_1$;
$Ar^1$ is aryl or heteroaryl;
$R^C$ is hydrogen;
Ak and $Ak_1$ are independently $C_1$-$C_6$ alkylene;

Z is

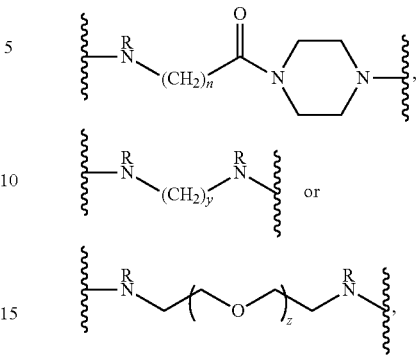

where n is 1, 2, 3, 4, 5, or 6; y is 6, 7, 8, 9, 10, 11 or 12; z is 1, 2, 3, or 4; and R is H or alkyl;
$R^D$ is alkyl, heteroalkyl, alkenyl, or alkynyl, each being optionally substituted;
$R^E$ is a FLUOROPHORE;
Y is O, S, or HN;
$R^A$ represents from 0 to 3 substituents independently in each instance, halo or selected from the group consisting of alkyl, heteroalkyl, aryl, heteroaryl, amino and derivatives thereof, and hydroxyl and derivatives thereof, each of which is optionally substituted; and
$R^B$ represents from 0 to 3 substituents independently in each instance, halogen or selected from the group consisting of alkyl, heteroalkyl, aryl, heteroaryl, amino and derivatives thereof, and hydroxyl and derivatives thereof, each of which is optionally substituted.

It is to be understood that all possible combinations of the various genera and subgenera of each of Q, $R^D$, $R^E$, $Ar^1$, Y, Ak, $Ak_1$, R, $R^A$, and $R^B$ represent additional illustrative embodiments of compounds described herein. It is to be further understood that each of those additional illustrative embodiments of compounds may be used in any of the compositions, methods, and/or kits described herein.

In another illustrative embodiment, a fluorescent-HAP stain (compound) having the structural formula (I) or a salt thereof is described, wherein: Q is $Ar^1$, where
$Ar^1$ is 2-thiazolyl, 2-thienyl, 2-furanyl, 2-(1-methyl)imidazolyl, 2-pyrimidinyl, 2-naphthyl, 2-pyrrolidinyl, phenyl, 2-pyridyl, 3-pyridyl, or 4-pyridyl; and each of $R^D$, $R^E$, Z, Y, Ak, R, $R^A$, and $R^B$ are as defined in any of the embodiments described herein.

In another illustrative embodiment, a fluorescent-HAP stain (compound) having the structural formula (I) or a salt thereof is described, wherein: Q is $Ar^1$, where $Ar^1$ is phenyl, 2-pyridyl, 3-pyridyl, or 4-pyridyl; and each of $R^D$, $R^E$, Z, Y, Ak, R, $R^A$, and $R^B$ are as defined in any of the embodiments described herein.

In another illustrative embodiment, compositions for use in HBV detection, HBV diagnosis, HBV-tracking, and/or anti-HBV drug discovery are described, which compositions include one or more of the fluorescent-HAP stains (compounds) described herein in an amount effective for detecting, diagnosing, tracking, and/or competitively binding to HBV. It is to be understood that the compositions described herein may include other components and/or ingredients, including, but not limited to, other diagnostically active compounds, and/or one or more carriers, diluents, excipients, and the like.

Another illustrative embodiment of the present invention provides a method for detecting, diagnosing, and/or tracking HBV in cells and tissue, the method being compatible for use in combination with, for example, currently-available antibody-based HBV detection and/or diagnostic methods, and including the steps of:

a) incubating a mixture of cells and an effective amount of one or more fluorescent-HAP stains (compounds) described herein or a composition thereof;

b) washing away any excess of said one or more compounds;

c) providing a stimulus to the mixture to elicit a fluorescent signal; and d) analyzing the stimulated mixture.

Another illustrative embodiment provides a method for detecting, diagnosing, and/or tracking HBV cores in solution, the method being compatible for use in combination with, for example, currently-available antibody-based HBV detection and/or diagnostic methods, and including the steps of:

a) incubating a solution comprising clarified serum, growth medium, or other liquid to be tested and an effective amount of one or more fluorescent-HAP stains (compounds) described herein or a composition thereof;

b) adjusting ionic strength, if necessary, to induce e-antigen assembly for the purpose of detecting said assembly;

c) separating unbound said one or more compounds from said one or more compounds bound to HBV cores to create an unbound phase and a bound phase, respectively; and d) analyzing the fluorescence associated with the unbound and bound phases.

Another illustrative embodiment provides a method for conducting anti-HBV drug discovery, the method including the steps of:

a) incubating a mixture of an anti-HBV drug candidate, pre-assembled HBV cores and an effective amount of one or more fluorescent-HAP stains (compounds) described herein or a composition thereof;

b) measuring a change in the fluorescence of the one or more fluorescent-HAP stains (compounds); and c) analyzing the mixture for competitive binding by the anti-HBV drug candidate to the HAP pocket of HBV.

Another illustrative embodiment provides a method for conducting anti-HBV drug discovery, the method including the steps of:

a) incubating a mixture of an anti-HBV drug candidate, pre-assembled HBV cores and an effective amount of one or more fluorescent-HAP stains (compounds) described herein or a composition thereof;

b) separating unbound said anti-HBV drug candidate and unbound said one or more fluorescent-HAP stains (compounds) from said anti-HBV drug candidate and said one or more fluorescent-HAP stains (compounds) bound to HBV cores to create an unbound phase and a bound phase, respectively;

c) measuring the fluorescence associated with the unbound and bound phases; and d) analyzing the mixture for competitive binding by the anti-HBV drug candidate to the HAP pocket of HBV.

Another illustrative embodiment provides a kit for detecting, diagnosing, and/or tracking HBV, as well identifying compounds that competitively bind to the HAP pocket of HBV, the kit being compatible for use in combination with, for example, currently-available antibody-based HBV detection and/or diagnostic reagents, and including:

a) a fluorescent-HAP stain (compound) described herein; and b) a suitable solvent.

Another illustrative embodiment provides a process for preparing a fluorescent-HAP stain having the structural formula (I)

the process comprising:

(a) reacting a HAP compound of structural formula

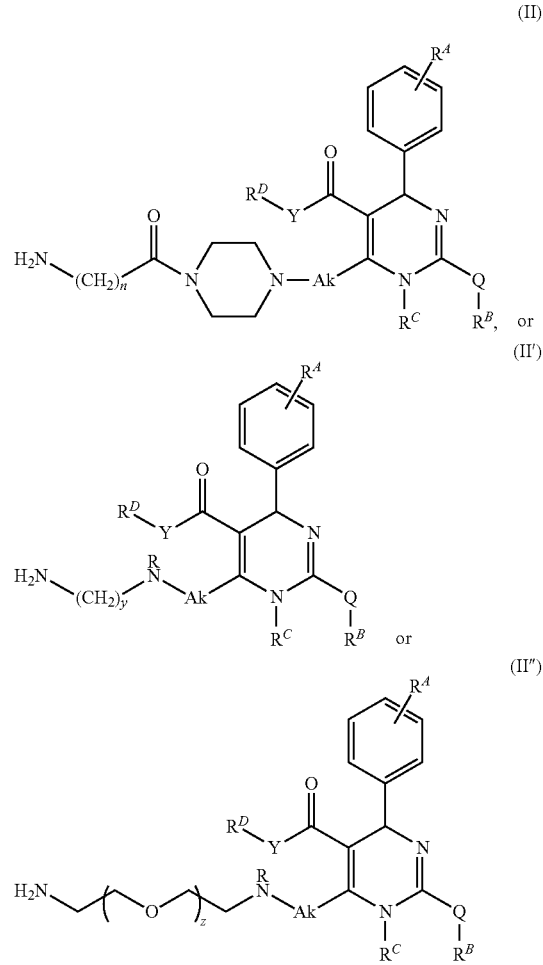

with a suitably activated FLUOROPHORE, wherein: Q is $Ak_1$ or $Ar^1$; and $R^C$, $R^D$, Ak, $Ak_1$, $Ar^1$, Z, Ak, R, $R^A$, $R^B$, n, y, z and FLUOROPHORE are as defined herein.

Another embodiment of the process is described wherein Q is $Ar^1$ wherein $R^C$, $R^D$, Ak, $Ar^1$, Z, Ak, R, $R^A$, $R^B$, n, y, z and FLUOROPHORE are as defined herein. Additional illustrative aspects, features and advantages of the present invention will become apparent to those skilled in the art upon consideration of the following detailed description exemplifying the best mode of carrying out the invention as presently perceived. It should be understood, however, that the detailed description and the specific examples that follow, while indicating preferred embodiments of the invention, are given by way of illustration only. It is expected that various changes and modifications within the spirit and scope of the present invention will become apparent to those skilled in the art.

BRIEF DESCRIPTION OF THE DRAWINGS

The detailed description particularly refers to the accompanying figures in which.

DETAILED DESCRIPTION

Figure 1:
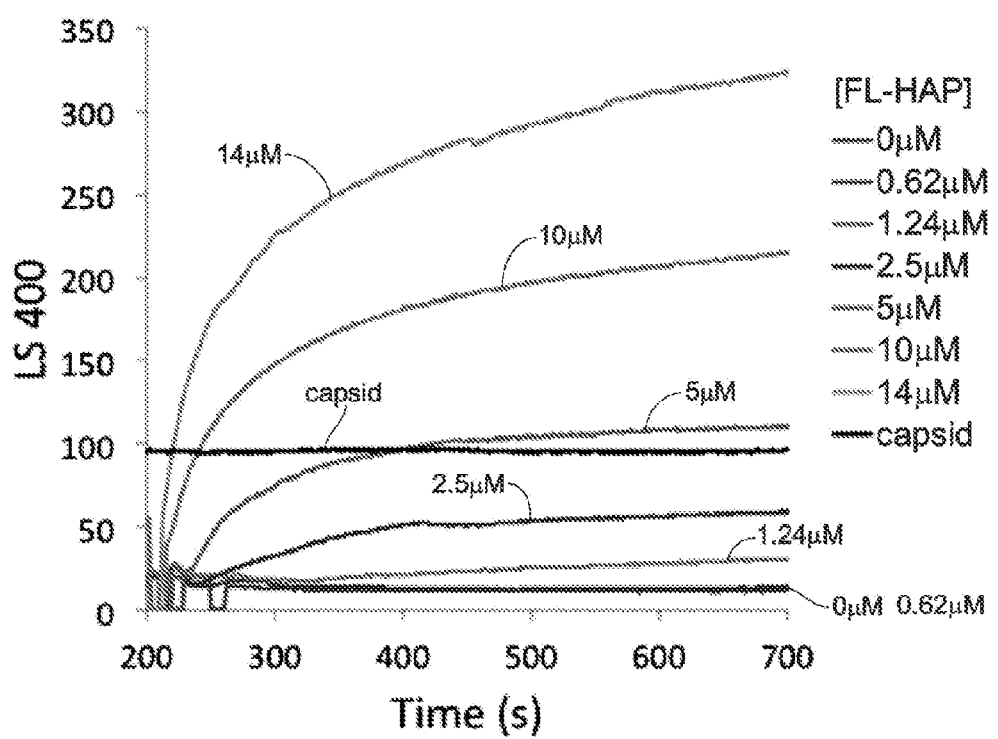
FIG. 1 shows that FL-HAP$_{AlexaFluor® 488}$ enhances HBV capsid assembly rate.

While the invention described herein is susceptible to various modifications and alternative forms, for the purposes of promoting an understanding of the principles of the invention, reference will now be made to a number of illustrative embodiments, and specific language will be used to describe the same. It should be understood, however, that there is no intent to limit the invention to the particular forms described, but rather, on the contrary, the intention is to cover all modifications, equivalents, and alternatives falling within the spirit and scope of the invention.

The present invention includes compounds, compositions, methods, and kits for use in HBV detection and diagnosis, HBV-tracking, and in anti-HBV drug discovery. The compounds described herein are fluorescent-HAP stains, efficiently excitable over a broad excitation and emission range, which readily cross cell membranes, bind to HBV capsid, and thereby concentrate the associated fluorophore to provide brightly fluorescent punctate staining of HBV-expressing cells (up to 120 copies of fluorescent-HAP stain are bound per HBV capsid). The fluorescent-HAP stains (compounds) described herein bind in the HAP pocket of pre-assembled HBV cores with high nanomolar affinity, enhance the rate and extent of HBV capsid assembly, stabilize HBV capsids, and induce aberrant capsid assembly thereby retaining critical properties of HAPs. The fluorescent-HAP stains (compounds) described herein may be used in anti-HBV drug discovery to identify molecules that bind to the HAP pocket and in place of and/or in combination with currently-available antibody-based HBV diagnostic reagents to detect the presence in serum of HBV cores, core-containing Dane particles (i.e., HBcAg or c-antigen), and/or e-antigen. Also described herein are processes for preparing fluorescent-HAP stains (compounds) for use in the compositions, methods and kits disclosed herein.

In an illustrative embodiment of the present invention, a fluorescent-HAP stain (compound) having the structural formula (I)

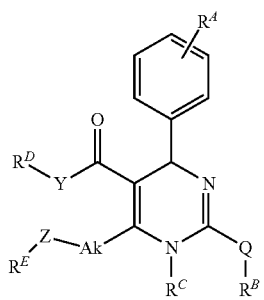

(I)

or a salt thereof is described, wherein: Q is $Ar^1$ or $Ak_1$;
$Ar^1$ is aryl or heteroaryl;
$R^C$ is hydrogen;
Ak and $Ak_1$ are independently $C_1$-$C_6$ alkylene;

Z is

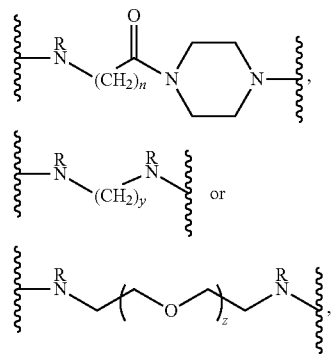

where n is 1, 2, 3, 4, 5, or 6; y is 6, 7, 8, 9, 10, 11 or 12; z is 1, 2, 3, or 4; and R is H or alkyl;

$R^D$ is alkyl, heteroalkyl, alkenyl, or alkynyl, each being optionally substituted;

$R^E$ is a FLUOROPHORE;

Y is O, S, or HN;

$R^A$ represents from 0 to 3 substituents independently in each instance, halo or selected from the group consisting of alkyl, heteroalkyl, aryl, heteroaryl, amino and derivatives thereof, and hydroxyl and derivatives thereof, each of which is optionally substituted; and $R^B$ represents from 0 to 3 substituents independently in each instance, halogen or selected from the group consisting of alkyl, heteroalkyl, aryl, heteroaryl, amino and derivatives thereof, and hydroxyl and derivatives thereof, each of which is optionally substituted.

It is to be understood that all possible combinations of the various genera and subgenera of each of $R^D$, $R^E$, $Ar^1$, Z, Y, Ak, $Ak_1$, R, $R^A$, and $R^B$ represent additional illustrative embodiments of compounds of the invention described herein. It is to be further understood that each of those additional illustrative embodiments of compounds may be used in any of the compositions, methods, and/or kits described herein.

In another illustrative embodiment, a fluorescent-HAP stain (compound) having the structural formula (I) or a salt thereof is described, wherein:

Q is $Ar^1$, where $Ar^1$ is 2-thiazolyl, 2-thienyl, 2-furanyl, 2-(1-methyl)imidazolyl, 2-pyrimidinyl, 2-naphthyl, 2-pyrrolidinyl, phenyl, 2-pyridyl, 3-pyridyl, or 4-pyridyl; and each of $R^D$, $R^E$, Z, Y, Ak, R, $R^A$, and $R^B$ are as defined in any of the embodiments described herein.

In another illustrative embodiment, a fluorescent-HAP stain (compound) having the structural formula (I) or a salt thereof is described, wherein:

$Ar^1$ is phenyl, 2-pyridyl, 3-pyridyl, or 4-pyridyl; and each of $R^D$, $R^E$, Z, Y, Ak, R, $R^A$, and $R^B$ are as defined in any of the embodiments described herein.

In an illustrative embodiment, a fluorescent-HAP stain (compound) having the structural formula (I) or (Ia) or a salt thereof is described, wherein FLUOROPHORE is selected from the group consisting of xanthenes, including but not limited to fluorescein, rhodamine, rhodol, rosamine, and derivatives thereof, coumarins, acridines, furans, indoles, quinolines, cyanines, benzofurans, quinazolinones, benzazoles, boron-dipyrromethenes, and derivatives thereof.

In another illustrative embodiment, compounds of formula (I) are described wherein Q is $Ar^1$, where $Ar^1$ is 2-pyridyl or 3-pyridyl. In another illustrative aspect, compounds of formula (I) are described wherein $R^B$ is absent. In another illustrative aspect, compounds of formula (I) or (Ia) are described wherein Y is O or S. In another illustrative aspect, compounds of formula (I) or (Ia) are described wherein $R^D$ is methyl. In another illustrative aspect, compounds of formula (Ia) are described wherein $Ak_1$ is $C_1$-$C_4$ or $C_1$-$C_3$, or $C_1$-$C_2$. In another illustrative aspect, compounds of formula (Ia) are described wherein $Ak_1$ is $CH_2$. In another illustrative aspect, compounds of formula (I) are described wherein Q is $Ar^1$, where $Ar^1$ is 2-pyridyl, $R^B$ is absent, Y is O, and $R^D$ is methyl. In another illustrative aspect, compounds of formula (I) are described wherein Q is $Ar^1$, where $Ar^1$ is 2-pyridyl, $R^B$ is absent, Y is O, $R^D$ is methyl, and FLUOROPHORE is a rhodamine derivative, fluorescein or a derivative thereof, or a boron-dipyrromethene derivative.

It is to be understood that all possible combinations of the various genera and subgenera of each of Q, $R^D$, $R^E$, $Ar^1$, Z, Ak, $Ak_1$, R, $R^A$, and $R^B$ represent additional illustrative embodiments of compounds of the invention described herein. It is to be further understood that each of the aforementioned additional illustrative embodiments of compounds may be used in any of the compositions, methods, and/or kits described herein.

In each of the foregoing and each of the following embodiments, it is also to be understood that the formulae include and represent not only all pharmaceutically and diagnostically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is to be further understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

In another illustrative embodiment, a fluorescent-HAP stain (compound) having the structural formula (III) or (IV)

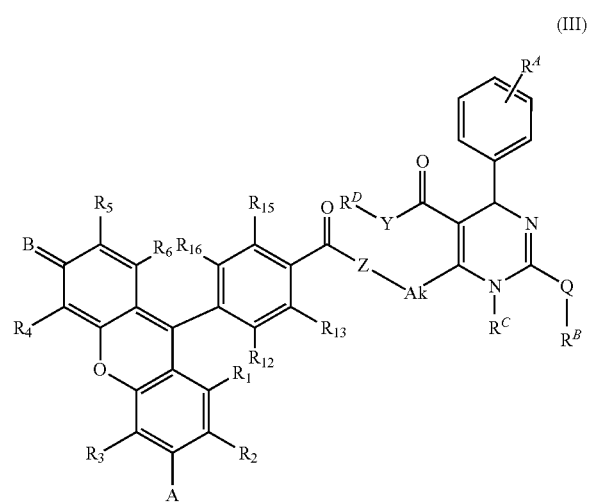

(III)

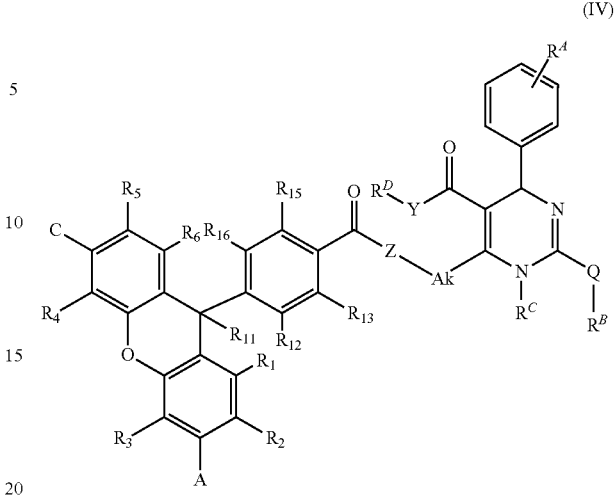

(IV)

or a salt thereof is described, wherein Q is $Ak_1$ or $Ar^1$, and $R^C$, $R^D$, $Ar^1$, Z, Ak, $Ak_1$, $R^A$, and $R^B$ are as defined herein;

$R_2$, $R_3$, $R_4$ and $R_5$ are independently H, F, Cl, Br, I, CN; or $C_1$-$C_{18}$ alkyl, or $C_1$-$C_{18}$ alkoxy, where each alkyl or alkoxy is optionally further substituted by F, Cl, Br, I, a carboxylic acid, a salt of carboxylic acid, or a carboxylic acid ester of a $C_1$-$C_6$ alcohol; or —$SO_3X$ where X is H or a counterion;

$R_1$ and $R_6$ are H; or $R_1$ taken in combination with $R_2$ or $R_5$ taken in combination with $R_6$ or both, form a fused aromatic six-membered ring that is optionally substituted one or more times by —$SO_3X$;

A is $NR^8R^9$, where $R^8$ and $R^9$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl; or $R_8$ in combination with $R_9$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$-$C_6$ alkyl;

or $R_8$ in combination with $R_2$, or $R_9$ in combination with $R_3$, or both, form a 5- or 6-membered ring that is saturated or unsaturated, and is optionally substituted by one or more $C_1$-$C_6$ alkyls or —$CH_2SO_3X$ moieties;

C is $OR_{17}$ or $NR^{18}R^{19}$; where $R_{17}$ is H, or $C_1$-$C_{18}$ alkyl, $R^{18}$ and $R^{19}$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl; or $R_{18}$ in combination with $R_{19}$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$-$C_6$ alkyl;

or $R^{18}$ in combination with $R_4$, or $R^{19}$ in combination with $R_5$, or both, form a 5- or 6-membered ring that is saturated or unsaturated, and is optionally substituted by one or more $C_1$-$C_6$ alkyls or —$CH_2SO_3X$ moieties;

B is O or $N^+R^{18}R^{19}$;

$R_{12}$, $R_{13}$, $R_{15}$, and $R_{16}$ are independently H, F, Cl, Br, I, —$SO_3X$, a carboxylic acid, a salt of carboxylic acid, CN, nitro, hydroxy, azido, amino, hydrazino; or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_6$-$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$-$C_6$ alcohol, —$SO_3X$, amino, alkylamino, dialkylamino or alkoxy, the alkyl portions of each having 1-6 carbons; or one pair of adjacent substituents $R_{12}$ and $R_{13}$ or $R_{15}$ and $R_{16}$, when taken in combination, form a fused 6-membered aromatic ring that is optionally further substituted by carboxylic acid, or a salt of carboxylic acid; and $R_{11}$ is H, hydroxy, CN or a $C_1$-$C_6$ alkoxy; or $R_{11}$ in combination with $R_{12}$ forms a 5- or 6-membered spirolactone ring or a 5- or 6-membered spirosultone ring that is optionally and independently substituted by H, F or $CH_3$.

In one illustrative aspect, compounds of formulae (III) and (IV) are described wherein at least one of $R_2$, $R_3$, $R_4$, and $R_5$ is —$SO_3X$. In another illustrative aspect, compounds of formulae (III) and (IV) are described wherein R8 in combination with $R_2$, or $R_9$ in combination with $R_3$, or $R_{18}$ in combination with $R_4$, or $R_{19}$ in combination with $R_5$, form a 5- or 6-membered ring that is saturated or unsaturated, and is substituted at a carbon atom by at least one —$CH_2SO_3X$ moiety. In another illustrative aspect, compounds of formulae (III) and (IV) are described wherein $R_3$ and $R_4$ are each —$SO_3X$. In another illustrative aspect, compounds of formulae (III) and (IV) are described wherein $R_{12}$ is a carboxylic acid, a salt of carboxylic acid, or —$SO_3X$; and $R_{11}$ is not present. In another illustrative aspect, compounds of formulae (III) and (IV) are described wherein at least three of $R_{12}$, $R_{13}$, $R_{15}$, and $R_{16}$ are F or Cl. In another illustrative aspect, compounds of formulae (III) and (IV) are described wherein A is $NR^8R^9$, B is O and C is $OR_{17}$. In another aspect, compounds of formulae (III) and (IV) are described wherein A is $NR^8R^9$, B is $N^+R^{18}R^{19}$, and C is $NR^{18}R^{19}$. In another illustrative aspect, compounds of formulae (III) and (IV) are described wherein $R_3$ and $R_4$ are each —$SO_3X$.

In another illustrative aspect, compounds of formulae (III) and (IV) are described wherein $R_8$ in combination with $R_2$ forms a 5- or 6-membered ring that is saturated or unsaturated, and is optionally substituted by one or more $C_1$-$C_6$ alkyls or —$CH_2SO_3X$ moieties; and $R^{19}$ in combination with $R_5$ forms a 5- or 6-membered ring that is saturated or unsaturated, and is optionally substituted by one or more $C_1$-$C_6$ alkyls or —$CH_2SO_3X$ moieties. In another illustrative aspect, compounds of formulae (III) and (IV) are described wherein $R^9$ and $R^{18}$ are independently H, $C_1$-$C_6$ carboxyalkyl, a salt of $C_1$-$C_6$ carboxyalkyl, $C_1$-$C_6$ sulfoalkyl, or a salt of $C_1$-$C_6$ sulfoalkyl. In another illustrative aspect, compounds of formulae (III) and (IV) are described wherein $R^8$ in combination with $R_2$, and $R^{19}$ in combination with $R_5$, each form a 5- or 6-membered ring that is saturated; and $R_3$ and $R_4$ are each —$SO_3X$. In another illustrative aspect, compounds of formulae (III) and (IV) are described wherein $R^8$ in combination with $R_2$ forms a 5- or 6-membered ring that is saturated or unsaturated, and is substituted by —$CH_2SO_3X$; and $R^{19}$ in combination with $R_5$ forms a 5- or 6-membered ring that is saturated or unsaturated, and is substituted at a carbon atom by —$CH_2SO_3X$. In another illustrative aspect, compounds of formulae (III) and (IV) are described wherein $R_1$, $R_2$, $R_5$, and $R_6$ are H; $R^8$, $R^9$, $R^{18}$, and $R^{19}$ are H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl.

Another illustrative embodiment, a fluorescent-HAP stain (compound) having the structural formula (V) or (VI)

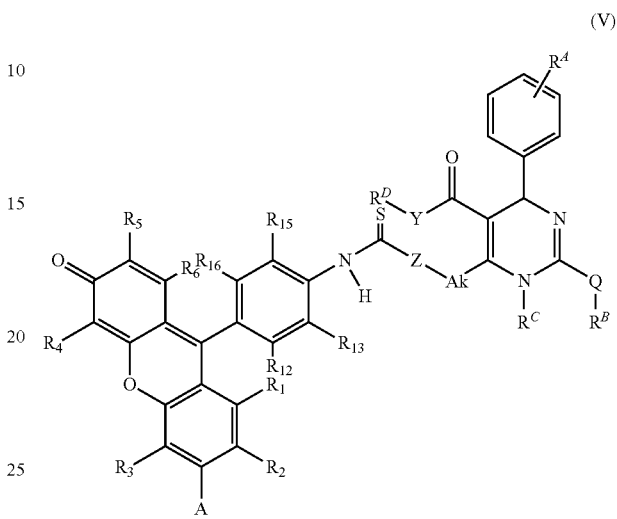

(V)

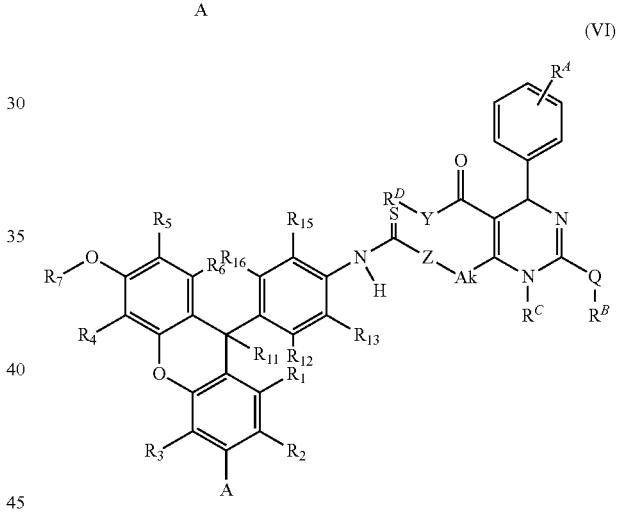

(VI)

or a salt thereof is described, wherein: Q is $Ak_1$ or $Ar^1$, and $R^C$, $R^D$, $Ar^1$, Z, Ak, $Ak_1$, $R^A$, and $R^B$ are as defined herein, $R_1$ and $R_6$ are independently H, F, Cl, Br, I, $C_1$-$C_{18}$ alkyl or $C_1$-$C_{18}$ alkoxy;

$R_2$, $R_3$, $R_4$ and $R_5$ are independently H, F, Cl, Br, I, CN; or $C_1$-$C_{18}$ alkyl, $C_1$-$C_{18}$ alkoxy or $C_1$-$C_{18}$ alkylthio, where each alkyl, alkoxy or alkylthio is optionally further substituted by F, Cl, Br, I, sulfonic acid, salt of sulfonic acid, carboxylic acid, a salt of carboxylic acid, a carboxylic acid ester of a $C_1$-$C_6$ alkyl, a carboxylic acid ester of —$CH_2$—O—(C=O)—$R_{18}$ where $R_{18}$ is a $C_1$-$C_4$ alkyl; or amino, alkylamino, dialkylamino, or alkoxy, the alkyl portions of which independently have 1-6 carbons; or one or both of $R_3$ and $R_4$ are —$CH_2N(CH_2COOR_{17})_2$, where $R_{17}$ is H, a biologically compatible counterion, a linear or branched alkyl having 1-6 carbons, or —$CH_2$—O—(C=O)—$R_{18}$;

A is $OR_7$ or $NR^8R^9$, where each $R_7$ is independently H, $C_1$-$C_{18}$ alkyl, a $C_1$-$C_{18}$ acyl wherein each alkyl group independently has 1-6 carbons and is optionally substituted by amino, hydroxy, carboxylic acid, a salt of carboxylic acid, a carboxylic acid ester of a $C_1$-$C_6$ alkyl, a carboxylic acid ester of —$CH_2$—O—(C═O)—$R_{18}$; or trialkylsilyl wherein each alkyl group independently has 1-6 carbons;

$R^8$ and $R^9$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, a salt of $C_1$-$C_6$ sulfoalkyl, or $C_1$-$C_{18}$ acyl wherein the alkyl portions are optionally substituted by amino, hydroxy, carboxylic acid, a salt of carboxylic acid, a carboxylic acid ester of a $C_1$-$C_6$ alkyl, a carboxylic acid ester of —$CH_2$—O—(C═O)—$R_{18}$; or $R^8$ in combination with $R_2$, or $R^9$ in combination with $R_3$, or both, form a saturated 5- or 6-membered ring that is optionally substituted by one or more methyls; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$-$C_6$ alkyl, or a carboxylic acid ester of —$CH_2$—O—(C═O)—$R_{18}$;

$R_{12}$, $R_{13}$, $R_{15}$ and $R_{16}$ are independently H, F, Cl, Br, I; or sulfonic acid, salt of sulfonic acid, carboxylic acid, a salt of carboxylic acid, a carboxylic acid ester of a $C_1$-$C_6$ alkyl, a carboxylic acid ester of —$CH_2$—O—(C═O)—$R_{18}$, CN, nitro, hydroxy, azido, amino, hydrazino; or $C_1$-$C_{18}$ alkyl, $C_1$-$C_{18}$ alkoxy, $C_1$-$C_{18}$ alkylthio, $C_1$-$C_{18}$ alkylamino, $C_1$-$C_{18}$ alkylester, $C_1$-$C_{18}$ alkylamido or $C_1$-$C_{18}$ arylamido, the alkyl or aryl portions of which are optionally substituted one or more times by F, Cl, Br, I, hydroxy, carboxylic acid, a salt of carboxylic acid, a carboxylic acid ester of a $C_1$-$C_6$ alkyl, a carboxylic acid ester of —$CH_2$—O—(C═O)—$R_{18}$, sulfonic acid, salt of sulfonic acid, amino, alkylamino, dialkylamino or alkoxy, the alkyl portions of each having 1-6 carbons; or one pair of adjacent substituents $R_{12}$ and $R_{13}$ or $R_{15}$ and $R_{16}$, when taken in combination, form a fused 6-membered aromatic ring that is optionally further substituted by carboxylic acid, a salt of carboxylic acid, a carboxylic acid ester of a $C_1$-$C_6$ alkyl, a carboxylic acid ester of —$CH_2$—O—(C═O)—$R_{18}$; and $R_{11}$ is H, hydroxy, CN or a $C_1$-$C_6$ alkoxy; or $R_{11}$ in combination with $R_{12}$ forms a 5- or 6-membered spirolactone ring or a 5- or 6-membered spirosultone ring that is optionally and independently substituted by H, F or $CH_3$.

In one illustrative aspect, compounds are formulae (V) and (VI) are described wherein at least one of $R_1$, $R_2$, $R_3$, $R_4$, $R_5$, and $R_6$ is F. In another illustrative aspect, compounds are formulae (V) and (VI) are described wherein at least three of $R_{12}$, $R_{13}$, $R_{15}$ and $R_{16}$ are F. In another illustrative aspect, compounds are formulae (V) and (VI) are described wherein at least one of $R_2$, $R_3$, $R_4$ or $R_5$ is F. In another illustrative aspect, compounds are formulae (V) and (VI) are described wherein $R_2$ and $R_5$ are F. In another illustrative aspect, compounds are formulae (V) and (VI) are described wherein at least one of $R_{12}$, $R_{13}$, $R_{15}$, or $R_{16}$ is F. In another illustrative aspect, compounds are formulae (V) and (VI) are described wherein none of $R_{12}$, $R_{13}$, $R_{15}$, or $R_{16}$ is F. In another illustrative aspect, compounds are formulae (V) and (VI) are described wherein at least one of $R_{13}$, $R_{15}$, or $R_{16}$ is F. In another illustrative aspect, compounds are formulae (V) and (VI) are described wherein each of $R_{13}$, $R_{15}$, and $R_{16}$ is F. In another illustrative aspect, compounds are formulae (V) and (VI) are described wherein none of $R_1$, $R_2$, $R_3$, $R_4$, $R_5$ or $R_6$ is F. In another illustrative aspect, compounds are formulae (V) and (VI) are described wherein A is $OR_7$. In another illustrative aspect, compounds are formulae (V) and (VI) are described wherein each $R_7$ is H. In another illustrative aspect, compounds are formulae (V) and (VI) are described wherein at least one of $R_1$, $R_2$, $R_3$, $R_4$, $R_5$ or $R_6$ is F; and $R_{11}$ is H.

In another illustrative aspect, compounds are formulae (V) and (VI) are described wherein at least one of $R_{12}$, $R_{13}$, $R_{15}$ or $R_{16}$ is F; and $R_{11}$ is H. In another illustrative aspect, compounds are formulae (V) and (VI) are described wherein $R_{12}$ is a carboxylic acid or a salt of carboxylic acid. In another illustrative aspect, compounds are formulae (V) and (VI) are described wherein A is $NR^8R^9$. In another illustrative aspect, compounds are formulae (V) and (VI) are described wherein $R_1$ and $R_6$ are independently H or F. In another illustrative aspect, compounds are formulae (V) and (VI) are described wherein $R_{12}$ is sulfonic acid or a salt of sulfonic acid. In another illustrative aspect, compounds are formulae (V) and (VI) are described wherein each of substituents $R_1$, $R_2$, $R_3$, $R_4$, $R_5$, $R_6$, $R_{13}$, $R_{14}$, $R_{15}$ and $R_{16}$ are either F or H and at least one of $R_1$, $R_2$, $R_3$, $R_4$, $R_5$, $R_6$, $R_{13}$, $R_{14}$, $R_{15}$ and $R_{16}$ is F. In another illustrative aspect, compounds are formulae (V) and (VI) are described wherein $R_1$ and $R_6$ are H and $R_2$, $R_3$, $R_4$, $R_5$ are independently H, F, Cl, Br or I. In another illustrative aspect, compounds are formulae (V) and (VI) are described wherein A is $OR_7$, and one or both of $R_3$ and $R_4$ are —$CH_2N(CH_2COOR_{17})$.

In another illustrative embodiment, a fluorescent-HAP stain (compound) having the structural formula (VII)

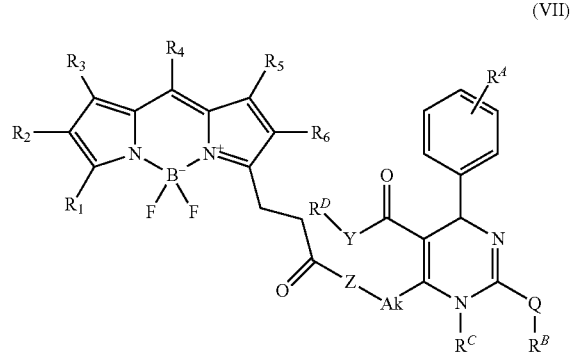

(VII)

or a salt thereof is described, wherein: Q is $Ak_1$ or $Ar^1$, and $R^C$, $R^D$, $Ar^1$, Z, Ak, $Ak_1$, $R^A$, and $R^B$ are as defined herein, and $R_1$, $R_2$, $R_3$, $R_4$, $R_5$, and $R_6$ are each independently H, halogen, alkyl, cycloalkyl, aryl, arylalkyl, acyl or sulfo.

In one illustrative aspect, compounds of formula (VII) are described wherein $R_1$, $R_2$, $R_3$, $R_4$, $R_5$, and $R_6$ are each alkyl. In another illustrative aspect, compounds of formula (VII) are described wherein $R_1$ and $R_3$ are alkyl. In another illustrative aspect, compounds of formula (VII) are described wherein $R_1$ and $R_2$ are aryl. In another illustrative aspect, compounds of formula (VII) are described wherein $R_1$, $R_2$, $R_3$, $R_4$, $R_5$, and $R_6$ are each H. In another illustrative aspect, compounds of formula (VII) are described wherein $R_3$ and $R_5$ are aryl. In another illustrative aspect, compounds of formula (VII) are described wherein $R_2$ and $R_6$ are alkyl. In another illustrative aspect, compounds of formula (VII) are described wherein $R_2$ and $R_6$ are aryl. In another illustrative aspect, compounds of formula (VII) are described wherein $R_4$ is aryl. In another illustrative aspect, compounds of formula (VII) are described wherein $R_1$ and $R_3$ are cycloalkyl.

In another illustrative aspect, compounds of formula (VII) are described wherein $R_4$ is arylalkyl. In another illustrative aspect, compounds of formula (VII) are described wherein $R_1$ and $R_3$ are halogen. In another illustrative aspect, compounds of formula (VII) are described wherein $R_1$ and $R_2$ are acyl. In another illustrative aspect, compounds of formula (VII) are described wherein $R_3$ and $R_5$ are sulfo. In another illustrative aspect, compounds of formula (VII) are described wherein $R_2$, $R_3$, $R_5$ and $R_6$ are H. In another illustrative aspect, compounds of formula (VII) are described wherein $R_2$, $R_3$, $R_5$ and $R_6$ are alkyl. In another illustrative aspect, compounds of formula (VII) are described wherein $R_3$ and $R_5$ are acyl. In another illustrative aspect, compounds of formula (VII) are described wherein $R_4$ is arylalkyl. In another illustrative aspect, compounds of formula (VII) are described wherein $R_3$ and $R_5$ are cycloalkyl. In another illustrative aspect, compounds of formula (VII) are described wherein $R_2$, $R_3$, $R_5$ and $R_6$ are H. In another illustrative aspect, compounds of formula (VII) are described wherein $R_2$, $R_3$, $R_5$ and $R_6$ are aryl. In another illustrative aspect, compounds of formula (VII) are described wherein $R_3$ and $R_5$ are halogen. In another illustrative aspect, compounds of formula (VII) are described wherein $R_3$, $R_4$ and $R_5$ are arylalkyl.

In another embodiment, the following illustrative Compounds 5, 6 and 7, representative of general formulae (III), (V) and (VII), respectively, and salts thereof, are described:

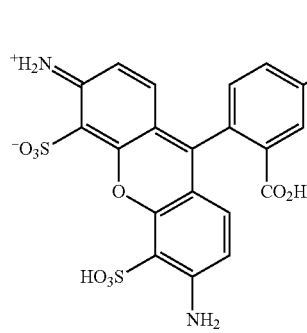
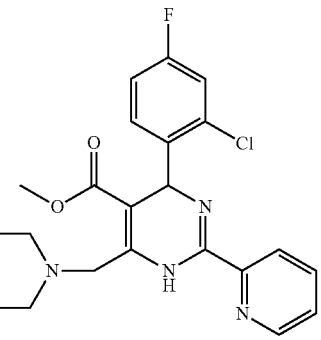

5

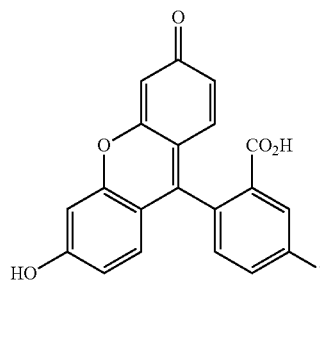

6

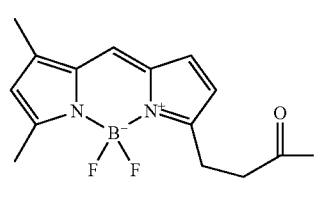

7

Illustrative derivatives of the aforementioned compounds include, but are not limited to, both those compounds that may be synthetically prepared from the compounds described herein, as well as those compounds that may be prepared in a similar way as those described herein, but differing in the selection of starting materials. In addition, it is to be understood that derivatives of those compounds also include the compounds having those same or different functional groups at different positions on the various aromatic rings. Similarly, derivatives include parallel variations of other functional groups on the compounds described herein, such as Q, $R^C$, $R^D$, $Ar^1$, Z, Ak, $Ak_1$, $R^A$, and $R^B$.

In another illustrative embodiment, a fluorescent-HAP stain (compound) having the structural formula (VIII) or (IX)

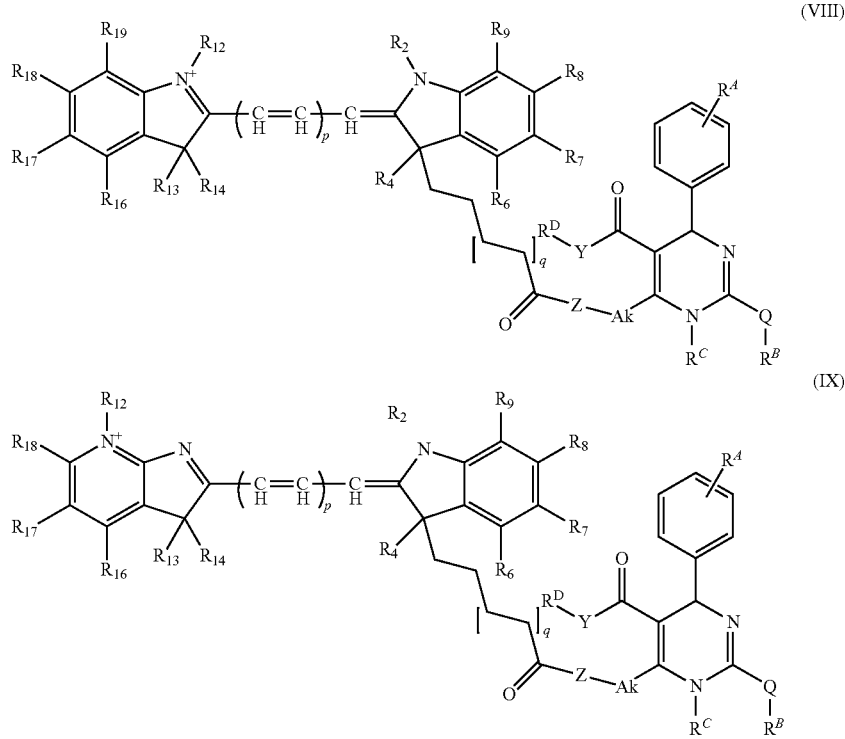

or a salt thereof is described, wherein: Q is $Ak_1$ or $Ar^1$, and $R^C$, $R^D$, $Ar^1$, Z, Ak, $Ak_1$, $R^A$, and $R^B$ are as defined herein, $R_4$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by substituents selected from the group consisting of F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium;

$R_2$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, $C_2$-$C_{12}$ dialkylamino, or $C_3$-$C_{18}$ trialkylammonium;

$R_6$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_7$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_8$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_9$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{16}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{17}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{18}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{19}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

or a member independently selected from
$R_6$ in combination with $R_7$;
$R_7$ in combination with $R_8$;

$R_8$ in combination with $R_9$;
$R_{16}$ in combination with $R_{17}$;
$R_{17}$ in combination with $R_{18}$; and
$R_{18}$ in combination with $R_{19}$
together with the atoms to which they are joined, form an aromatic ring comprising —CH— or —CR$^1$— wherein $R^1$ is amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, wherein each alkyl portion of which is optionally substituted by substituents selected from the group consisting of carboxy, sulfo, amino, and hydroxyl;

p is 1, 2 or 3;
q is 0, 1, 2 or 3;

$R_{12}$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, $C_2$-$C_{12}$ dialkylamino, or $C_3$-$C_{18}$ trialkylammonium;

$R_{13}$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium;

$R_{14}$ is $C_1$-$C_{22}$ alkyl or $C_7$-$C_{22}$ arylalkyl, each alkyl portion of which optionally incorporates up to six hetero atoms, selected from N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium;

or $R_{13}$ and $R_{14}$ taken in combination complete a five- or six-membered saturated or unsaturated ring that is optionally substituted; and wherein sulfo is sulfonic acid or sulfonate.

In one illustrative aspect, compounds of formulae (VIII) and (IX) are described wherein $R_2$ is sulfoalkyl. In another illustrative aspect, compounds of formulae (VIII) and (IX) are described wherein $R_{12}$ is alkyl. In another illustrative aspect, compounds of formulae (VIII) and (IX) are described wherein $R_{12}$ is ethyl. In another illustrative aspect, compounds of formulae (VIII) and (IX) are described wherein $R_4$ is methyl. In another illustrative aspect, compounds of formulae (VIII) and (IX) are described wherein $R_{14}$ is methyl. In another illustrative aspect, compounds of formulae (VIII) and (IX) are described wherein each of the sulfoalkyl groups are sulfopropyl groups. In another illustrative aspect, compounds of formulae (VIII) and (IX) are described wherein $R_7$ and $R_{17}$ are sulfo. In another illustrative aspect, compounds of formulae (VIII) and (IX) are described wherein n is 1. In another illustrative aspect, compounds of formulae (VIII) and (IX) are described wherein n is 2. In another illustrative aspect, compounds of formulae (VIII) and (IX) are described wherein $R_{16}$ is alkyl. In another illustrative aspect, compounds of formulae (VIII) and (IX) are described wherein $R_2$ is alkyl or sulfoalkyl. In another illustrative aspect, compounds of formulae (VIII) and (IX) are described wherein $R_{12}$ is alkyl or sulfoalkyl. In another illustrative aspect, compounds of formulae (VIII) and (IX) are described wherein $R_{13}$ is sulfoalkyl.

In another illustrative aspect, compounds of formulae (VIII) and (IX) are described wherein $R_4$, $R_{13}$ and $R_{14}$ are each methyl. In another illustrative aspect, compounds of formulae (VIII) and (IX) are described wherein $R_7$ and $R_{17}$ are each sulfo. In another illustrative aspect, compounds of formulae (VIII) and (IX) are described wherein $R_2$ and $R_{12}$ are independently methyl or sulfopropyl. In another illustrative aspect, compounds of formulae (VIII) and (IX) are described wherein $R_6$, $R_8$, $R_9$, $R_{16}$, $R_{17}$ and $R_{18}$ are each H. In another illustrative aspect, compounds of formulae (VIII) and (IX) are described wherein $R_6$, $R_8$, $R_9$, $R_{16}$, and $R_{18}$ are each H. In another illustrative aspect, compounds of formulae (VIII) and (IX) are described wherein $R_8$, $R_9$, $R_{16}$, and $R_{18}$ are each H. In another illustrative aspect, compounds of formulae (VIII) and (IX) are described wherein $R_7$ is sulfo. In another illustrative aspect, compounds of formulae (VIII) and (IX) are described wherein $R_{17}$ is halogen. In another illustrative aspect, compounds of formulae (VIII) and (IX) are described wherein $R_6$ in combination with $R_7$ together with the atoms to which they are joined form an aromatic ring comprising —CH— or —CR$^1$— wherein $R^1$ is sulfo.

In another illustrative embodiment, a fluorescent-HAP stain (compound) having the structural formula (X)

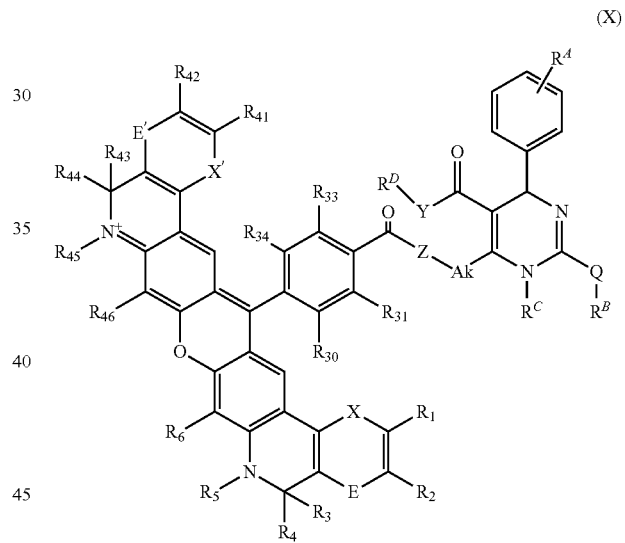

(X)

or a salt thereof is described, wherein: Q is $Ak_1$ or $Ar^1$, and $R^C$, $R^D$, $Ar^1$, Z, Ak, $Ak_1$, $R^A$, and $R^B$ are as defined herein, $R_1$, $R_2$, $R_6$, $R_{41}$, $R_{42}$, and $R_{46}$ are independently selected from the group consisting of hydrogen, cyano, halogen, carboxylic acid, sulfonic acid $C_1$-$C_6$ alkyl, $C_1$-$C_6$ alkoxy, aryl, heteroaryl, wherein said alkyl or alkoxy is optionally substituted by carboxylic acid, sulfonic acid, or halogen and said aryl or heteroaryl is optionally substituted one or more times by $C_1$-$C_6$ alkyl, $C_1$-$C_6$ perfluoroalkyl, cyano, halogen, azido, carboxylic acid, sulfonic acid, or halomethyl;

or $R_1$ in combination with $R_2$, or $R_{41}$ in combination with $R_{42}$, or both, forms a fused aromatic or heteroaromatic ring that is optionally sulfonated one or more times;

$R_3$, $R_4$, $R_{43}$, and $R_{44}$ are independently selected from the group consisting of hydrogen, $C_1$-$C_6$ alkyl, an aromatic or heteroaromatic ring, wherein said alkyl is optionally substituted by carboxylic acid, sulfonic acid, amino, hydroxy, or halogen and said aromatic or heteroaromatic ring that is optionally substituted one or more times by $C_1$-$C_6$ alkyl, $C_1$-$C_6$ alkoxy, $C_1$-$C_6$ perfluoroalkyl, cyano, halogen, carboxylic acid, sulfonic acid, or halomethyl;

or $R_2$ in combination with $R_3$, $R_{42}$ in combination with $R_{43}$, or $R_3$ in combination with $R_4$, or $R_{43}$ in combination with $R_{44}$, or any combination thereof, forms a 5- or 6-membered alicyclic ring;

$R_5$ and $R_{45}$ are independently selected from the group consisting of hydrogen, methyl, carboxymethyl, $C_2$-$C_6$ alkyl, or heteroaryl, wherein said alkyl is optionally substituted by carboxylic acid, sulfonic acid, amino, or halogen and said aryl or heteroaryl is optionally substituted one or more times by $C_1$-$C_6$ alkyl, $C_1$-$C_6$ perfluoroalkyl, cyano, halogen, carboxylic acid, sulfonic acid, or halomethyl;

or $R_4$ in combination with $R_5$, or $R_5$ in combination with $R_6$, or $R_{44}$ in combination with $R_{45}$, or $R_{45}$ in combination with $R_{46}$, or any combination thereof, forms a 5- or 6-membered alicyclic ring;

wherein E, E', X' and X is O, S, or $NR^8$ provided that E and X or E' and X' are not both present;

wherein $R^8$ is independently selected from the group consisting of hydrogen, methyl, carboxymethyl, $C_2$-$C_6$ alkyl, wherein said alkyl is optionally substituted by carboxylic acid, sulfonic acid, amino, or halogen; and $R_{30}$, $R_{31}$, $R_{33}$ and $R_{34}$ are independently selected from the group consisting of hydrogen, F, Cl, Br, I, sulfonic acid, carboxylic acid, CN, nitro, hydroxy, azido, amino, hydrazino, or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_7$-$C_{18}$ arylcarboxamido, wherein said alkyl or aryl portions of said $R_{30}$, $R_{31}$, $R_{33}$ and $R_{34}$ are optionally substituted one or more times by substituents selected from the group consisting of F, Cl, Br, I, hydroxy, carboxylic acid, a carboxylic acid ester of a $C_1$-$C_6$ alcohol, sulfonic acid, amino, $C_1$-$C_6$ alkylamino, $C_1$-$C_6$ dialkylamino and $C_2$-$C_6$ alkoxy; or a pair of adjacent $R_{30}$ and $R_{31}$ or $R_{33}$ and $R_{34}$ substituents when taken in combination, form a fused 6-membered aromatic ring that is optionally further substituted by carboxylic acid.

In one illustrative aspect, compounds of formulae (X) are described wherein $R_3$, $R_4$, $R_{43}$, and $R_{44}$ are each methyl. In another illustrative aspect, compounds of formulae (X) are described wherein each of $R_1$ and $R_{41}$ is independently H or sulfonic acid. In another illustrative aspect, compounds of formulae (X) are described wherein $R_6$ and $R_{46}$ are H. In another illustrative aspect, compounds of formulae (X) are described wherein the compounds are substituted one or more times by sulfonic acid. In another illustrative aspect, compounds of formulae (X) are described wherein $R_3$, $R_4$, $R_5$, $R_{43}$, $R_{44}$, and $R_{45}$ are independently methyl or ethyl. In another illustrative aspect, compounds of formulae (X) are described wherein $R_{30}$ is sulfonic acid or carboxylic acid. In another illustrative aspect, compounds of formulae (X) are described wherein one of $R_{32}$ and $R_{33}$ is H, F, or Cl. In another illustrative aspect, compounds of formulae (X) are described wherein both X and X' are S.

In another illustrative embodiment, a fluorescent-HAP stain (compound) having the structural formula (XI)

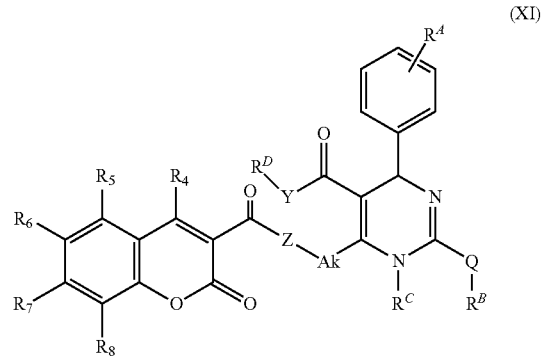

or a salt thereof is described, wherein: Q is $Ak_1$ or $Ar^1$, and $R^C$, $R^D$, $Ar^1$, Z, Ak, $Ak_1$, $R^A$, and $R^B$ are as defined herein, $R_4$ is H, OH, CN, $C_1$-$C_{18}$ alkyl, $C_1$-$C_{18}$ perfluoroalkyl, sulfomethyl, biologically compatible salt of sulfomethyl, halomethyl, or aryl;

$R_5$ is H or $C_1$-$C_6$ alkoxy;

$R_6$ is H, methyl, halogen, or $SO_3X$;

$R_7$ is H or $NR^1R^2$; wherein $R_1$ and $R_2$ are independently H, $C_1$-$C_{18}$ alkyl, $C_6$-$C_{18}$ aryl, $C_1$-$C_{18}$ alkanoyl, $C_7$-$C_{18}$ arylalkanoyl;

or $R_1$ in combination with $R_2$ forms a saturated 5- or 6-membered heterocycle that is a piperidine, a morpholine, a pyrrolidine or a piperazine;

or $R_1$ is a 2-nitrobenzyloxycarbonyl of the formula

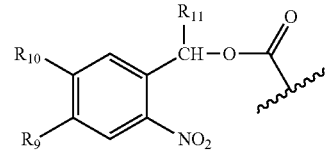

wherein $R_9$ and $R_{10}$ are H, $C_1$-$C_6$ alkoxy, or $R_9$ and $R_{10}$ taken in combination are —O—$CH_2$—O—; and $R_{11}$ is H, $CH_3$, a carboxylic acid or a biologically compatible salt of a carboxylic acid;

$R_8$ is H, halogen, $SO_3X$, $C_1$-$C_6$ alkoxy or $C_1$-$C_6$ alkyl; and

X is H, or a biologically compatible cation.

In one illustrative aspect, compounds of formulae (XI) are described wherein at least one of $R_3$, $R_6$ or $R_8$ is $SO_3X$. In another illustrative aspect, compounds of formulae (XI) are described wherein $R_4$ is sulfomethyl, halomethyl, $C_1$-$C_{18}$ alkyl or $C_1$-$C_{18}$ perfluoroalkyl. In another illustrative aspect, compounds of formulae (XI) are described wherein $R_7$ is $NR^1R^2$ and $R_1$ and $R_2$ are independently H or $C_1$-$C_{18}$ alkyl. In another illustrative aspect, compounds of formulae (XI) are described wherein $R_7$ is $NR^1R^2$, where $R_2$ is H and $R_1$ is a 2-nitrobenzyloxycarbonyl of the formula

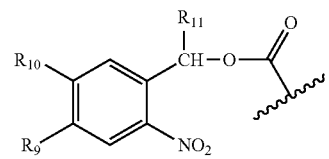

wherein $R_9$ and $R_{10}$ are H, $C_1$-$C_6$ alkoxy, or $R_9$ and $R_{10}$ taken in combination are —O—CH$_2$—O—; and $R_{11}$ is H, CH$_3$, a carboxylic acid or a biologically compatible salt of a carboxylic acid. In another illustrative aspect, compounds of formulae (XI) are described wherein $R_4$ is CH$_3$. In another illustrative aspect, compounds of formulae (XI) are described wherein $R_7$ is NH$_2$. In another illustrative aspect, compounds of formulae (XI) are described wherein $R_8$ is H.

In another embodiment, the compounds, compositions, methods or kits of any one of the preceding embodiments are described wherein Q is $Ar^1$.

Several illustrative embodiments of the invention are described by the following clauses:

1. A compound having the formula (I)

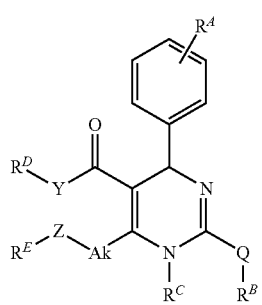

(I)

or a salt thereof, wherein:
Q is $Ar^1$ or $Ak_1$;
$Ar^1$ is aryl or heteroaryl
$R^C$ is hydrogen;
Ak and $Ak_1$ are independently $C_1$-$C_6$ alkylene;
Z is

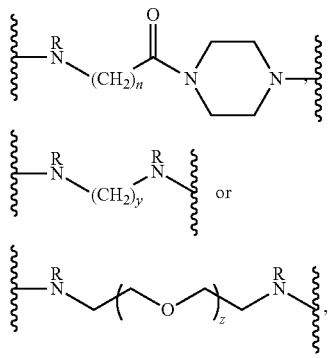

where n is 1, 2, 3, 4, 5, or 6; y is 6, 7, 8, 9, 10, 11 or 12; z is 1, 2, 3, or 4; and R is H or alkyl;

$R^D$ is selected from the group consisting of alkyl, heteroalkyl, alkenyl, and alkynyl, each of which is optionally substituted;
$R^E$ is a FLUOROPHORE;
Y is O, S, or HN;
$R^A$ represents from 0 to 3 substituents independently in each instance, halo or selected from the group consisting of alkyl, heteroalkyl, aryl, heteroaryl, amino and derivatives thereof, and hydroxyl and derivatives thereof, each of which is optionally substituted; and
$R^B$ represents from 0 to 3 substituents independently in each instance, halogen or selected from the group consisting of alkyl, heteroalkyl, aryl, heteroaryl, amino and derivatives thereof, and hydroxyl and derivatives thereof, each of which is optionally substituted.

2. The compound of the preceding clause wherein $R^A$ represents 2-chloro-4-fluoro.

3. The compound of any one of the preceding clauses wherein Q is $Ar^1$ where $Ar^1$ is 2-thiazolyl, 2-thienyl, 2-furanyl, 2-(1-methyl)imidazolyl, 2-pyrimidinyl, 2-naphthyl, 2-pyrrolidinyl, phenyl, 2-pyridyl, 3-pyridyl, or 4-pyridyl.

3.1. The compound of any one of the preceding clauses wherein Q is $Ar^1$ where $Ar^1$ is phenyl, 2-pyridyl, 3-pyridyl, or 4-pyridyl.

3.2. The compound of any one of the preceding clauses wherein Q is $Ar^1$ where $Ar^1$ is 2-pyridyl.

3.3. The compound of any one of the preceding clauses wherein Q is $Ak_1$ where $Ak_1$ is $C_1$-$C_4$, or $C_1$-$C_3$, or $C_1$-$C_2$ alkylene.

3.4. The compound of any one of the preceding clauses wherein Q is $Ak_1$ where $Ak_1$ is CH$_2$.

4. The compound of any one of clauses 1 to 3.4 wherein Q is $Ar^1$ and $R^B$ is absent.

5. The compound of any one of clauses 1 to 4 wherein Y is O.

6. The compound of any one of clauses 1 to 5 wherein $R^D$ is methyl.

7. The compound of any one of clauses 1 to 6 wherein $R^E$ is

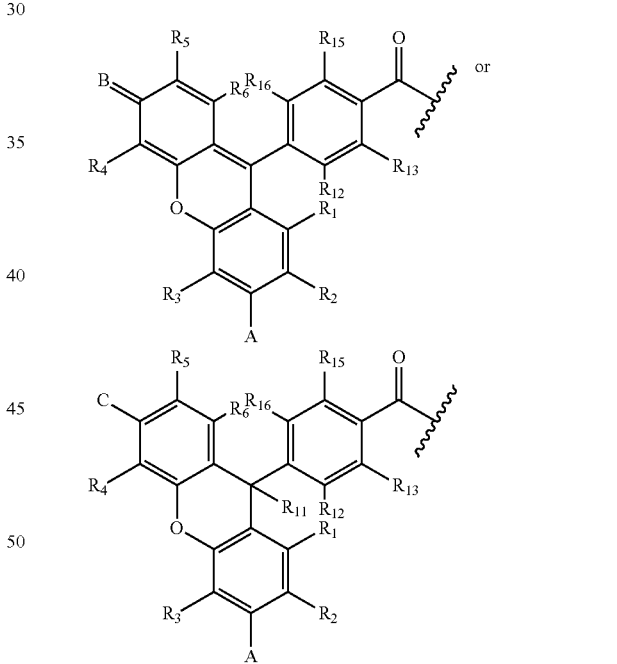

wherein
$R_2$, $R_3$, $R_4$ and $R_5$ are independently H, F, Cl, Br, I, CN; or $C_1$-$C_{18}$ alkyl, or $C_1$-$C_{18}$ alkoxy, where each alkyl or alkoxy is optionally further substituted by F, Cl, Br, I, a carboxylic acid, a salt of carboxylic acid, or a carboxylic acid ester of a $C_1$-$C_6$ alcohol; or —SO$_3$X where X is H or a counterion;
$R_1$ and $R_6$ are H; or $R_1$ taken in combination with $R_2$ or $R_5$ taken in combination with $R_6$ or both, form a fused aromatic six-membered ring that is optionally substituted one or more times by —SO$_3$X;

A is $NR^8R^9$; where $R^8$ and $R^9$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl; or $R_8$ in combination with $R_9$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$-$C_6$ alkyl;

or $R_8$ in combination with $R_2$, or $R_9$ in combination with $R_3$, or both, form a 5- or 6-membered ring that is saturated or unsaturated, and is optionally substituted by one or more $C_1$-$C_6$ alkyls or —$CH_2SO_3X$ moieties;

C is $OR_{17}$ or $NR^{18}R^{19}$, where $R_{17}$ is H, or $C_1$-$C_{18}$ alkyl;

$R^{18}$ and $R^{19}$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl; or $R_{18}$ in combination with $R_{19}$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$-$C_6$ alkyl;

or $R^{18}$ in combination with $R_4$, or $R^{19}$ in combination with $R_5$, or both, form a 5- or 6-membered ring that is saturated or unsaturated, and is optionally substituted by one or more $C_1$-$C_6$ alkyls or —$CH_2SO_3X$ moieties;

B is O or $N^+R^{18}R^{19}$;

$R_{12}$, $R_{13}$, $R_{15}$, and $R_{16}$ are independently H, F, Cl, Br, I, —$SO_3X$, a carboxylic acid, a salt of carboxylic acid, CN, nitro, hydroxy, azido, amino, hydrazino; or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_6$-$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$-$C_6$ alcohol, —$SO_3X$, amino, alkylamino, dialkylamino or alkoxy, the alkyl portions of each having 1-6 carbons; or one pair of adjacent substituents $R_{12}$ and $R_{13}$ or $R_{15}$ and $R_{16}$, when taken in combination, form a fused 6-membered aromatic ring that is optionally further substituted by carboxylic acid, or a salt of carboxylic acid; and $R_{11}$ is H, hydroxy, CN or a $C_1$-$C_6$ alkoxy; or $R_{11}$ in combination with $R_{12}$ forms a 5- or 6-membered spirolactone ring or a 5- or 6-membered spirosultone ring that is optionally and independently substituted by H, F or $CH_3$.

8. The compound of clause 1 having the formula

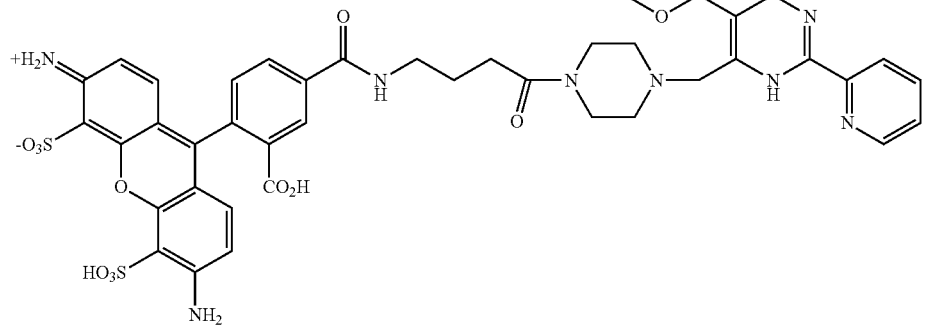

or a salt thereof.

9. The compound of any one of clauses 1 to 6 wherein $R^E$ is

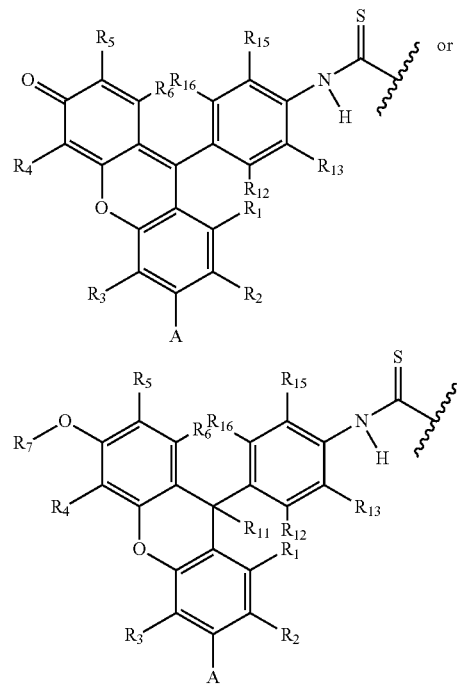

wherein

R₁ and R₆ are independently H, F, Cl, Br, I, $C_1$-$C_{18}$ alkyl or $C_1$-$C_{18}$ alkoxy;

$R_2$, $R_3$, $R_4$ and $R_5$ are independently H, F, Cl, Br, I, CN; or $C_1$-$C_{18}$ alkyl, $C_1$-$C_{18}$ alkoxy or $C_1$-$C_{18}$ alkylthio, where each alkyl, alkoxy or alkylthio is optionally further substituted by F, Cl, Br, I, sulfonic acid, salt of sulfonic acid, carboxylic acid, a salt of carboxylic acid, a carboxylic acid ester of a $C_1$-$C_6$ alkyl, a carboxylic acid ester of —$CH_2$—O—(C=O)—$R_{18}$ where $R_{18}$ is a $C_1$-$C_4$ alkyl; or amino, alkylamino, dialkylamino, or alkoxy, the alkyl portions of which independently have 1-6 carbons; or one or both of $R_3$ and $R_4$ are —$CH_2N(CH_2COOR_{17})_2$, where $R_{17}$ is H, a biologically compatible counterion, a linear or branched alkyl having 1-6 carbons, or —$CH_2$—O—(C=O)—$R_{18}$;

A is $OR_7$ or $NR^8R^9$, where each $R_7$ is independently H, $C_1$-$C_{18}$ alkyl, a $C_1$-$C_{18}$ acyl wherein each alkyl group independently has 1-6 carbons and is optionally substituted by amino, hydroxy, carboxylic acid, a salt of carboxylic acid, a carboxylic acid ester of a $C_1$-$C_6$ alkyl, a carboxylic acid ester of —$CH_2$—O—(C=O)—$R_{18}$; or a trialkylsilyl wherein each alkyl group independently has 1-6 carbons;

$R^8$ and $R^9$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, a salt of $C_1$-$C_6$ sulfoalkyl, or $C_1$-$C_{18}$ acyl wherein the alkyl portions are optionally substituted by amino, hydroxy, carboxylic acid, a salt of carboxylic acid, a carboxylic acid ester of a $C_1$-$C_6$ alkyl, a carboxylic acid ester of —$CH_2$—O—(C=O)—$R_{18}$; or $R^8$ in combination with $R_2$, or $R^9$ in combination with $R_3$, or both, form a saturated 5- or 6-membered ring that is optionally substituted by one or more methyls; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$-$C_6$ alkyl, or a carboxylic acid ester of —$CH_2$—O—(C=O)—$R_{18}$;

$R_{12}$, $R_{13}$, $R_{15}$ and $R_{16}$ are independently H, F, Cl, Br, I; or sulfonic acid, salt of sulfonic acid, carboxylic acid, a salt of carboxylic acid, a carboxylic acid ester of a $C_1$-$C_6$ alkyl, a carboxylic acid ester of —$CH_2$—O—(C=O)—$R_{18}$, CN, nitro, hydroxy, azido, amino, hydrazino; or $C_1$-$C_{18}$ alkyl, $C_1$-$C_{18}$ alkoxy, $C_1$-$C_{18}$ alkylthio, $C_1$-$C_{18}$ alkylamino, $C_1$-$C_{18}$ alkylester, $C_1$-$C_{18}$ alkylamido or $C_1$-$C_{18}$ arylamido, the alkyl or aryl portions of which are optionally substituted one or more times by F, Cl, Br, I, hydroxy, carboxylic acid, a salt of carboxylic acid, a carboxylic acid ester of a $C_1$-$C_6$ alkyl, a carboxylic acid ester of —$CH_2$—O—(C=O)—$R_{18}$, sulfonic acid, salt of sulfonic acid, amino, alkylamino, dialkylamino or alkoxy, the alkyl portions of each having 1-6 carbons; or one pair of adjacent substituents $R_{12}$ and $R_{13}$ or $R_{15}$ and $R_{16}$, when taken in combination, form a fused 6-membered aromatic ring that is optionally further substituted by carboxylic acid, a salt of carboxylic acid, a carboxylic acid ester of a $C_1$-$C_6$ alkyl, a carboxylic acid ester of —$CH_2$—O—(C=O)—$R_{18}$; and $R_{11}$ is H, hydroxy, CN or a $C_1$-$C_6$ alkoxy; or $R_{11}$ in combination with $R_{12}$ forms a 5- or 6-membered spirolactone ring or a 5- or 6-membered spirosultone ring that is optionally and independently substituted by H, F or $CH_3$.

10. The compound of clause 1 having the formula

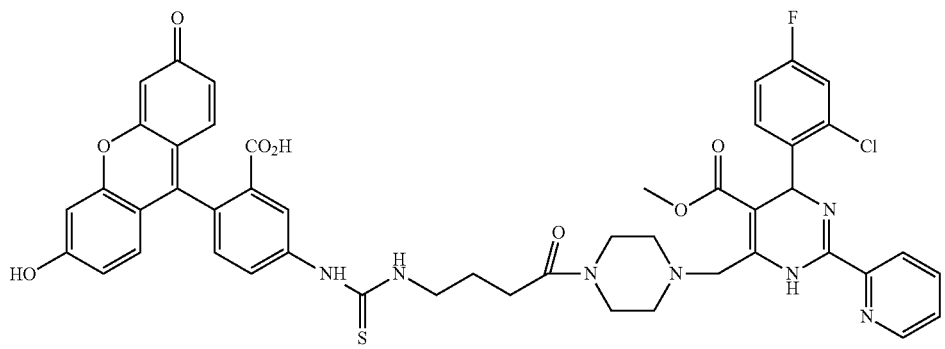 [SMILES: COC(=O)C1=C(CN2CCN(C(=O)CCCNC(=S)Nc3ccc(-c4c5ccc(=O)cc-5oc5cc(O)ccc45)c(C(=O)O)c3)CC2)NC(c2ccccn2)=NC1c1ccc(F)cc1Cl]

or a salt thereof.

11. The compound of any one of clauses 1 to 6 wherein $R^E$ is

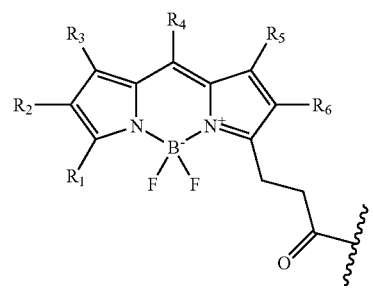

wherein $R_1$, $R_2$, $R_3$, $R_4$, $R_5$, and $R_6$ are each independently H, halogen, alkyl, cycloalkyl, aryl, arylalkyl, acyl or sulfo.

12. The compound of clause 1 having the formula

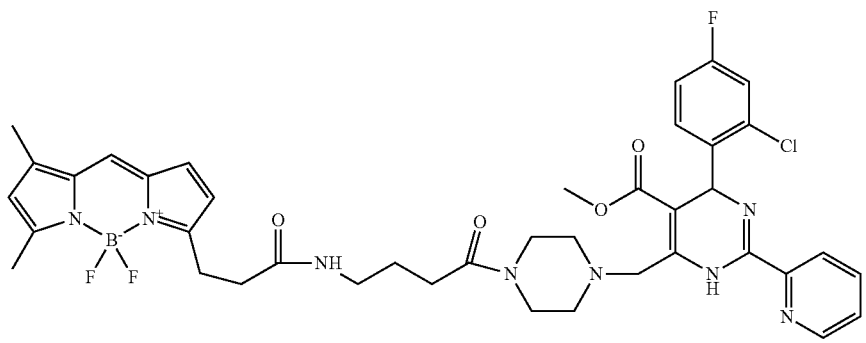 [SMILES: COC(=O)C1=C(CN2CCN(C(=O)CCCNC(=O)CCC3=[N+]4C(=Cc5c(C)cc(C)n5[B-]4(F)F)C=C3)CC2)NC(c2ccccn2)=NC1c1ccc(F)cc1Cl]

or a salt thereof.

13. The compound of any one of clauses 1 to 6 wherein $R^E$ is

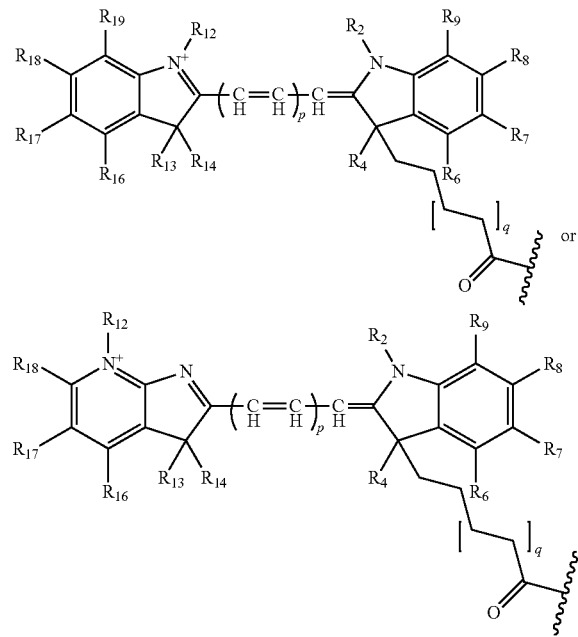

wherein $R_4$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by substituents selected from the group consisting of F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium;

$R_2$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, $C_2$-$C_{12}$ dialkylamino, or $C_3$-$C_{18}$ trialkylammonium;

$R_6$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_7$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_8$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_9$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{16}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{17}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{18}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{19}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

or a member independently selected from
$R_6$ in combination with $R_7$;
$R_7$ in combination with $R_8$;
$R_8$ in combination with $R_9$;
$R_{16}$ in combination with $R_{17}$;
$R_{17}$ in combination with $R_{18}$; and
$R_{18}$ in combination with $R_{19}$ together with the atoms to which they are joined, form an aromatic ring comprising —CH— or —CR$^1$— wherein $R^1$ is amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, wherein each alkyl portion of which is optionally substituted by substituents selected from the group consisting of carboxy, sulfo, amino, and hydroxyl;

p is 1, 2 or 3;

q is 0, 1, 2 or 3;

$R_{12}$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, $C_2$-$C_{12}$ dialkylamino, or $C_3$-$C_{18}$ trialkylammonium;

$R_{13}$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium;

$R_{14}$ is $C_1$-$C_{22}$ alkyl or $C_7$-$C_{22}$ arylalkyl, each alkyl portion of which optionally incorporates up to six hetero atoms, selected from N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium;

or $R_{13}$ and $R_{14}$ taken in combination complete a five- or six-membered saturated or unsaturated ring that is optionally substituted; and wherein sulfo is sulfonic acid or sulfonate.

14. The compound of any one of clauses 1 to 6 wherein $R^E$ is

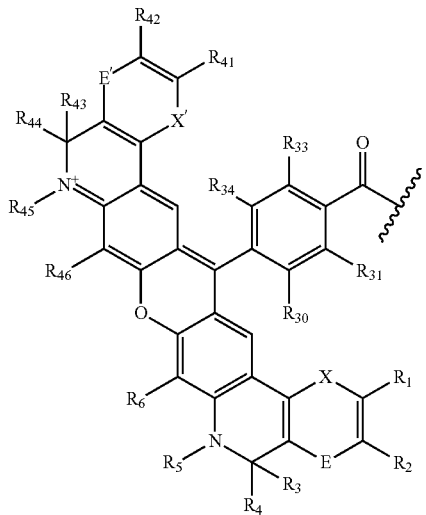

wherein $R_1$, $R_2$, $R_6$, $R_{41}$, $R_{42}$, and $R_{46}$ are independently selected from the group consisting of hydrogen, cyano, halogen, carboxylic acid, sulfonic acid $C_1$-$C_6$ alkyl, $C_1$-$C_6$ alkoxy, aryl, heteroaryl, wherein said alkyl or alkoxy is optionally substituted by carboxylic acid, sulfonic acid, or halogen and said aryl or heteroaryl is optionally substituted one or more times by $C_1$-$C_6$ alkyl, $C_1$-$C_6$ perfluoroalkyl, cyano, halogen, azido, carboxylic acid, sulfonic acid, or halomethyl;

or $R_1$ in combination with $R_2$, or $R_{41}$ in combination with $R_{42}$, or both, forms a fused aromatic or heteroaromatic ring that is optionally sulfonated one or more times;

$R_3$, $R_4$, $R_{43}$, and $R_{44}$ are independently selected from the group consisting of hydrogen, $C_1$-$C_6$ alkyl, an aromatic or heteroaromatic ring, wherein said alkyl is optionally substituted by carboxylic acid, sulfonic acid, amino, hydroxy, or halogen and said aromatic or heteroaromatic ring that is optionally substituted one or more times by $C_1$-$C_6$ alkyl, $C_1$-$C_6$ alkoxy, $C_1$-$C_6$ perfluoroalkyl, cyano, halogen, carboxylic acid, sulfonic acid, or halomethyl;

or $R_2$ in combination with $R_3$, $R_{42}$ in combination with $R_{43}$, or $R_3$ in combination with $R_4$, or $R_{43}$ in combination with $R_{44}$, or any combination thereof, forms a 5- or 6-membered alicyclic ring;

$R_5$ and $R_{45}$ are independently selected from the group consisting of hydrogen, methyl, carboxymethyl, $C_2$-$C_6$ alkyl, or heteroaryl, wherein said alkyl is optionally substituted by carboxylic acid, sulfonic acid, amino, or halogen and said aryl or heteroaryl is optionally substituted one or more times by $C_1$-$C_6$ alkyl, $C_1$-$C_6$ perfluoroalkyl, cyano, halogen, carboxylic acid, sulfonic acid, or halomethyl;

or $R_4$ in combination with $R_5$, or $R_5$ in combination with $R_6$, or $R_{44}$ in combination with $R_{45}$, or $R_{45}$ in combination with $R_{46}$, or any combination thereof, forms a 5- or 6-membered alicyclic ring;

wherein E, E', X' and X is O, S, or $NR^8$ provided that E and X or E' and X' are not both present;

wherein $R^8$ is independently selected from the group consisting of hydrogen, methyl, carboxymethyl, $C_2$-$C_6$ alkyl, wherein said alkyl is optionally substituted by carboxylic acid, sulfonic acid, amino, or halogen; and $R_{30}$, $R_{31}$, $R_{33}$ and $R_{34}$ are independently selected from the group consisting of hydrogen, F, Cl, Br, I, sulfonic acid, carboxylic acid, CN, nitro, hydroxy, azido, amino, hydrazino, or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_7$-$C_{18}$ arylcarboxamido, wherein said alkyl or aryl portions of said $R_{30}$, $R_{31}$, $R_{33}$ and $R_{34}$ are optionally substituted one or more times by substituents selected from the group consisting of F, Cl, Br, I, hydroxy, carboxylic acid, a carboxylic acid ester of a $C_1$-$C_6$ alcohol, sulfonic acid, amino, $C_1$-$C_6$ alkylamino, $C_1$-$C_6$ dialkylamino and $C_2$-$C_6$ alkoxy; or a pair of adjacent $R_{30}$ and $R_{31}$ or $R_{33}$ and $R_{34}$ substituents when taken in combination, form a fused 6-membered aromatic ring that is optionally further substituted by carboxylic acid.

15. The compound of any one of clauses 1 to 6 wherein $R^E$ is

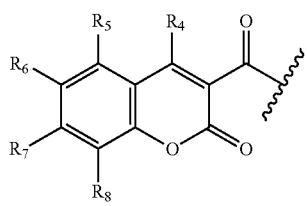

wherein $R_4$ is H, OH, CN, $C_1$-$C_{18}$ alkyl, $C_1$-$C_{18}$ perfluoroalkyl, sulfomethyl, biologically compatible salt of sulfomethyl, halomethyl, or aryl;

$R_5$ is H or $C_1$-$C_6$ alkoxy;

$R_6$ is H, methyl, halogen, or $SO_3X$;

$R_7$ is H or $NR^1R^2$; wherein $R_1$ and $R_2$ are independently H, $C_1$-$C_{18}$ alkyl, $C_6$-$C_{18}$ aryl, $C_1$-$C_{18}$ alkanoyl, $C_7$-$C_{18}$ arylalkanoyl;

or $R_1$ in combination with $R_2$ forms a saturated 5- or 6-membered heterocycle that is a piperidine, a morpholine, a pyrrolidine or a piperazine;

or $R_1$ is a 2-nitrobenzyloxycarbonyl of the formula

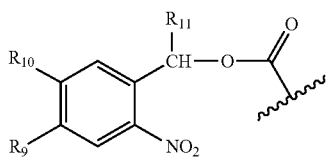

wherein $R_9$ and $R_{10}$ are H, $C_1$-$C_6$ alkoxy, or $R_9$ and $R_{10}$ taken in combination are —O—$CH_2$—O—; and $R_{11}$ is H, $CH_3$, a carboxylic acid or a biologically compatible salt of a carboxylic acid;

$R_8$ is H, halogen, $SO_3X$, $C_1$-$C_6$ alkoxy or $C_1$-$C_6$ alkyl; and X is H, or a biologically compatible cation.

16. A composition comprising one or more compounds of any one of clauses 1 to 15 in an amount effective for diagnosing, detecting, tracking, and/or competitively binding to HBV.

17. The composition of clause 16 further comprising one or more carriers, diluents, or excipients, or a combination thereof.

18. A method for detecting, diagnosing, and/or tracking HBV in cells and tissue, the method comprising the steps of:

a) incubating a mixture of cells and one or more compounds of any one of clauses 1 to 15 or the composition of clause 16 or 17 in an amount effective for diagnosing, detecting, and/or tracking HBV;

b) washing away any excess of said one or more compounds;

c) providing a stimulus to the mixture to elicit a fluorescent signal; and d) analyzing the stimulated mixture.

19. The method of clause 18, wherein the cells are from tissue culture, fresh biopsy, fixed section, or other source.

20. The method of clause 18 or 19, wherein analyzing is accomplished by examining bulk fluorescence, by examining individual cells by fluorescence microscopy, by cell sorter, or by another mechanism.

21. A method for detecting, diagnosing, and/or tracking HBV cores in solution, the method comprising the steps of:

a) incubating a solution comprising clarified serum, growth medium, or other liquid to be tested and one or more compounds of any one of clauses 1 to 15 or the composition of clause 16 or 17 in an amount effective for diagnosing, detecting, and/or tracking HBV;

b) adjusting ionic strength, if necessary, to induce e-antigen assembly for the purpose of detecting said assembly;

c) separating unbound said one or more compounds from said one or more compounds bound to HBV cores to create an unbound phase and a bound phase, respectively; and d) analyzing the fluorescence associated with the unbound and bound phases.

22. The method of clause 21, wherein separating unbound compounds from compounds bound to HBV cores is accomplished by gel permeation chromatography, ultrafiltration, centrifugation, or other technique.

23. A method for conducting anti-HBV drug discovery, the method comprising the steps of:

a) incubating a mixture of an anti-HBV drug candidate, pre-assembled HBV cores and one or more compounds of any one of clauses 1 to 15 or the composition of clause 16 or 17 in an amount effective for detecting competitive binding by the anti-HBV drug candidate to the HAP pocket of HBV;

b) measuring a change in the fluorescence of said one or more compounds; and c) analyzing the mixture for competitive binding by the anti-HBV drug candidate to the HAP pocket of HBV.

24. A method for conducting anti-HBV drug discovery, the method comprising the steps of:

a) incubating a mixture of an anti-HBV drug candidate, pre-assembled HBV cores and one or more compounds of any one of clauses 1 to 15 or the composition of clause 16 or 17 in an amount effective for detecting competitive binding by the anti-HBV drug candidate to the HAP pocket of HBV;

b) separating unbound said anti-HBV drug candidate and unbound said one or more compounds from said anti-HBV drug candidate and said one or more compounds bound to HBV cores to create an unbound phase and a bound phase, respectively;

c) measuring the fluorescence associated with the unbound and bound phases; and d) analyzing the mixture for competitive binding by the anti-HBV drug candidate to the HAP pocket of HBV.

25. The method of clause 24, wherein separating unbound compounds from compounds bound to HBV cores is accomplished by gel permeation chromatography, ultrafiltration, centrifugation, or other technique.

26. A kit for detecting, diagnosing, and/or tracking HBV, and/or identifying compounds that competitively bind to the HAP pocket of HBV, the kit comprising:

a) one or more compounds of any one of clauses 1 to 15 or the composition of clause 16 or 17; and b) a solvent.

27. A process for preparing a compound having the structural formula (I)

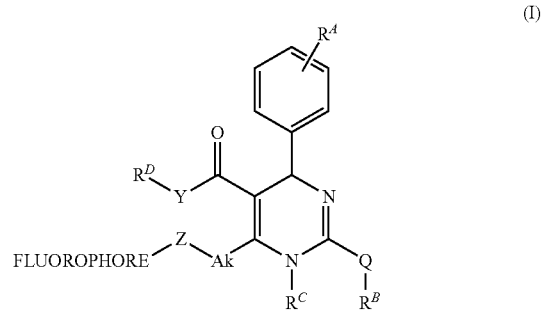

or a salt thereof, the process comprising:
(a) reacting a compound of structural formula

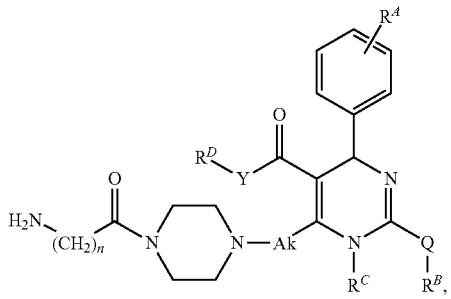
(II)

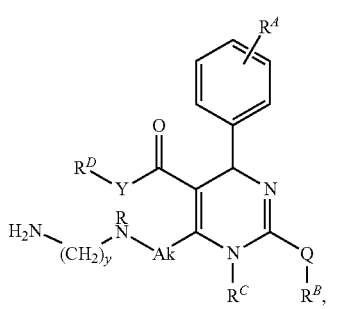
(II')

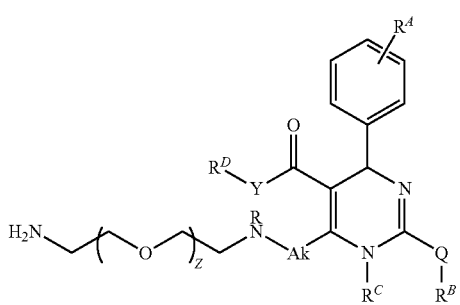
(II'')

with a suitably activated FLUOROPHORE, wherein:

Q, $R^C$, $R^D$, $Ar^1$, Z, Ak, $Ak_1$, R, $R^A$, $R^B$, n, y and z are as defined in clause 1.

28. The process of clause 27 wherein the suitably activated FLUOROPHORE is

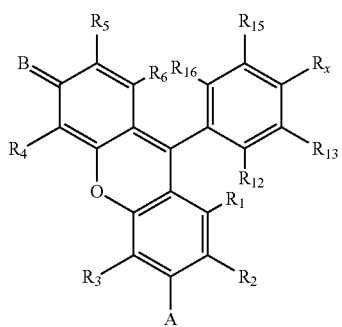

or

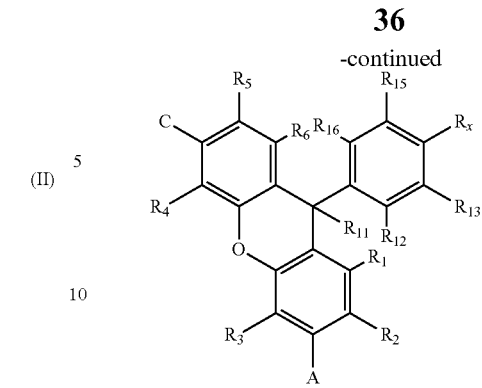

wherein $R_2$, $R_3$, $R_4$ and $R_5$ are independently H, F, Cl, Br, I, CN; or $C_1$-$C_{18}$ alkyl, or $C_1$-$C_{18}$ alkoxy, where each alkyl or alkoxy is optionally further substituted by F, Cl, Br, I, a carboxylic acid, a salt of carboxylic acid, or a carboxylic acid ester of a $C_1$-$C_6$ alcohol; or —$SO_3X$ where X is H or a counterion;

$R_1$ and $R_6$ are H; or $R_1$ taken in combination with $R_2$ or $R_5$ taken in combination with $R_6$ or both, form a fused aromatic six-membered ring that is optionally substituted one or more times by —$SO_3X$;

A is $NR^8R^9$;

where $R^8$ and $R^9$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl; or $R_8$ in combination with $R_9$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$-$C_6$ alkyl;

or $R_8$ in combination with $R_2$, or $R_9$ in combination with $R_3$, or both, form a 5- or 6-membered ring that is saturated or unsaturated, and is optionally substituted by one or more $C_1$-$C_6$ alkyls or —$CH_2SO_3X$ moieties;

C is $OR_{17}$ or $NR^{18}R^{19}$, where $R_{17}$ is H, or $C_1$-$C_{18}$ alkyl; $R^{18}$ and $R^{19}$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl; or $R_{18}$ in combination with $R_{19}$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$-$C_6$ alkyl;

or $R^{18}$ in combination with $R_4$, or $R^{19}$ in combination with $R_5$, or both, form a 5- or 6-membered ring that is saturated or unsaturated, and is optionally substituted by one or more $C_1$-$C_6$ alkyls or —$CH_2SO_3X$ moieties;

B is O or $N^+R^{18}R^{19}$;

$R_{12}$, $R_{13}$, $R_{15}$, and $R_{16}$ are independently H, F, Cl, Br, I, —$SO_3X$, a carboxylic acid, a salt of carboxylic acid, CN, nitro, hydroxy, azido, amino, hydrazino; or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_6$-$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$-$C_6$ alcohol, —$SO_3X$, amino, alkylamino, dialkylamino or alkoxy, the alkyl portions of each having 1-6 carbons; or one pair of adjacent substituents $R_{12}$ and $R_{13}$ or $R_{15}$ and $R_{16}$, when taken in combination, form a fused 6-membered aromatic ring that is optionally further substituted by carboxylic acid, or a salt of carboxylic acid;

$R_{11}$ is H, hydroxy, CN or a $C_1$-$C_6$ alkoxy; or $R_{11}$ in combination with $R_{12}$ forms a 5- or 6-membered spirolactone ring or a 5- or 6-membered spirosultone ring that is optionally and independently substituted by H, F or $CH_3$; and $R_x$ is a reactive group selected from the group consisting of an activated ester of a carboxylic acid, an acyl azide, an aldehyde, an alkyl halide, an anhydride, a sulfonyl halide, a malemide, an isocyanate, and an isothiocyanate.

29. The process of clause 28 wherein the reactive group, Rx, is an activated ester of a carboxylic acid.

30. The process of clause 29 wherein the activated ester is a tetrafluorophenyl ester.

31. The process of clause 27 wherein the suitably activated FLUOROPHORE is

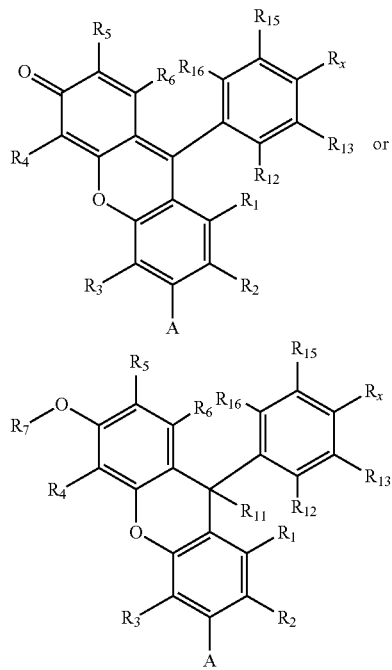

wherein $R_1$ and $R_6$ are independently H, F, Cl, Br, I, $C_1$-$C_{18}$ alkyl or $C_1$-$C_{18}$ alkoxy;

$R_2$, $R_3$, $R_4$ and $R_5$ are independently H, F, Cl, Br, I, CN; or $C_1$-$C_{18}$ alkyl, $C_1$-$C_{18}$ alkoxy or $C_1$-$C_{18}$ alkylthio, where each alkyl, alkoxy or alkylthio is optionally further substituted by F, Cl, Br, I, sulfonic acid, salt of sulfonic acid, carboxylic acid, a salt of carboxylic acid, a carboxylic acid ester of a $C_1$-$C_6$ alkyl, a carboxylic acid ester of —$CH_2$—O—(C=O)—$R_{18}$ where $R_{18}$ is a $C_1$-$C_4$ alkyl; or amino, alkylamino, dialkylamino, or alkoxy, the alkyl portions of which independently have 1-6 carbons; or one or both of $R_3$ and $R_4$ are —$CH_2N(CH_2COOR_{17})_2$, where $R_{17}$ is H, a biologically compatible counterion, a linear or branched alkyl having 1-6 carbons, or —$CH_2$—O—(C=O)—$R_{18}$;

A is $OR_7$ or $NR^8R^9$, where each $R_7$ is independently H, $C_1$-$C_{18}$ alkyl, a $C_1$-$C_{18}$ acyl wherein each alkyl group independently has 1-6 carbons and is optionally substituted by amino, hydroxy, carboxylic acid, a salt of carboxylic acid, a carboxylic acid ester of a $C_1$-$C_6$ alkyl, a carboxylic acid ester of —$CH_2$—O—(C=O)—$R_{18}$; or a trialkylsilyl wherein each alkyl group independently has 1-6 carbons;

$R^8$ and $R^9$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, a salt of $C_1$-$C_6$ sulfoalkyl, or $C_1$-$C_{18}$ acyl wherein the alkyl portions are optionally substituted by amino, hydroxy, carboxylic acid, a salt of carboxylic acid, a carboxylic acid ester of a $C_1$-$C_6$ alkyl, a carboxylic acid ester of —$CH_2$—O—(C=O)—$R_{18}$; or $R^8$ in combination with $R_2$, or $R^9$ in combination with $R_3$, or both, form a saturated 5- or 6-membered ring that is optionally substituted by one or more methyls; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$-$C_6$ alkyl, or a carboxylic acid ester of —$CH_2$—O—(C=O)—$R_{18}$;

$R_{12}$, $R_{13}$, $R_{15}$ and $R_{16}$ are independently H, F, Cl, Br, I; or sulfonic acid, salt of sulfonic acid, carboxylic acid, a salt of carboxylic acid, a carboxylic acid ester of a $C_1$-$C_6$ alkyl, a carboxylic acid ester of —$CH_2$—O—(C=O)—$R_{18}$, CN, nitro, hydroxy, azido, amino, hydrazino; or $C_1$-$C_{18}$ alkyl, $C_1$-$C_{18}$ alkoxy, $C_1$-$C_{18}$ alkylthio, $C_1$-$C_{18}$ alkylamino, $C_1$-$C_{18}$ alkylester, $C_1$-$C_{18}$ alkylamido or $C_1$-$C_{18}$ arylamido, the alkyl or aryl portions of which are optionally substituted one or more times by F, Cl, Br, I, hydroxy, carboxylic acid, a salt of carboxylic acid, a carboxylic acid ester of a $C_1$-$C_6$ alkyl, a carboxylic acid ester of —$CH_2$—O—(C=O)—$R_{18}$, sulfonic acid, salt of sulfonic acid, amino, alkylamino, dialkylamino or alkoxy, the alkyl portions of each having 1-6 carbons; or one pair of adjacent substituents $R_{12}$ and $R_{13}$ or $R_{15}$ and $R_{16}$, when taken in combination, form a fused 6-membered aromatic ring that is optionally further substituted by carboxylic acid, a salt of carboxylic acid, a carboxylic acid ester of a $C_1$-$C_6$ alkyl, a carboxylic acid ester of —$CH_2$—O—(C=O)—$R_{18}$;

$R_{11}$ is H, hydroxy, CN or a $C_1$-$C_6$ alkoxy; or $R_{11}$ in combination with $R_{12}$ forms a 5- or 6-membered spirolactone ring or a 5- or 6-membered spirosultone ring that is optionally and independently substituted by H, F or $CH_3$; and $R_x$ is a reactive group selected from the group consisting of an activated ester of a carboxylic acid, an acyl azide, an aldehyde, an alkyl halide, an anhydride, a sulfonyl halide, a malemide, an isocyanate, and an isothiocyanate.

32. The process of clause 31 wherein the reactive group, Rx, is an isothiocyanate.

33. The process of clause 27 wherein the suitably activated FLUOROPHORE is

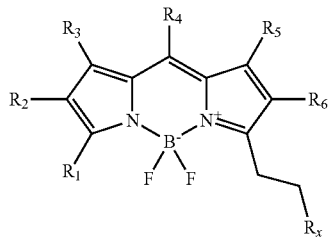

wherein

R$_1$, R$_2$, R$_3$, R$_4$, R$_5$, and R$_6$ are each independently H, halogen, alkyl, cycloalkyl, aryl, arylalkyl, acyl or sulfo; and R$_x$ is a reactive group selected from the group consisting of an activated ester of a carboxylic acid, an acyl azide, an aldehyde, an alkyl halide, an anhydride, a sulfonyl halide, a malemide, an isocyanate, and an isothiocyanate.

34. The process of clause 33 wherein the reactive group, Rx, is an activated ester of a carboxylic acid.

35. The process of clause 34 wherein the activated ester is a succinimidyl ester.

36. The process of clause 27 wherein the suitably activated FLUOROPHORE is

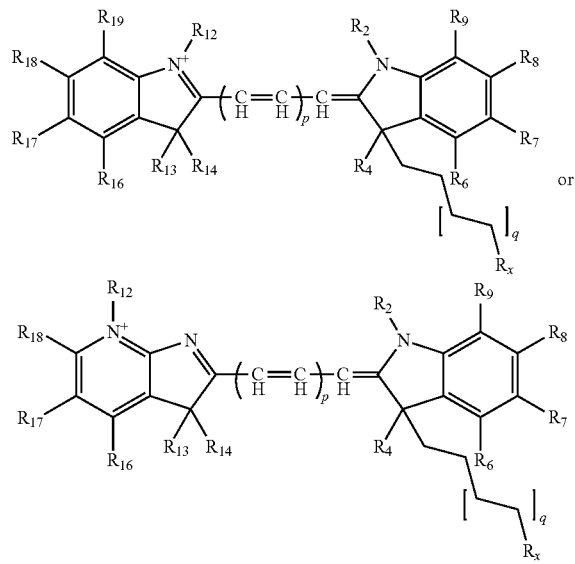

wherein

R$_4$ is C$_1$-C$_{22}$ alkyl or C$_7$-C$_{22}$ arylalkyl, each alkyl portion of which optionally incorporates up to six hetero atoms, selected from the group consisting of N, O and S, and each alkyl portion of which is optionally substituted one or more times by substituents selected from the group consisting of F, Cl, Br, I, hydroxy, carboxy, sulfo, phosphate, amino, sulfate, phosphonate, cyano, nitro, azido, C$_1$-C$_6$ alkoxy, C$_1$-C$_6$ alkylamino, or C$_2$-C$_{12}$ dialkylamino, or C$_3$-C$_{18}$ trialkylammonium;

R$_2$ is C$_1$-C$_{22}$ alkyl or C$_7$-C$_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, C$_1$-C$_6$ alkoxy, C$_1$-C$_6$ alkylamino, C$_2$-C$_{12}$ dialkylamino, or C$_3$-C$_{18}$ trialkylammonium;

R$_6$ is H, amino, sulfo, trifluoromethyl, halogen, C$_1$-C$_6$ alkyl, C$_1$-C$_6$ alkoxy, C$_1$-C$_6$ alkylamino, or C$_2$-C$_{12}$ dialkylamino, each alkyl portion of which is optionally further substituted by substituents selected from the group consisting of carboxy, sulfo, amino, and hydroxyl;

R$_7$ is H, amino, sulfo, trifluoromethyl, halogen, C$_1$-C$_6$ alkyl, C$_1$-C$_6$ alkoxy, C$_1$-C$_6$ alkylamino, or C$_2$-C$_{12}$ dialkylamino, each alkyl portion of which is optionally further substituted by substituents selected from the group consisting of carboxy, sulfo, amino, and hydroxyl;

R$_8$ is H, amino, sulfo, trifluoromethyl, halogen, C$_1$-C$_6$ alkyl, C$_1$-C$_6$ alkoxy, C$_1$-C$_6$ alkylamino, or C$_2$-C$_{12}$ dialkylamino, each alkyl portion of which is optionally further substituted by substituents selected from the group consisting of carboxy, sulfo, amino, and hydroxyl;

R$_9$ is H, amino, sulfo, trifluoromethyl, halogen, C$_1$-C$_6$ alkyl, C$_1$-C$_6$ alkoxy, C$_1$-C$_6$ alkylamino, or C$_2$-C$_{12}$ dialkylamino, each alkyl portion of which is optionally further substituted by substituents selected from the group consisting of carboxy, sulfo, amino, and hydroxyl;

R$_{16}$ is H, amino, sulfo, trifluoromethyl, halogen, C$_1$-C$_6$ alkyl, C$_1$-C$_6$ alkoxy, C$_1$-C$_6$ alkylamino, or C$_2$-C$_{12}$ dialkylamino, each alkyl portion of which is optionally further substituted by substituents selected from the group consisting of carboxy, sulfo, amino, and hydroxyl;

R$_{17}$ is H, amino, sulfo, trifluoromethyl, halogen, C$_1$-C$_6$ alkyl, C$_1$-C$_6$ alkoxy, C$_1$-C$_6$ alkylamino, or C$_2$-C$_{12}$ dialkylamino, each alkyl portion of which is optionally further substituted by substituents selected from the group consisting of carboxy, sulfo, amino, and hydroxyl;

R$_{18}$ is H, amino, sulfo, trifluoromethyl, halogen, C$_1$-C$_6$ alkyl, C$_1$-C$_6$ alkoxy, C$_1$-C$_6$ alkylamino, or C$_2$-C$_{12}$ dialkylamino, each alkyl portion of which is optionally further substituted by substituents selected from the group consisting of carboxy, sulfo, amino, and hydroxyl;

R$_{19}$ is H, amino, sulfo, trifluoromethyl, halogen, C$_1$-C$_6$ alkyl, C$_1$-C$_6$ alkoxy, C$_1$-C$_6$ alkylamino, or C$_2$-C$_{12}$ dialkylamino, each alkyl portion of which is optionally further substituted by substituents selected from the group consisting of carboxy, sulfo, amino, and hydroxyl;

or a member independently selected from

R$_6$ in combination with R$_7$;
R$_7$ in combination with R$_8$;
R$_8$ in combination with R$_9$;
R$_{16}$ in combination with R$_{17}$;
R$_{17}$ in combination with R$_{18}$; and
R$_{18}$ in combination with R$_{19}$ together with the atoms to which they are joined, form an aromatic ring comprising —CH— or —CR—$^1$ wherein R$^1$ is amino, sulfo, trifluoromethyl, halogen, C$_1$-C$_6$ alkyl, C$_1$-C$_6$ alkoxy, C$_1$-C$_6$ alkylamino, or C$_2$-C$_{12}$ dialkylamino, wherein each alkyl portion of which is optionally substituted by substituents selected from the group consisting of carboxy, sulfo, amino, and hydroxyl;

p is 1, 2 or 3;

q is 0, 1, 2 or 3;

R$_{12}$ is C$_1$-C$_{22}$ alkyl or C$_7$-C$_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, C$_1$-C$_6$ alkoxy, C$_1$-C$_6$ alkylamino, C$_2$-C$_{12}$ dialkylamino, or C$_3$-C$_{18}$ trialkylammonium;

R$_{13}$ is C$_1$-C$_{22}$ alkyl or C$_7$-C$_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, C$_1$-C$_6$ alkoxy, C$_1$-C$_6$ alkylamino, or C$_2$-C$_{12}$ dialkylamino, or C$_3$-C$_{18}$ trialkylammonium;

R$_{14}$ is C$_1$-C$_{22}$ alkyl or C$_7$-C$_{22}$ arylalkyl, each alkyl portion of which optionally incorporates up to six hetero atoms, selected from N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium;

or $R_{13}$ and $R_{14}$ taken in combination complete a five- or six-membered saturated or unsaturated ring that is optionally substituted;

sulfo is sulfonic acid or sulfonate; and $R_x$ is a reactive group selected from the group consisting of an activated ester of a carboxylic acid, an acyl azide, an aldehyde, an alkyl halide, an anhydride, a sulfonyl halide, a malemide, an isocyanate, and an isothiocyanate.

37. The process of clause 36 wherein the reactive group, Rx, is an activated ester of a carboxylic acid.

38. The process of clause 37 wherein the activated ester is a succinimidyl ester.

39. The process of clause 27 wherein the suitably activated FLUOROPHORE is

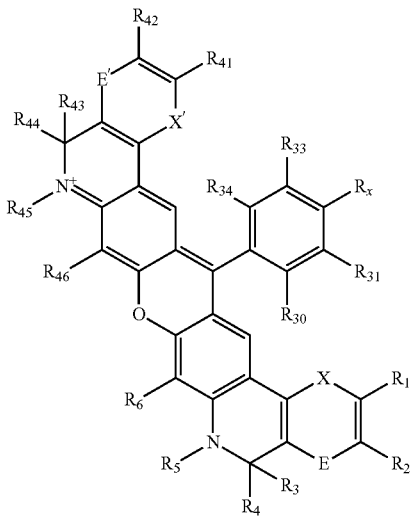

wherein:

$R_1$, $R_2$, $R_6$, $R_{41}$, $R_{42}$, and $R_{46}$ are independently selected from the group consisting of hydrogen, cyano, halogen, carboxylic acid, sulfonic acid $C_1$-$C_6$ alkyl, $C_1$-$C_6$ alkoxy, aryl, heteroaryl, wherein said alkyl or alkoxy is optionally substituted by carboxylic acid, sulfonic acid, or halogen and said aryl or heteroaryl is optionally substituted one or more times by $C_1$-$C_6$ alkyl, $C_1$-$C_6$ perfluoroalkyl, cyano, halogen, azido, carboxylic acid, sulfonic acid, or halomethyl;

or $R_1$ in combination with $R_2$, or $R_{41}$ in combination with $R_{42}$, or both, forms a fused aromatic or heteroaromatic ring that is optionally sulfonated one or more times;

$R_3$, $R_4$, $R_{43}$, and $R_{44}$ are independently selected from the group consisting of hydrogen, $C_1$-$C_6$ alkyl, an aromatic or heteroaromatic ring, wherein said alkyl is optionally substituted by carboxylic acid, sulfonic acid, amino, hydroxy, or halogen and said aromatic or heteroaromatic ring that is optionally substituted one or more times by $C_1$-$C_6$ alkyl, $C_1$-$C_6$ alkoxy, $C_1$-$C_6$ perfluoroalkyl, cyano, halogen, carboxylic acid, sulfonic acid, or halomethyl;

or $R_2$ in combination with $R_3$, $R_{42}$ in combination with $R_{43}$, or $R_3$ in combination with $R_4$, or $R_{43}$ in combination with $R_{44}$, or any combination thereof, forms a 5- or 6-membered alicyclic ring;

$R_5$ and $R_{45}$ are independently selected from the group consisting of hydrogen, methyl, carboxymethyl, $C_2$-$C_6$ alkyl, or heteroaryl, wherein said alkyl is optionally substituted by carboxylic acid, sulfonic acid, amino, or halogen and said aryl or heteroaryl is optionally substituted one or more times by $C_1$-$C_6$ alkyl, $C_1$-$C_6$ perfluoroalkyl, cyano, halogen, carboxylic acid, sulfonic acid, or halomethyl;

or $R_4$ in combination with $R_5$, or $R_5$ in combination with $R_6$, or $R_{44}$ in combination with $R_{45}$, or $R_{45}$ in combination with $R_{46}$, or any combination thereof, forms a 5- or 6-membered alicyclic ring;

wherein E, E', X' and X is O, S, or $NR^8$ provided that E and X or E' and X' are not both present;

wherein $R^8$ is independently selected from the group consisting of hydrogen, methyl, carboxymethyl, $C_2$-$C_6$ alkyl, wherein said alkyl is optionally substituted by carboxylic acid, sulfonic acid, amino, or halogen;

$R_{30}$, $R_{31}$, $R_{33}$ and $R_{34}$ are independently selected from the group consisting of hydrogen, F, Cl, Br, I, sulfonic acid, carboxylic acid, CN, nitro, hydroxy, azido, amino, hydrazino, or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_7$-$C_{18}$ arylcarboxamido, wherein said alkyl or aryl portions of said $R_{30}$, $R_{31}$, $R_{33}$ and $R_{34}$ are optionally substituted one or more times by substituents selected from the group consisting of F, Cl, Br, I, hydroxy, carboxylic acid, a carboxylic acid ester of a $C_1$-$C_6$ alcohol, sulfonic acid, amino, $C_1$-$C_6$ alkylamino, $C_1$-$C_6$ dialkylamino and $C_2$-$C_6$ alkoxy; or a pair of adjacent $R_{30}$ and $R_{31}$ or $R_{33}$ and $R_{34}$ substituents when taken in combination, form a fused 6-membered aromatic ring that is optionally further substituted by carboxylic acid; and $R_x$ is a reactive group selected from the group consisting of an activated ester of a carboxylic acid, an acyl azide, an aldehyde, an alkyl halide, an anhydride, a sulfonyl halide, a malemide, an isocyanate, and an isothiocyanate.

40. The process of clause 39 wherein the reactive group, Rx, is an activated ester of a carboxylic acid.

41. The process of clause 40 wherein the activated ester is a succinimidyl ester.

42. The process of clause 27 wherein the suitably activated FLUOROPHORE is

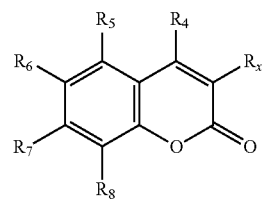

wherein $R_4$ is H, OH, CN, $C_1$-$C_{18}$ alkyl, $C_1$-$C_{18}$ perfluoroalkyl, sulfomethyl, biologically compatible salt of sulfomethyl, halomethyl, or aryl;

$R_5$ is H or $C_1$-$C_6$ alkoxy;

$R_6$ is H, methyl, halogen, or $SO_3X$;

$R_7$ is H or $NR^1R^2$; wherein $R_1$ and $R_2$ are independently H, $C_1$-$C_{18}$ alkyl, $C_6$-$C_{18}$ aryl, $C_1$-$C_{18}$ alkanoyl, $C_7$-$C_{18}$ arylalkanoyl;

or $R_1$ in combination with $R_2$ forms a saturated 5- or 6-membered heterocycle that is a piperidine, a morpholine, a pyrrolidine or a piperazine;

or R$_1$ is a 2-nitrobenzyloxycarbonyl of the formula

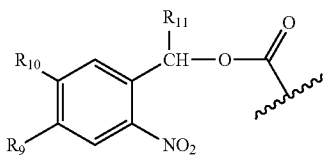

wherein

R$_9$ and R$_{10}$ are H, C$_1$-C$_6$ alkoxy, or R$_9$ and R$_{10}$ taken in combination are —O—CH$_2$—O—; and R$_{11}$ is H, CH$_3$, a carboxylic acid or a biologically compatible salt of a carboxylic acid;

R$_8$ is H, halogen, SO$_3$X, C$_1$-C$_6$ alkoxy or C$_1$-C$_6$ alkyl;

X is H, or a biologically compatible cation; and

R$_x$ is a reactive group selected from the group consisting of an activated ester of a carboxylic acid, an acyl azide, an aldehyde, an alkyl halide, an anhydride, a sulfonyl halide, a malemide, an isocyanate, and an isothiocyanate.

43. The process of clause 42 wherein the reactive group, Rx, is an activated ester of a carboxylic acid.

44. The process of clause 43 wherein the activated ester is a succinimidyl ester.

45. The compound, composition, method, kit or process of any one of the preceding clauses wherein Q is Ar$^1$, where Ar$^1$ is phenyl, 2-pyridyl, 3-pyridyl, or 4-pyridyl.

In reciting the foregoing collection of clauses, it is to be understood that all possible combinations of features, and all possible subgenera and sub-combinations are described.

It is to be understood that the embodiments described herein, including each of the foregoing, may be combined in all chemically relevant ways to generate subsets of the embodiments described herein. Accordingly, it is to be further understood that all such subsets are also illustrative embodiments of the invention described herein.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, and kits that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, and kits that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be understood that in certain embodiments, each of the forgoing may be univalent (i.e., attached to the remainder of the formula via one attachment) or multivalent (i.e., attached to the remainder of the formula via more than one attachment). It is to be further understood that in certain embodiments, alkyl is advantageously of limited length, including C$_1$-C$_{24}$, C$_1$-C$_{12}$, C$_1$-C$_8$, C$_1$-C$_6$, and C$_1$-C$_4$. It is to be further understood that in certain embodiments alkenyl and/or alkynyl may each be advantageously of limited length, including C$_2$-C$_{24}$, C$_2$-C$_{12}$, C$_2$-C$_8$, C$_2$-C$_6$, and C$_2$-C$_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain is cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. It is to be understood that in certain embodiments, each of the forgoing may be univalent (i.e., attached to the remainder of the formula via one attachment) or multivalent (i.e., attached to the remainder of the formula via more than one attachment). Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including C$_3$-C$_{24}$, C$_3$-C$_{12}$, C$_3$-C$_8$, C$_3$-C$_6$, and C$_5$-C$_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including C$_1$-C$_{24}$, C$_1$-C$_{12}$, C$_1$-C$_8$, C$_1$-C$_6$, and C$_1$-C$_4$, and C$_2$-C$_{24}$, C$_2$-C$_{12}$, C$_2$-C$_8$, C$_2$-C$_6$, and C$_2$-C$_4$, and the like. Illustratively, such particularly limited length alkylene groups, including C$_1$-C$_8$, C$_1$-C$_6$, and C$_1$-C$_4$, and C$_2$-C$_8$, C$_2$-C$_6$, and C$_2$-C$_4$, and the like may be referred to as lower alkylene. It is to be further understood that in certain embodiments alkenylene and/or alkynylene may each be advantageously of limited length, including C$_2$-C$_{24}$, C$_2$-C$_{12}$, C$_2$-C$_8$, C$_2$-C$_6$, and C$_2$-C$_4$, and C$_3$-C$_{24}$, C$_3$-C$_{12}$, C$_3$-C$_8$, C$_3$-C$_6$, and C$_3$-C$_4$, and the like. Illustratively, such particularly limited length alkenylene and/or alkynylene groups, including $C_2$-$C_8$, $C_2$-$C_6$, and $C_2$-$C_4$, and $C_3$-$C_8$, $C_3$-$C_6$, and $C_3$-$C_4$, and the like may be referred to as lower alkenylene and/or alkynylene. It is appreciated herein that shorter alkylene, alkenylene, and/or alkynylene groups may add less lipophilicity to the compound and accordingly will have different pharmacokinetic behavior. In embodiments of the invention described herein, it is to be understood, in each case, that the recitation of alkylene, alkenylene, and alkynylene refers to alkylene, alkenylene, and alkynylene as defined herein, and optionally lower alkylene, alkenylene, and alkynylene. Illustrative alkylene groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. It is to be understood that in certain embodiments, each of the forgoing may be univalent (i.e., attached to the remainder of the formula via one attachment) or multivalent (i.e., attached to the remainder of the formula via more than one attachment). In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e., alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

As used herein, the term "sulfinyl or a derivative thereof" includes $SO_2H$ and salts thereof, and esters and amides thereof.

As used herein, the term "sulfonyl or a derivative thereof" includes $SO_3H$ and salts thereof, and esters and amides thereof.

As used herein, the term "phosphinyl or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

As used herein, the term "phosphonyl or a derivative thereof" includes $PO_3H_2$ and salts thereof, and esters and amides thereof.

The term "optionally substituted" as used herein includes the replacement of hydrogen atoms with other functional groups on the radical that is optionally substituted. Such other functional groups illustratively include, but are not limited to, amino, hydroxyl, halo, thiol, azido, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, azido, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $-(CH_2)_x-Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, azido, and nitro; or $Z^X$ is selected from $-CO_2R^4$ and $-CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "effective amount" as used herein, refers to that amount of fluorescent-HAP stain (compound) described herein that elicits the desired response in a tissue system, cell, biological or binding assay, test, and the like being sought by a researcher, veterinarian, medical doctor or other clinician. In one aspect, the effective amount is that which may enable a diagnosis of HBV. In another aspect, the effective amount is that which may enable detection of HBV. In another aspect, the effective amount is that which may enable intra-cellular tracking of HBV. In another aspect, the effective amount is that which may enable measurement of competitive binding of anti-HBV drug candidates to the HAP pocket of HBV. It is to be understood that an effective amount of any one or a mixture of the compounds described herein can be readily determined by the researcher, veterinarian, medical doctor or other clinician by the use of known techniques and/or by observing results obtained under analogous circumstances.

As used herein, term "FL-HAP," "Fl-HAP," or "fluorescent-HAP" refers to a fluorescent heteroaryldihydropyrimidine-based stain (compound), which stains are detection reagents, diagnostic reagents, viral-tracking agents, and/or tools for drug discovery.

As used herein, the term "dye" refers to a compound that emits light to produce an observable detectable signal.

As used herein, the term "fluorophore" or "fluorogenic" refers to a compound, a composition, or a chemical entity that demonstrates that can re-emit light upon light excitation. It is understood that fluorophore or a fluorogenic compound, a composition, or a chemical entity can exhibit a change in fluorescence upon binding to a biological compound, target or analyte of interest and/or upon cleavage by an enzyme. It is understood that the fluorophores described herein may be substituted to alter the solubility, spectral properties or physical properties of the fluorophore.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from the isolated fluorescent-HAP compounds (stains) described herein or from salts, solutions, hydrates, solvates, and other forms of those compounds. It is also to be understood that the compositions may be prepared from various amorphous, non-amorphous, partially crystalline, crystalline, and/or other morphological forms of the compounds described herein. Accordingly, such compositions that recite compounds described herein are to be understood to include each of, or any combination of, the various morphological forms and/or solvate or hydrate forms of the those compounds. Illustratively, compositions may include one or more carriers, diluents, and/or excipients. The compounds described herein, or compositions containing them, may be formulated in a diagnostically effective amount in any conventional form appropriate for the methods described herein.

In another illustrative embodiment, compositions for use in HBV detection, HBV diagnosis, HBV-tracking, and/or anti-HBV drug discovery are described, which compositions include one or more of the fluorescent-HAP stains (compounds) of formulae (I), (Ia), (III), (IV), (V), (VI), (VII), (VIII), (IX), (X) and (XI) described herein in an amount effective for detecting, diagnosing, tracking, and/or competitively binding to HBV. It is to be understood that the compositions described herein may include other components and/or ingredients, including, but not limited to, other diagnostically active compounds and/or one or more carriers, diluents, excipients, and the like.

In another illustrative embodiment of the present invention, a method for detecting, diagnosing, and/or tracking HBV in cells and tissue is provided, the method being compatible for use in combination with, for example, currently-available antibody-based HBV detection and/or diagnostic methods, and including the steps of:

a) incubating a mixture of cells and one or more fluorescent-HAP stains (compounds) of formulae (I), (Ia), (III), (IV), (V), (VI), (VII), (VIII), (IX), (X) and (XI) described herein or a composition thereof in an amount effective for diagnosing, detecting, and/or tracking HBV;

b) washing away any excess of said one or more compounds;

c) providing a stimulus to the mixture to elicit a fluorescent signal; and d) analyzing the stimulated mixture.

In one illustrative aspect, a method for detecting, diagnosing, and/or tracking HBV in cells and tissue is described wherein the cells are from tissue culture. In another illustrative aspect, a method for detecting, diagnosing, and/or tracking HBV in cells and tissue is described wherein the cells are from a fresh biopsy. In another illustrative aspect, a method for detecting, diagnosing, and/or tracking HBV in cells and tissue is described wherein the cells are from a fixed section. In yet another illustrative aspect, a method for detecting, diagnosing, and/or tracking HBV in cells and tissue is described wherein the cells are from a source other than a tissue culture, a fresh biopsy, or a fixed section.

In another illustrative aspect, a method for detecting, diagnosing, and/or tracking HBV in cells and tissue is described wherein analyzing the stimulated mixture is accomplished by examining bulk fluorescence. In another illustrative aspect, a method for detecting, diagnosing, and/or tracking HBV in cells and tissue is described wherein analyzing the stimulated mixture is accomplished by examining individual cells by fluorescence microscopy. In another illustrative aspect, a method for detecting, diagnosing, and/or tracking HBV in cells and tissue is described wherein analyzing the stimulated mixture is accomplished by cell sorter. In yet another illustrative aspect, a method for detecting, diagnosing, and/or tracking HBV in cells and tissue is described wherein analyzing the stimulated mixture is accomplished by a mechanism other than examining bulk fluorescence, examining individual cells by fluorescence microscopy, or sorting cells in a cell sorter.

Another illustrative embodiment provides a method for detecting, diagnosing, and/or tracking HBV cores in solution, the method comprising the steps of:

a) incubating a solution comprising clarified serum, growth medium, or other liquid to be tested and one or more fluorescent-HAP stains (compounds) of formulae (I), (Ia), (III), (IV), (V), (VI), (VII), (VIII), (IX), (X) and (XI) described herein or a composition thereof in an amount effective for diagnosing, detecting, and/or tracking HBV;

b) adjusting ionic strength, if necessary, to induce e-antigen assembly for the purpose of detecting said assembly;

c) separating unbound said one or more compounds from said one or more compounds bound to HBV cores to create an unbound phase and a bound phase, respectively; and d) analyzing the fluorescence associated with the unbound and bound phases.

In one illustrative aspect, a method for detecting, diagnosing, and/or tracking HBV cores in solution is described wherein separating unbound compounds from compounds bound to HBV cores is accomplished by gel permeation chromatography. In another illustrative aspect, a method for detecting, diagnosing, and/or tracking HBV cores in solution is described wherein separating unbound compounds from compounds bound to HBV cores is accomplished by ultrafiltration. In another illustrative aspect, a method for detecting, diagnosing, and/or tracking HBV cores in solution is described wherein separating unbound compounds from compounds bound to HBV cores is accomplished by centrifugation. In yet another illustrative aspect, a method for detecting, diagnosing, and/or tracking HBV cores in solution is described wherein separating unbound compounds from compounds bound to HBV cores is accomplished by a technique other than gel permeation chromatography, ultrafiltration, or centrifugation Another illustrative embodiment provides a method for conducting anti-HBV drug discovery, the method including the steps of:

a) incubating a mixture of an anti-HBV drug candidate, pre-assembled HBV cores and one or more fluorescent-HAP stains (compounds) of formulae (I), (Ia), (III), (IV), (V), (VI), (VII), (VIII), (IX), (X) and (XI) described herein or a composition thereof in an amount effective for detecting competitive binding by the anti-HBV drug candidate to the HAP pocket of HBV;

b) measuring a change in the fluorescence of the one or more compounds; and c) analyzing the mixture for competitive binding by the anti-HBV drug candidate to the HAP pocket of HBV.

Another illustrative embodiment provides a method for conducting anti-HBV drug discovery, the method including the steps of:

a) incubating a mixture of an anti-HBV drug candidate, pre-assembled HBV cores and one or more fluorescent-HAP stains (compounds) of formulae (I), (Ia), (III), (IV), (V), (VI), (VII), (VIII), (IX), (X) and (XI) described herein or a composition thereof in an amount effective for detecting competitive binding by the anti-HBV drug candidate to the HAP pocket of HBV;

b) separating unbound said anti-HBV drug candidate and unbound said one or more compounds from said anti-HBV drug candidate and said one or more compounds bound to HBV cores to create an unbound phase and a bound phase, respectively;

c) measuring the fluorescence associated with the unbound and bound phases; and d) analyzing the mixture for competitive binding by the anti-HBV drug candidate to the HAP pocket of HBV.

In one illustrative aspect, a method for conducting anti-HBV drug discovery is described wherein separating unbound compounds from compounds bound to HBV cores is accomplished by gel permeation chromatography. In another illustrative aspect, a method for conducting anti-HBV drug discovery is described wherein separating unbound compounds from compounds bound to HBV cores is accomplished by ultrafiltration. In another illustrative aspect, a method for conducting anti-HBV drug discovery is described wherein separating unbound compounds from compounds bound to HBV cores is accomplished by centrifugation. In another illustrative aspect, a method for conducting anti-HBV drug discovery is described wherein separating unbound compounds from compounds bound to HBV cores is accomplished by a technique other than gel permeation chromatography, ultrafiltration, or centrifugation.

In another embodiment, the method of any one of the preceding embodiments wherein Q is $Ar^1$ is described.

Another illustrative embodiment provides a kit for detecting, diagnosing, and/or tracking HBV, as well identifying compounds that competitively bind to the HAP pocket of HBV, the kit being compatible for use in combination with, for example, currently-available antibody-based HBV detection and/or diagnostic reagents, and including:

a) a fluorescent-HAP stain of formula (I), (Ia), (III), (IV), (V), (VI), (VII), (VIII), (IX), (X) or (XI) described herein; and b) a suitable solvent.

In another embodiment, the kit of the preceding embodiment wherein Q is $Ar^1$ is described.

Another illustrative embodiment provides a process for preparing a fluorescent-HAP stain having the structural formula (I)

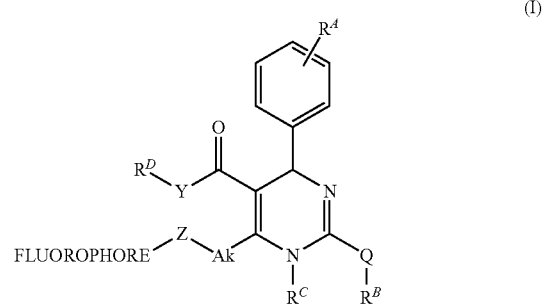

the process comprising:
(a) reacting a HAP compound of structural formula (II)

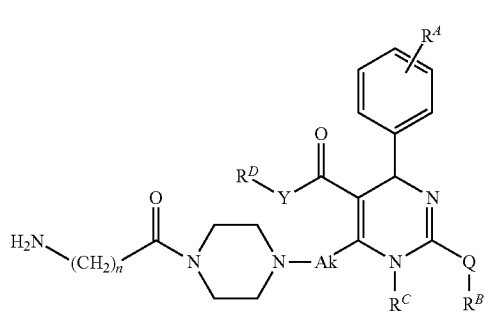

(II)

with a suitably activated FLUOROPHORE as shown generally in Scheme I, wherein Q, $R^C$, $R^D$, $Ar^1$, Z, Ak, $Ak_1$, $R^A$, $R^B$, n and FLUOROPHORE are as defined herein. Initial condensation of substituted benzaldehyde and acetoacetate derivatives affords β-aryl, α,β-unsaturated 1,3-dicarbonyl Compound a, which undergoes reaction with an amidino-heteroaryl compound to afford heteroaryldihydropyrimidine (HAP) b. Subsequent aminolysis with Boc-piperazine followed by TFA-mediated removal of the Boc protecting group yields piperazinyl-HAP c. (Similar series of transformations are contemplated for reacting a HAP compound of structural formulae (II') and (II'') with a suitably activated FLUOROPHORE.) Carbodiimide-mediated coupling of a desired Boc-protected amino acid followed by TFA-mediated removal of the Boc protecting group affords aminoacyl-piperazinyl-HAP d. Following conversion of d to the free amine, coupling of a suitably activated FLUOROPHORE produces fluorescent-HAP compounds e.

Scheme I

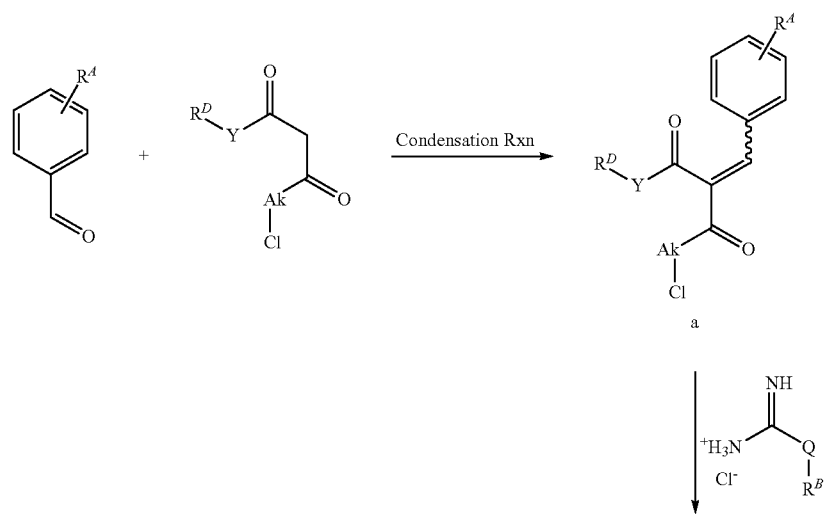

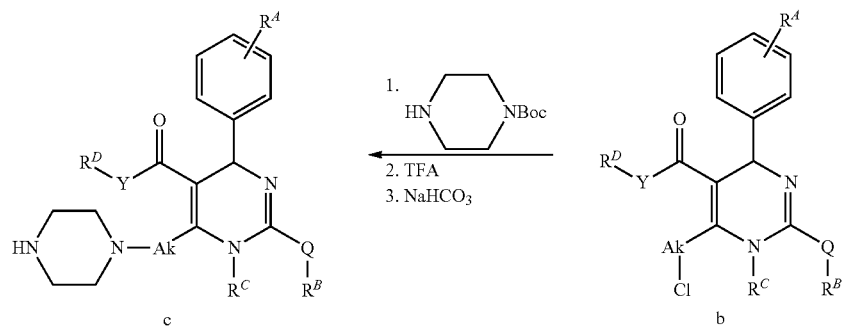

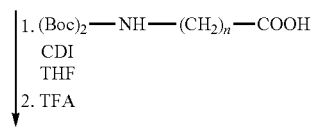

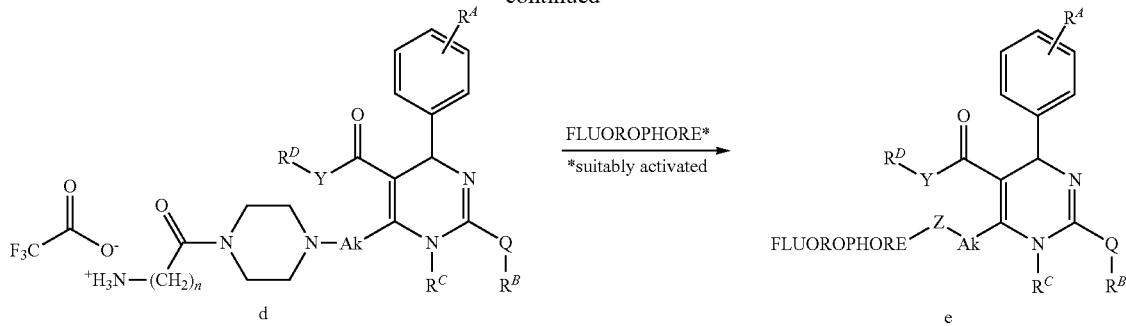

-continued d e

The following examples further illustrate specific embodiments of the invention; however, the following illustrative examples should not be interpreted in any way to limit the invention.

Synthesis of Fluorescent-HAP Stains for HBV

Three illustrative FLUOROPHORE-containing compounds were prepared that display specific binding to the capsid protein of HBV. Each compound has a different FLUOROPHORE: Compound 5 contains Alexa Fluor® 488 (from Invitrogen); Compound 6 contains fluorescein; and Compound 7 contains BODIPY® FL (from Invitrogen).

5

6

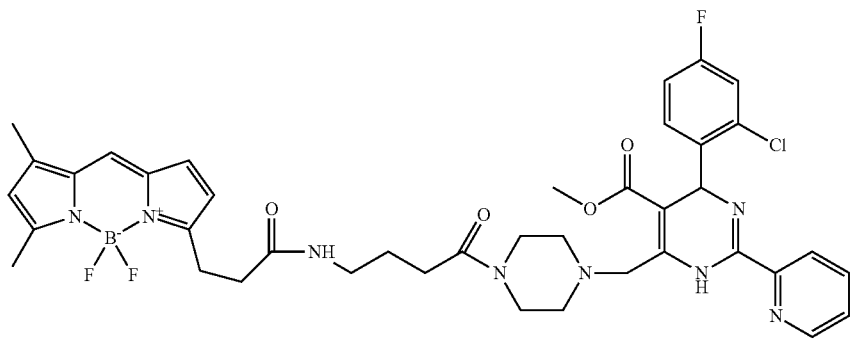
Representative Synthetic Route to Compound 5
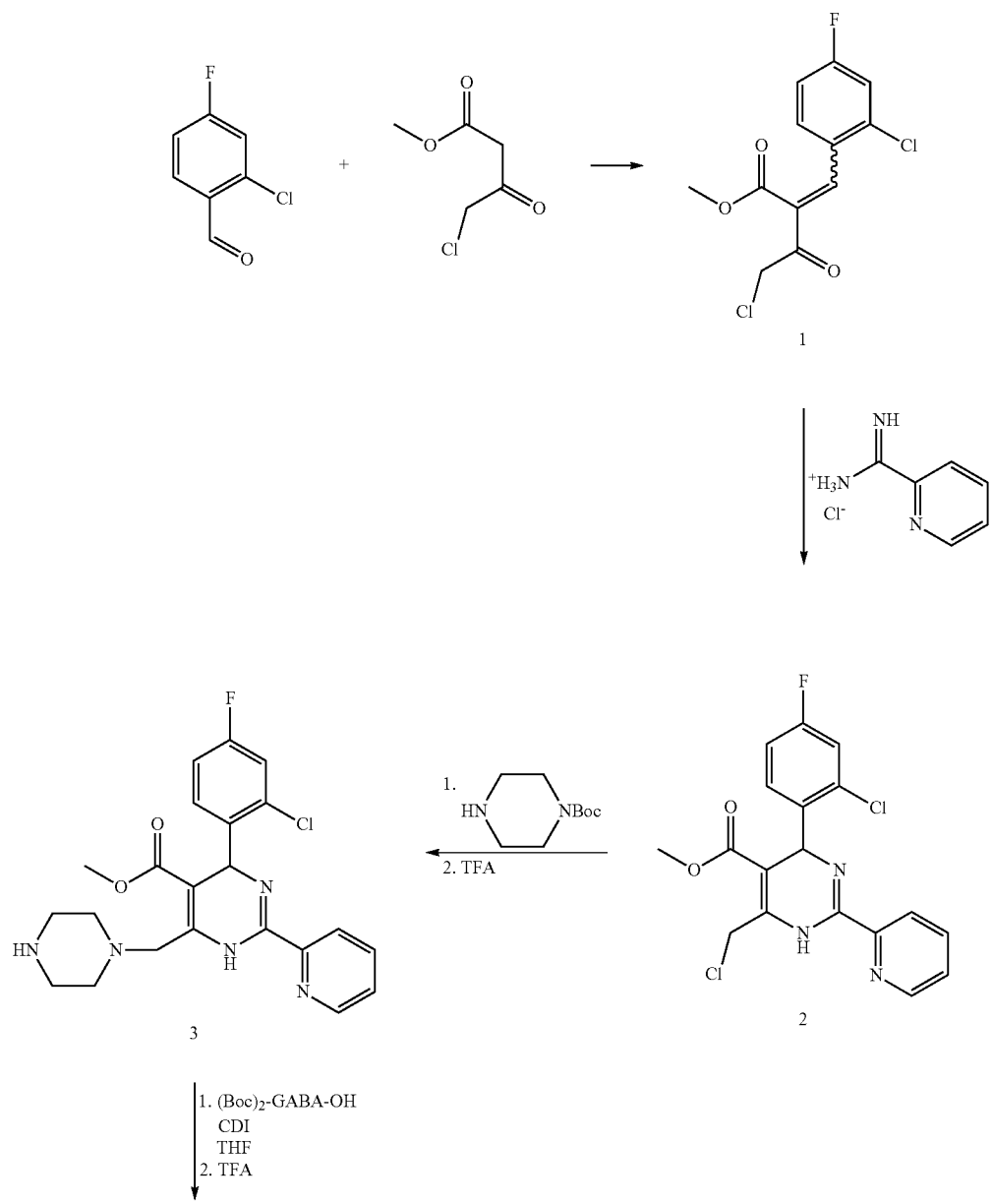

-continued
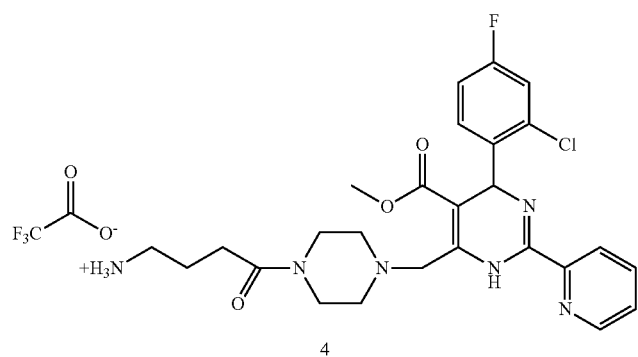
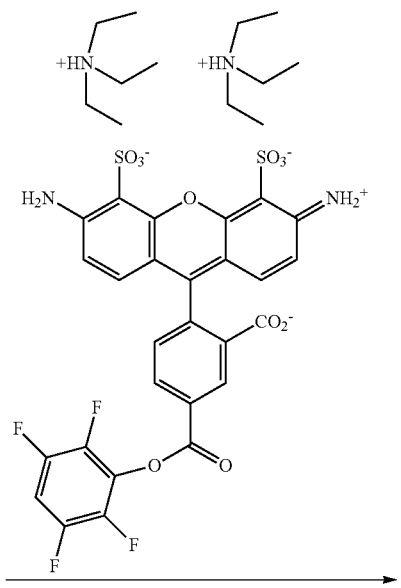
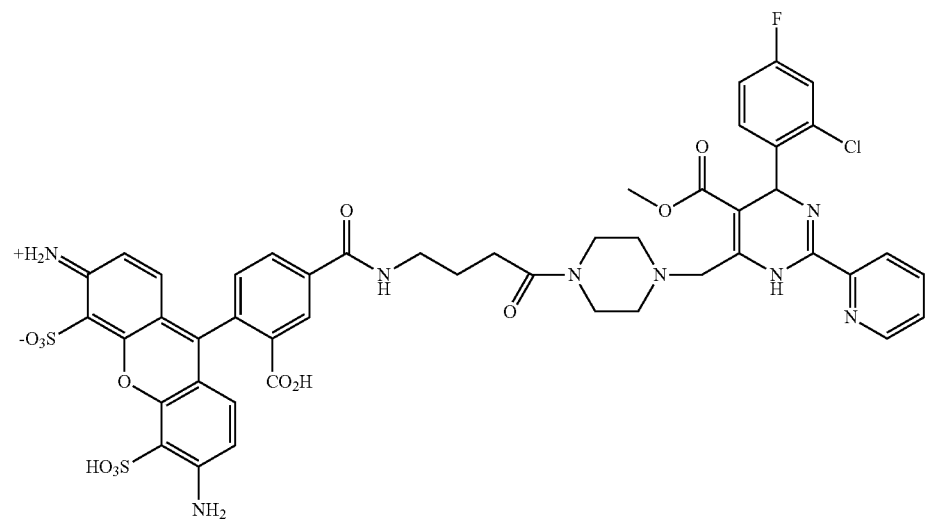

Synthesis of Compound 1:

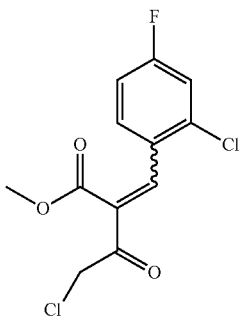

2-Chloro-4-fluorobenzaldehyde (3.2 g, 20.2 mmol) and methyl 4-chloroacetoacetate (2.31 mL, 20.0 mmol) were dissolved in 50 mL of toluene and refluxed for 4 hr using a Dean-Stark trap to remove the water. The solvent was removed in vacuo. The residual oil was dissolved in ether and washed with water. The organic layer was dried over anhydrous magnesium sulfate and reduced in vacuo to give 5.2 g of crude product. This material was purified by flash chromatography (10% ethyl acetate/hexane) to give 2.05 g (35% yield) of Compound 1 (an isomer mix) as an oil.

Synthesis of Compound 2:

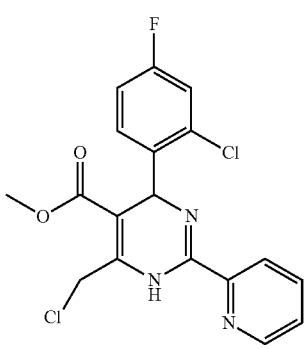

Compound 1 (2.0 g, 6.87 mmol), 2-amidinopyridine hydrochloride (1.08 g, 6.87 mmol), and sodium acetate (68 mg, 0.82 mmol, 0.12 eq) were dissolved in isopropanol (15 mL) and the solution was refluxed for 18 hr. The solvent was removed in vacuo and the residual solid was dissolved in ether and 1N HCl solution. The ether layer was washed with additional HCl solution. The combined acidic water layers were made basic with sodium bicarbonate. This aqueous layer was extracted with ether (3×). The combined organic layers were dried over anhydrous magnesium sulfate and reduced in vacuo to give 1.07 g of a crude product oil. The product was purified over a flash column (20% ethyl acetate/hexane) to give 402 mg (15% yield) of Compound 2 as a yellow oil. A portion of the oil was crystallized from ether/pentane to give 223 mg of Compound 2 as a yellow crystalline solid. mp 164-166° C. ESI mass spectrum 394.0 (M+H)+

Synthesis of Compound 3:

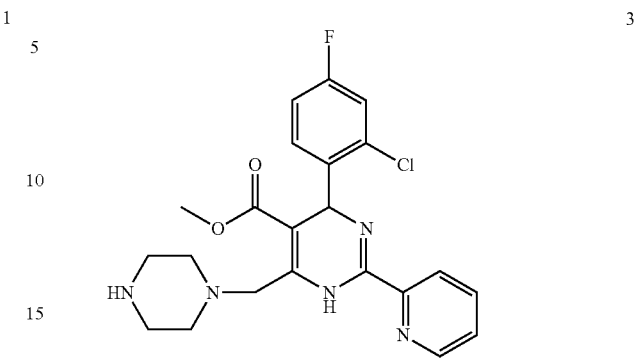

Compound 2 (55.2 mg, 0.140 mmol, 1 eq), t-butyl piperazine-1-carboxylate (130 mg, 0.7 mmol, 5 eq) and diisopropylethylamine (24.4 μL, 0.140 mmol, 1 eq) were dissolved in anhydrous DMF (2 mL). After 18 hr the solvent was removed in vacuo and the crude product was purified by flash chromatography (50% ethyl acetate/hexane). The pure fraction was reduced in vacuo to give Boc-protected 3 (69.9 mg, 92% yield) as a foam. The Boc protecting group was removed by dissolving the foam in 50% trifluoroacetic acid/DCM for 0.5 hr. The solvent was removed in vacuo and the residue was dissolved in DCM and washed with sat. sodium bicarbonate solution. The organic layer was dried over anhydrous magnesium sulfate and reduced in vacuo to give Compound 3 (50.4 mg, 88% yield) as a pale yellow oil.

Synthesis of Compound 4:

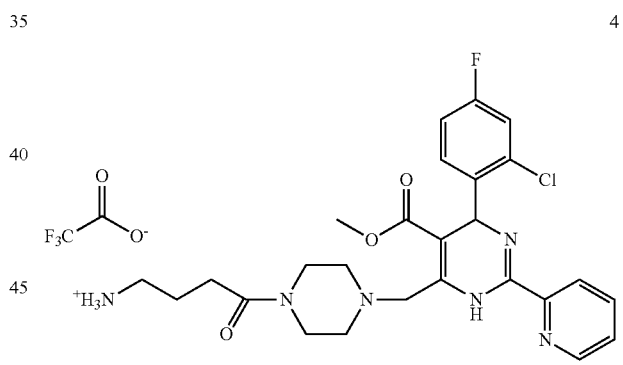

Di-Boc-GABA-OH (44.7 mg, 0.147 mmol, 1.3 eq) was dissolved in anhydrous THF (2 mL) in a dry flask. CDI (23.9 mg, 0.147 mmol, 1.3 eq) was added and the mixture was stirred for 2 hr followed by the addition of Compound 3 (50.3 mg, 0.113 mmol, 1.0 eq). After 18 hr the solution was reduced in vacuo and the crude product was solubilized in 50% acetonitrile/water. The solution analyzed by HPLC (mobile phase 30-90% ACN/water over 10 min, 0.1% TFA, 1 mL/min, with detection at 217 nm and by Evaporative Light Spray Detection (ELSD). A major product (di-Boc-protected 4) was seen with a retention time of 9.55 min. The product was purified by preparative HPLC (50-90% ACN over 10 min, 0.1% TFA, 217 nm). The pure fraction was reduced in vacuo to give 100.7 mg of a yellow oil. This oil was dissolved in 50% TFA/DCM (2 mL) for 1 hr. HPLC showed complete conversion to a new product peak at 4.94 min. The solvent was reduced in vacuo to give an oil which was redissolved in DCM with a small amount of methanol to help solubilize. Solvent was again removed to help remove residual TFA. The product was put under high vacuum for 18 hr to give 112 mg of the TFA salt of Compound 4 as a yellow oil. Accurate ESI MS. Found 529.2108. Calculated 529.2130 for $C_{26}H_{31}N_6O_3FCl$ $(M+H)^+$.

Synthesis of Compound 5:

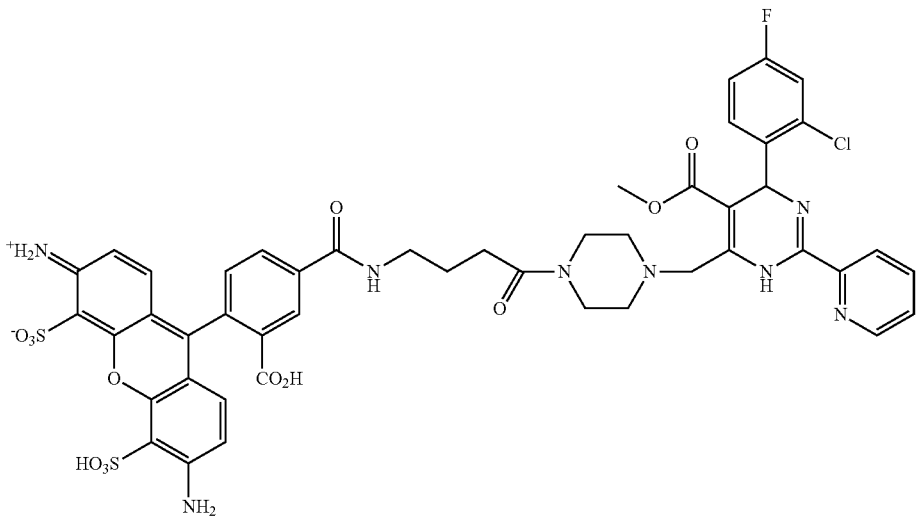

Compound 4 (1.7 mg, 2.25 μmol, 2 eq) was dissolved in anhydrous DMF (0.5 mL). DIPEA (1 μL) was added and the resulting solution was added to a vial of Alexa Fluor® 488 TFP ester (Invitrogen) (1.0 mg, 1.13 μmol, 1 eq). After 18 hr the solvent was removed in vacuo, the residue dissolved in 50% ACN/water and the solution was analyzed by HPLC (mobile phase 30-90% ACN/water over 10 min, buffer 0.1% TFA, 1 mL/min, with detection at 217 and 495 nm and by Evaporative Light Spray Detection (ELSD)). A product peak which absorbed at 495 nm was seen at 4.94 min. This peak was collected by preparative HPLC and reduced in vacuo to give Compound 5 as a solid which was dried under vacuum overnight. The mass was calculated to be 0.7 mg (61% yield) base on it's UV absorbance extinction coefficient. ESI mass spectrum 1045.2 $(M+H)^+$ Preparation of Compound 6:

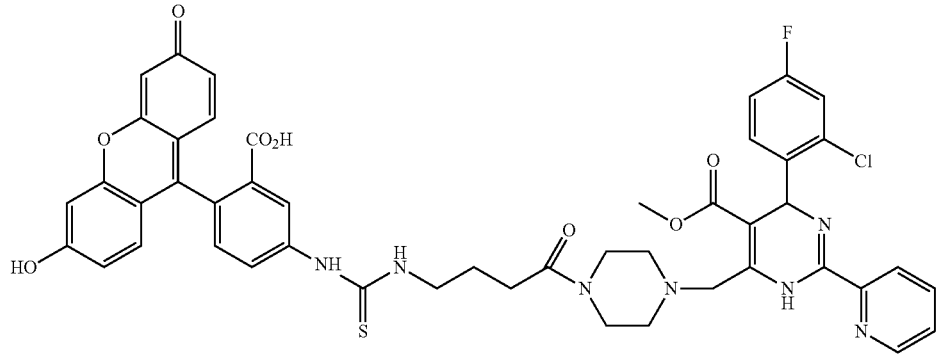

Using the representative route as previously described, Compound 4 (5 mg, 7.78 μmol) was reacted with fluorescein-5-isothiocyanate (FITC 'isomer 1') (5.4 mg, 14 μmol) to give Compound 6 (3.2 mg, 45% yield). Accurate ESI MS. Found 918.2460. Calculated 918.2488 for $C_{47}H_{42}N_7O_8SClF$ $(M+H)^+$.

Preparation of Compound 7:

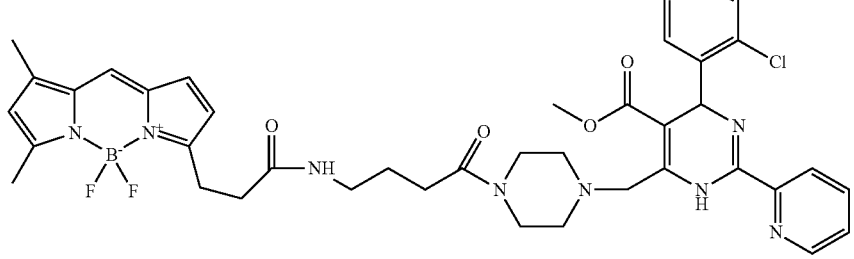

7

Using the representative route as previously described, Compound 4 (5 mg, 7.78 μmol) was reacted with BODIPY® FL succinimidyl ester (Invitrogen) (5.0 mg, 13 μmol) to give Compound 7 (1.5 mg, 24% yield). Accurate ESI MS. Found 803.3197. Calculated 803.3219 for $C_{40}H_{44}N_8O_4BSClF_3$ $(M+H)^+$.

Additional FLUOROPHORES, already suitably activated or amenable to suitable activation, for use in preparation of fluorescent-HAP stains by the methods described herein include, but are not limited to, FLUOROPHORES commercially available from Invitrogen (a division of Life Technologies Corporation) as 7-amino-4-methylcoumarin, Alexa Fluor® 350, Alexa Fluor® 405, Cascade Blue®, Cascade Yellow™, Dansyl, Dimethylaminocoumarin, Marina Blue®, Pacific Blue™, Pacific Orange™, Methoxycoumarin, Hydroxycoumarin, Alexa Fluor® 610-R-phycoerythrin, Alexa Fluor® 647-R-phycoerythrin, Alexa Fluor® 680-R-phycoerythrin, Cy2, Cy3, Cy3.5, Cy5, Cy5.5, Eosin, Oregon Green® 488, Rhodamine Green™, Rhodamine 6G, R-phycoerythrin, Alexa Fluor® 546, Alexa Fluor® 555, Alexa Fluor® 568, Alexa Fluor® 594, BODIPY® R6G, BODIPY® TMR, BODIPY® TR-X, Rhodamine 6G, Rhodamine Red™, Tetramethylrhodamine, Texas Red®, X-rhodamine, Alexa Fluor® 647, Alexa Fluor® 660, Alexa Fluor® 680, Alexa Fluor® 680-allophycocyanin, Alexa Fluor® 700, Alexa Fluor® 700-allophycocyanin, Alexa Fluor® 750, Alexa Fluor® 750-allophycocyanin, Alexa Fluor® 790, and Allophycocyanin.

Biological Testing of Fluorescent-HAP Stains for HBV

FIG. 1 shows that FL-HAP enhances assembly rate. In this experiment, 5 μM Cp was incubated with or without FL-HAP$_{AlexaFluor® 488}$ (Compound 5) prior to inducing assembly by addition of 150 mM NaCl. Increasing the concentration of FL-HAP$_{AlexaFluor® 488}$ (Compound 5) accelerates core protein assembly.

Figure 2:
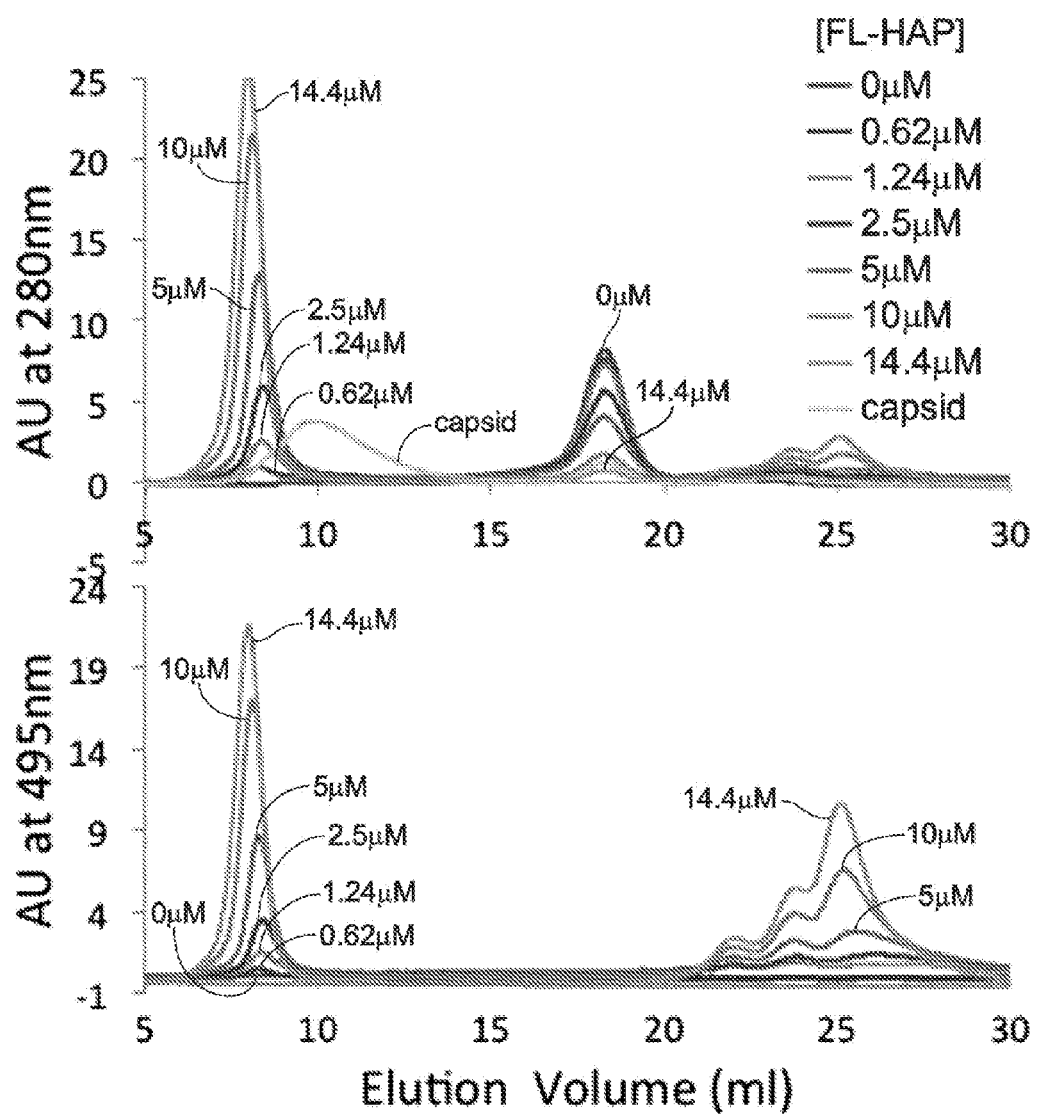
FIG. 2 shows that FL-HAP$_{AlexaFluor® 488}$ increases assembly stability and specifically binds HBV capsid, not dimer.

FIG. 2 shows that FL-HAP increases assembly stability and specifically binds capsid, not dimer. In this experiment, 5 μM Cp was mixed with FL-HAP$_{AlexaFluor® 488}$ (Compound 5) and then induced to assemble with 150 mM NaCl. Reactions were resolved on a Superose 6 column after 24 hours. Capsid elutes at 9.5 ml, aggregates at 8 ml, and Cp dimer at 18 ml. Increasing FL-HAP$_{AlexaFluor® 488}$ (Compound 5) led to more assembly of progressively larger complexes. Visualized at 495 nm (lower), where only the fluorescent molecule absorbs light, it is evident that only assembled Cp (i.e., capsid) is bound by FL-HAP.

Figure 3:
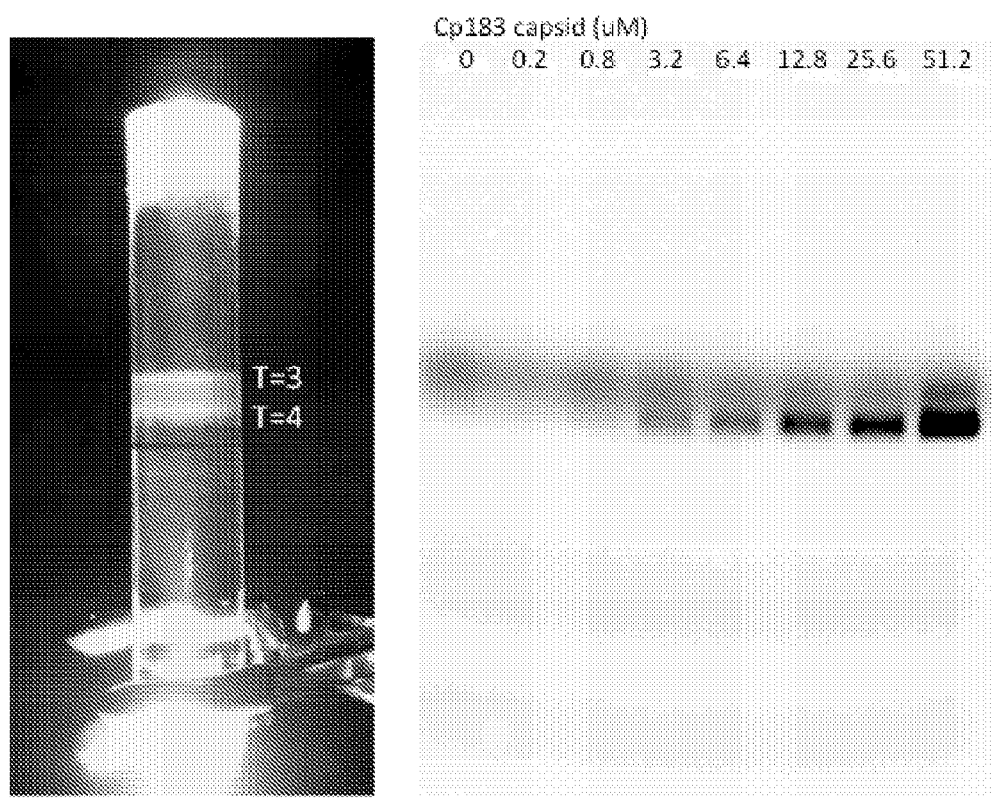
FIG. 3 shows that FL-HAP$_{Alexa Fluor® 488}$ binds HBV capsids with high affinity and dissociates slowly.

FIG. 3 shows that FL-HAP binds HBV capsids with high affinity and dissociates slowly. Shown at left: Capsids stained with FL-HAP$_{AlexaFluor® 488}$ (Compound 5) were separated on a sucrose gradient. Capsids occur in two sizes, hence the two bright (green) bands. Shown at right: Capsids, at the listed concentration, were stained with 25 nM FL-HAP$_{AlexaFluor® 488}$ (Compound 5) prior to electrophoresis. Even under these non-equilibrium conditions, FL-HAP$_{AlexaFluor® 488}$ binding was evident at nM concentrations.

Figure 4:
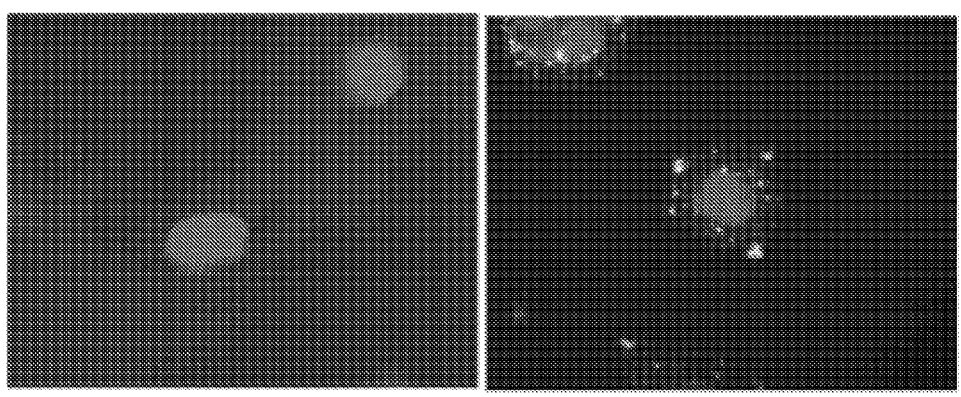
FIG. 4 shows that FL-HAP$_{Alexa Fluor® 488}$ only labels HBV-producing cells.

FIG. 4 shows that FL-HAP only labels HBV-producing cells. In the left panel, control HepG2 cells stained with FL-HAP$_{AlexaFluor® 488}$ (Compound 5) are shown in a fluorescence micrograph; the camera is set on high gain, nonetheless, no green puncta are seen. In HepG2 cells expressing RNA-filled HBV cores (right panel), numerous puncta and aggregates of puncta are seen after staining with FL-HAP$_{AlexaFluor® 488}$ (Compound 5).

FL-HAP$_{AlexaFluor® 488}$ (Compound 5) retains several critical properties of HAP molecules. It induces assembly of HBV core protein dimer (FIG. 1), enhances the extent of assembly (FIG. 2), and leads to formation of aberrant particles (FIG. 1 and FIG. 2). To demonstrate that FL-HAPs induce aberrant assembly, one can note that the amount of light scattering is in excess of free capsid (FIG. 1) and that assembly products run faster on a size exclusion column (SEC) than capsid (FIG. 2). In addition the SEC experiment shows that as FL-HAP$_{AlexaFluor® 488}$ is added there is progressively less free HBV dimer, indicating that FL-HAP stabilizes capsid. Most importantly, FL-HAP$_{AlexaFluor® 488}$ (Compound 5) binds pre-assembled cores with high affinity. This has been demonstrated by (i) size exclusion chromatography (FIG. 2) (ii) staining a sample of HBV cores and isolating them on a sucrose gradient (FIG. 3, left), and (iii) staining HBV cores that were subsequently electrophoretically purified on an agarose gel (FIG. 3, right). By examining the ratio of protein to fluorophore absorbance across the size exclusion chromatography peaks in FIG. 2, it was found that approximately 120 copies of FL-HAP$_{AlexaFluor® 488}$ (Compound 5) bind to an HBV capsid, i.e., one for every two core proteins. These data mechanistically demonstrate how HBV capsids are able to dramatically concentrate fluorescence. The data also show that FL-HAPs are a powerful tool for quantifying assembled HBV cores.

Various forms of FL-HAP may be synthesized thereby varying the resulting solubility properties of the fluorescent stain. The more soluble forms are particularly useful for observing HBV cores in solution or serum; they may also be useful for lightly staining intracellular HBV cores. The ability of the illustrative FL-HAP compound, FL-HAP$_{AlexaFluor® 488}$ (Compound 5), to cross cell membranes and label HBV-expressing cells and, specifically, to label concentrations of HBV cores in those cells, is shown in FIG. 4. Cells that do not express HBV do not concentrate FL-HAP$_{AlexaFluor® 488}$ (Compound 5) and show no labeling (FIG. 4). In other experiments (data not shown) FL-HAP$_{AlexaFluor® 488}$ (Compound 5) fluorescence has been observed to co-localize with Cp-specific antibodies. The more hydrophobic forms of FL-HAP (e.g., Compound 6 and Compound 7) are particularly useful for rapid staining of tissue samples.

The invention has now been described in such full, clear, concise and exact terms as to enable any person skilled in the art to which it pertains, to practice the same. It is to be understood that the foregoing describes preferred embodiments and examples of the invention and that modifications may be made therein without departing from the spirit or scope of the invention as set forth in the claims.

Each of the references cited herein, and all of the methods disclosed therein are incorporated by reference herein.

What is claimed is:

1. A compound having the formula (I)

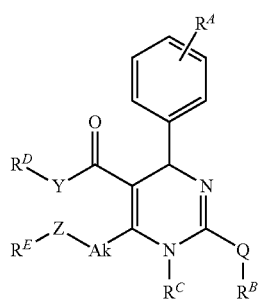

(I)

or a salt thereof, wherein:
Q is $Ar^1$ or $Ak_1$;
$Ar^1$ is aryl or heteroaryl
$R^C$ is hydrogen;
Ak and $Ak_1$ are independently $C_1$-$C_6$ alkylene;
Z is

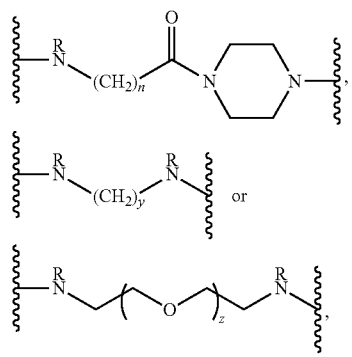

where n is 1, 2, 3, 4, 5, or 6; y is 6, 7, 8, 9, 10, 11 or 12; z is 1, 2, 3, or 4; and R is H or alkyl;

$R^D$ is selected from the group consisting of alkyl, heteroalkyl, alkenyl, and alkynyl, each of which is optionally substituted;
$R^E$ is a FLUOROPHORE;
Y is O, S, or HN;
$R^A$ represents from 0 to 3 substituents independently in each instance, halo or selected from the group consisting of alkyl, heteroalkyl, aryl, heteroaryl, amino and derivatives thereof, and hydroxyl and derivatives thereof, each of which is optionally substituted; and
$R^B$ represents from 0 to 3 substituents independently in each instance, halogen or selected from the group consisting of alkyl, heteroalkyl, aryl, heteroaryl, amino and derivatives thereof, and hydroxyl and derivatives thereof, each of which is optionally substituted.

2. The compound of claim 1 wherein $R^A$ represents 2-chloro-4-fluoro.

3. The compound of claim 1 wherein Q is $Ar^1$ where $Ar^1$ is 2-thiazolyl, 2-thienyl, 2-furanyl, 2-(1-methyl)imidazolyl, 2-pyrimidinyl, 2-naphthyl, 2-pyrrolidinyl, phenyl, 2-pyridyl, 3-pyridyl, or 4-pyridyl.

4. The compound of claim 1 wherein Q is $Ar^1$ where $Ar^1$ is 2-pyridyl.

5. The compound of claim 1 wherein Q is $Ar^1$ and $R^B$ is absent.

6. The compound of claim 1 wherein Y is O.

7. The compound of claim 1 wherein $R^D$ is methyl.

8. The compound of claim 1 wherein $R^E$ is

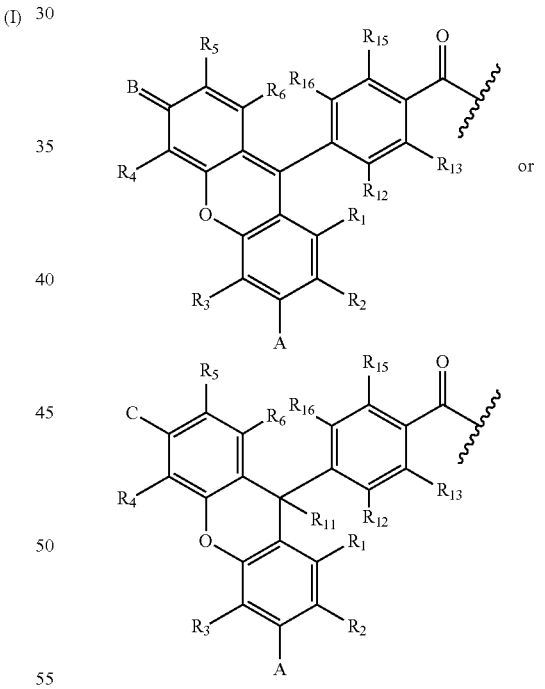

wherein
$R_2$, $R_3$, $R_4$ and $R_5$ are independently H, F, Cl, Br, I, CN; or $C_1$-$C_{18}$ alkyl, or $C_1$-$C_{18}$ alkoxy, where each alkyl or alkoxy is optionally further substituted by F, Cl, Br, I, a carboxylic acid, a salt of carboxylic acid, or a carboxylic acid ester of a $C_1$-$C_6$ alcohol; or —$SO_3X$ where X is H or a counterion;
$R_1$ and $R_6$ are H; or $R_1$ taken in combination with $R_2$ or $R_5$ taken in combination with $R_6$ or both, form a fused aromatic six-membered ring that is optionally substituted one or more times by —$SO_3X$;

A is $NR^8R^9$; where $R^8$ and $R^9$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl; or $R_8$ in combination with $R_9$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$-$C_6$ alkyl; or $R_8$ in combination with $R_2$, or $R_9$ in combination with $R_3$, or both, form a 5- or 6-membered ring that is saturated or unsaturated, and is optionally substituted by one or more $C_1$-$C_6$ alkyls or —$CH_2SO_3X$ moieties;

C is $OR_{17}$ or $NR^{18}R^{19}$, where $R_{17}$ is H, or $C_1$-$C_{18}$ alkyl;

$R^{18}$ and $R^{19}$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl; or $R_{18}$ in combination with $R_{19}$ forms a saturated 5- or 6-membered heterocycle that is a piperidine, a morpholine, a pyrrolidine or a piperazine, each of which is optionally substituted by methyl, carboxylic acid, a salt of carboxylic acid, or a carboxylic acid ester of a $C_1$-$C_6$ alkyl; or $R^{18}$ in combination with $R_4$, or $R^{19}$ in combination with $R_5$, or both, form a 5- or 6-membered ring that is saturated or unsaturated, and is optionally substituted by one or more $C_1$-$C_6$ alkyls or —$CH_2SO_3X$ moieties;

B is O or $N^+R^{18}R^{19}$, $R_{12}$, $R_{13}$, $R_{15}$, and $R_{16}$ are independently H, F, Cl, Br, I, —$SO_3X$, a carboxylic acid, a salt of carboxylic acid, CN, nitro, hydroxy, azido, amino, hydrazino; or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_6$-$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$-$C_6$ alcohol, —$SO_3X$, amino, alkylamino, dialkylamino or alkoxy, the alkyl portions of each having 1-6 carbons; or one pair of adjacent substituents $R_{12}$ and $R_{13}$ or $R_{15}$ and $R_{16}$, when taken in combination, form a fused 6-membered aromatic ring that is optionally further substituted by carboxylic acid, or a salt of carboxylic acid; and $R_{11}$ is H, hydroxy, CN or a $C_1$-$C_6$ alkoxy; or $R_{11}$ in combination with $R_{12}$ forms a 5- or 6-membered spirolactone ring or a 5- or 6-membered spirosultone ring that is optionally and independently substituted by H, F or $CH_3$.

9. The compound of claim 1 having the formula

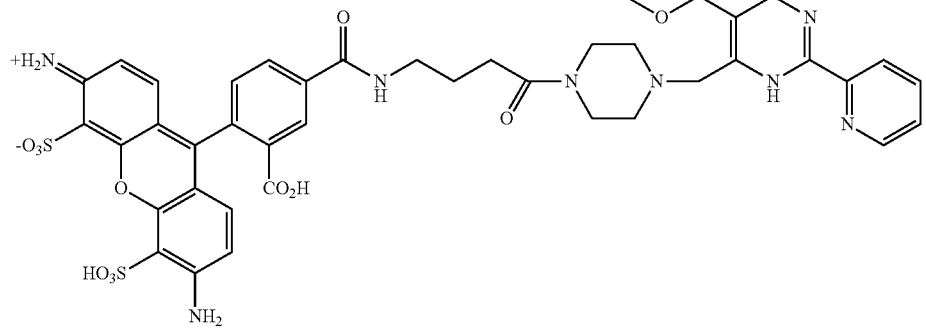

or a salt thereof.

10. The compound of claim 1 wherein $R^E$ is

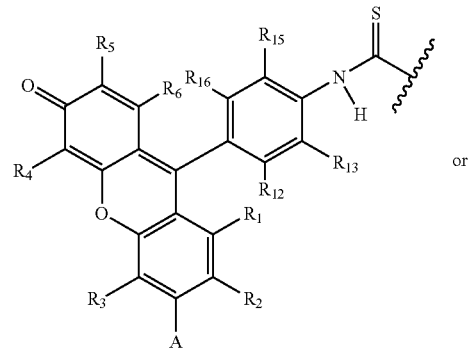

or

-continued

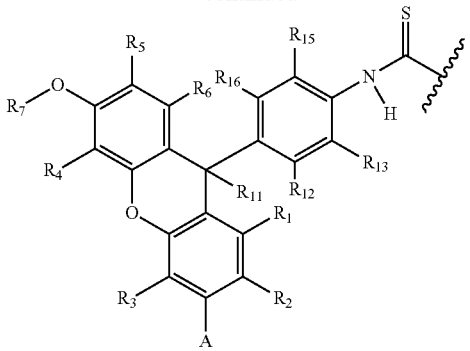

wherein $R_1$ and $R_6$ are independently H, F, Cl, Br, I, $C_1$-$C_{18}$ alkyl or $C_1$-$C_{18}$ alkoxy;

$R_2$, $R_3$, $R_4$ and $R_5$ are independently H, F, Cl, Br, I, CN; or $C_1$-$C_{18}$ alkyl, $C_1$-$C_{18}$ alkoxy or $C_1$-$C_{18}$ alkylthio, where each alkyl, alkoxy or alkylthio is optionally further substituted by F, Cl, Br, I, sulfonic acid, salt of sulfonic acid, carboxylic acid, a salt of carboxylic acid, a carboxylic acid ester of a $C_1$-$C_6$ alkyl, a carboxylic acid ester of —$CH_2$—O—(C═O)—$R_{18}$ where $R_{18}$ is a $C_1$-$C_4$ alkyl; or amino, alkylamino, dialkylamino, or alkoxy, the alkyl portions of which independently have 1-6 carbons; or one or both of $R_3$ and $R_4$ are —$CH_2$N($CH_2$COO$R_{17}$)$_2$, where $R_{17}$ is H, a biologically compatible counterion, a linear or branched alkyl having 1-6 carbons, or —$CH_2$—O—(C═O)—$R_{18}$;

A is O$R_7$ or N$R^8R^9$, where each $R_7$ is independently H, $C_1$-$C_{18}$ alkyl, a $C_1$-$C_{18}$ acyl wherein each alkyl group independently has 1-6 carbons and is optionally substituted by amino, hydroxy, carboxylic acid, a salt of carboxylic acid, a carboxylic acid ester of a $C_1$-$C_6$ alkyl, a carboxylic acid ester of —$CH_2$—O—(C═O)—$R_{18}$; or a trialkylsilyl wherein each alkyl group independently has 1-6 carbons;

$R^8$ and $R^9$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, a salt of $C_1$-$C_6$ sulfoalkyl, or $C_1$-$C_{18}$ acyl wherein the alkyl portions are optionally substituted by amino, hydroxy, carboxylic acid, a salt of carboxylic acid, a carboxylic acid ester of a $C_1$-$C_6$ alkyl, a carboxylic acid ester of —$CH_2$—O—(C═O)—$R_{18}$; or $R^8$ in combination with $R_2$, or $R^9$ in combination with $R_3$, or both, form a saturated 5- or 6-membered ring that is optionally substituted by one or more methyls; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$-$C_6$ alkyl, or a carboxylic acid ester of —$CH_2$—O—(C═O)—$R_{18}$;

$R_{12}$, $R_{13}$, $R_{15}$ and $R_{16}$ are independently H, F, Cl, Br, I; or sulfonic acid, salt of sulfonic acid, carboxylic acid, a salt of carboxylic acid, a carboxylic acid ester of a $C_1$-$C_6$ alkyl, a carboxylic acid ester of —$CH_2$—O—(C═O)—$R_{18}$, CN, nitro, hydroxy, azido, amino, hydrazino; or $C_1$-$C_{18}$ alkyl, $C_1$-$C_{18}$ alkoxy, $C_1$-$C_{18}$ alkylthio, $C_1$-$C_{18}$ alkylamino, $C_1$-$C_{18}$ alkylester, $C_1$-$C_{18}$ alkylamido or $C_1$-$C_{18}$ arylamido, the alkyl or aryl portions of which are optionally substituted one or more times by F, Cl, Br, I, hydroxy, carboxylic acid, a salt of carboxylic acid, a carboxylic acid ester of a $C_1$-$C_6$ alkyl, a carboxylic acid ester of —$CH_2$—O—(C═O)—$R_{18}$, sulfonic acid, salt of sulfonic acid, amino, alkylamino, dialkylamino or alkoxy, the alkyl portions of each having 1-6 carbons; or one pair of adjacent substituents $R_{12}$ and $R_{13}$ or $R_{15}$ and $R_{16}$, when taken in combination, form a fused 6-membered aromatic ring that is optionally further substituted by carboxylic acid, a salt of carboxylic acid, a carboxylic acid ester of a $C_1$-$C_6$ alkyl, a carboxylic acid ester of —$CH_2$—O—(C═O)—$R_{18}$; and $R_{11}$ is H, hydroxy, CN or a $C_1$-$C_6$ alkoxy; or $R_{11}$ in combination with $R_{12}$ forms a 5- or 6-membered spirolactone ring or a 5- or 6-membered spirosultone ring that is optionally and independently substituted by H, F or $CH_3$.

11. The compound of claim 1 having the formula

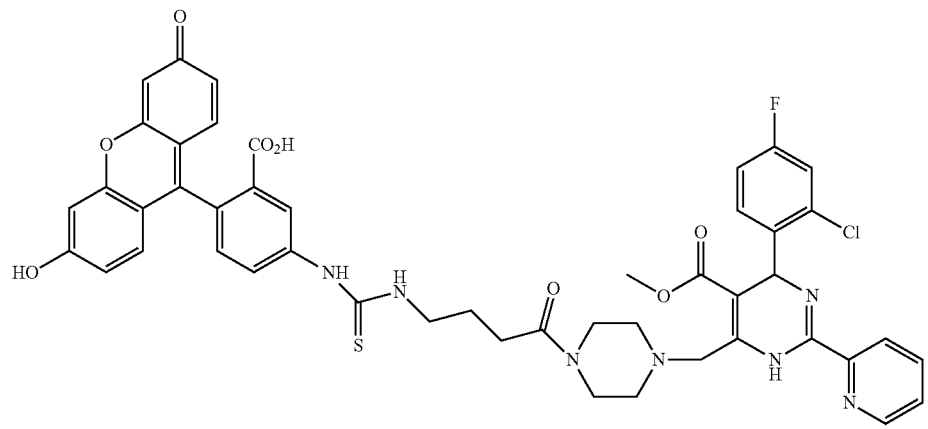 [SMILES: COC(=O)C1=C(CN2CCN(C(=O)CCCNC(=S)Nc3ccc(-c4c5ccc(=O)cc-5oc5cc(O)ccc45)c(C(=O)O)c3)CC2)NC(c2ccccn2)=NC1c1ccc(F)cc1Cl]

or a salt thereof.

12. The compound of claim 1 wherein $R^E$ is

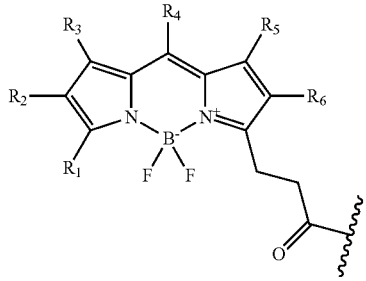

wherein $R_1$, $R_2$, $R_3$, $R_4$, $R_5$, and $R_6$ are each independently H, halogen, alkyl, cycloalkyl, aryl, arylalkyl, acyl or sulfo.

13. The compound of claim 1 having the formula

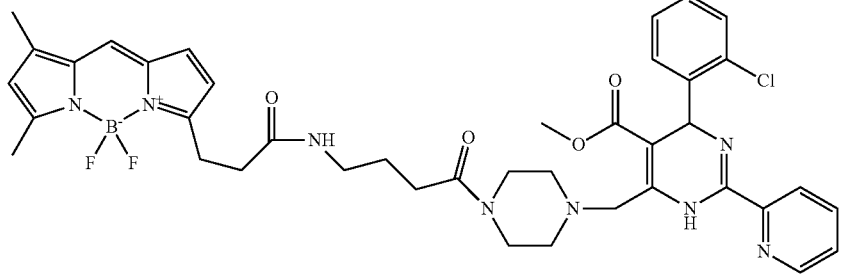

or a salt thereof.

14. The compound of claim 1 wherein $R^E$ is

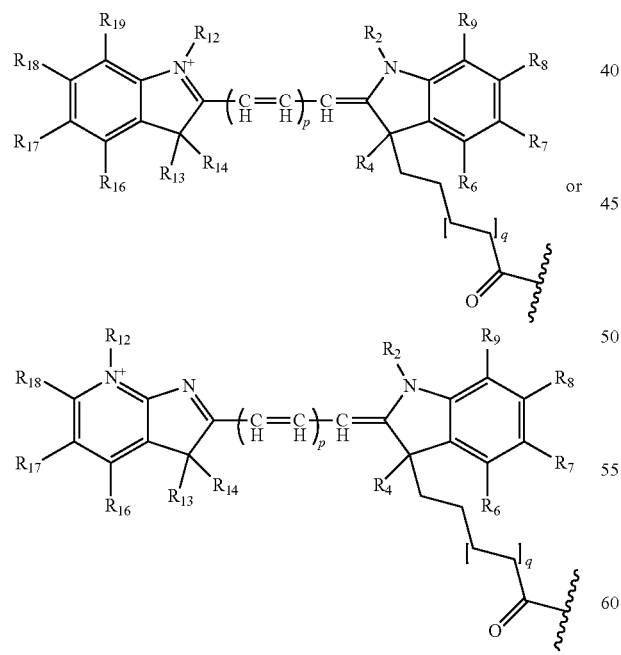

wherein $R_4$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by substituents selected from the group consisting of F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium;

$R_2$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, $C_2$-$C_{12}$ dialkylamino, or $C_3$-$C_{18}$ trialkylammonium;

$R_6$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_7$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_8$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_9$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{16}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{17}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{18}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

$R_{19}$ is H, amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, each alkyl portion of which is optionally further substituted by substituents selected from the group consisting of carboxy, sulfo, amino, and hydroxyl;

or a member independently selected from $R_6$ in combination with $R_7$;

$R_7$ in combination with $R_8$;

$R_8$ in combination with $R_9$;

$R_{16}$ in combination with $R_{17}$;

$R_{17}$ in combination with $R_{18}$; and $R_{18}$ in combination with $R_{19}$ together with the atoms to which they are joined, form an aromatic ring comprising —CH— or —CR$^1$— wherein R$^1$ is amino, sulfo, trifluoromethyl, halogen, $C_1$-$C_6$ alkyl, $C_1$-$C_6$ alkoxy, $C_1$-$C_6$ alkylamino, or $C_2$-$C_{12}$ dialkylamino, wherein each alkyl portion of which is optionally substituted by substituents selected from the group consisting of carboxy, sulfo, amino, and hydroxyl;

p is 1, 2 or 3;

q is 0, 1, 2 or 3;

$R_{12}$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, $C_2$-$C_{12}$ dialkylamino, or $C_3$-$C_{18}$ trialkylammonium;

$R_{13}$ is $C_1$-$C_{22}$ alkyl or $C_7$-$C_{22}$ arylalkyl, each alkyl portion of which optionally incorporates up to six hetero atoms, selected from the group consisting of N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium;

$R_{14}$ is $C_1$-$C_{22}$ alkyl or $C_7$-$C_{22}$ arylalkyl, each alkyl portion of which optionally incorporates up to six hetero atoms, selected from N, O and S, and each alkyl portion of which is optionally substituted one or more times by F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium;

or $R_{13}$ and $R_{14}$ taken in combination complete a five- or six-membered saturated or unsaturated ring that is optionally substituted; and wherein sulfo is sulfonic acid or sulfonate.

15. The compound of claim 1 wherein $R^E$ is

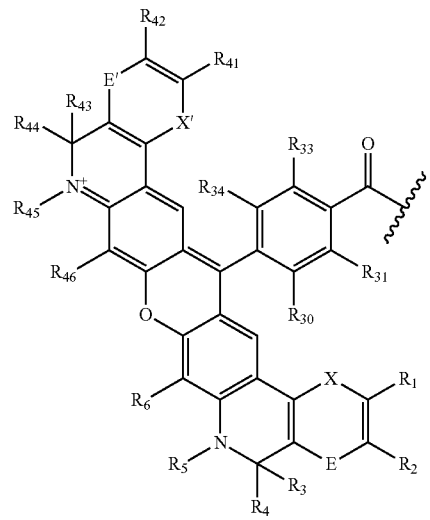

wherein $R_1$, $R_2$, $R_6$, $R_{41}$, $R_{42}$, and $R_{46}$ are independently selected from the group consisting of hydrogen, cyano, halogen, carboxylic acid, sulfonic acid $C_1$-$C_6$ alkyl, $C_1$-$C_6$ alkoxy, aryl, heteroaryl, wherein said alkyl or alkoxy is optionally substituted by carboxylic acid, sulfonic acid, or halogen and said aryl or heteroaryl is optionally substituted one or more times by $C_1$-$C_6$ alkyl, $C_1$-$C_6$ perfluoroalkyl, cyano, halogen, azido, carboxylic acid, sulfonic acid, or halomethyl;

or $R_1$ in combination with $R_2$, or $R_{41}$ in combination with $R_{42}$, or both, forms a fused aromatic or heteroaromatic ring that is optionally sulfonated one or more times;

$R_3$, $R_4$, $R_{43}$, and $R_{44}$ are independently selected from the group consisting of hydrogen, $C_1$-$C_6$ alkyl, an aromatic or heteroaromatic ring, wherein said alkyl is optionally substituted by carboxylic acid, sulfonic acid, amino, hydroxy, or halogen and said aromatic or heteroaromatic ring that is optionally substituted one or more times by $C_1$-$C_6$ alkyl, $C_1$-$C_6$ alkoxy, $C_1$-$C_6$ perfluoroalkyl, cyano, halogen, carboxylic acid, sulfonic acid, or halomethyl;

or $R_2$ in combination with $R_3$, $R_{42}$ in combination with $R_{43}$, or $R_3$ in combination with $R_4$, or $R_{43}$ in combination with $R_{44}$, or any combination thereof, forms a 5- or 6-membered alicyclic ring;

$R_5$ and $R_{45}$ are independently selected from the group consisting of hydrogen, methyl, carboxymethyl, $C_2$-$C_6$ alkyl, or heteroaryl, wherein said alkyl is optionally substituted by carboxylic acid, sulfonic acid, amino, or halogen and said aryl or heteroaryl is optionally substituted one or more times by $C_1$-$C_6$ alkyl, $C_1$-$C_6$ perfluoroalkyl, cyano, halogen, carboxylic acid, sulfonic acid, or halomethyl;

or $R_4$ in combination with $R_5$, or $R_5$ in combination with $R_6$, or $R_{44}$ in combination with $R_{45}$, or $R_{45}$ in combination with $R_{46}$, or any combination thereof, forms a 5- or 6-membered alicyclic ring;

wherein E, E', X' and X is O, S, or NR$^8$ provided that E and X or E' and X' are not both present;

wherein R$^8$ is independently selected from the group consisting of hydrogen, methyl, carboxymethyl, $C_2$-$C_6$ alkyl, wherein said alkyl is optionally substituted by carboxylic acid, sulfonic acid, amino, or halogen; and $R_{30}$, $R_{31}$, $R_{33}$ and $R_{34}$ are independently selected from the group consisting of hydrogen, F, Cl, Br, I, sulfonic acid, carboxylic acid, CN, nitro, hydroxy, azido, amino, hydrazino, or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_7$-$C_{18}$ arylcarboxamido, wherein said alkyl or aryl portions of said $R_{30}$, $R_{31}$, $R_{33}$ and $R_{34}$ are optionally substituted one or more times by substituents selected from the group consisting of F, Cl, Br, I, hydroxy, carboxylic acid, a carboxylic acid ester of a $C_1$-$C_6$ alcohol, sulfonic acid, amino, $C_1$-$C_6$ alkylamino, $C_1$-$C_6$ dialkylamino and $C_2$-$C_6$ alkoxy; or a pair of adjacent $R_{30}$ and $R_{31}$ or $R_{33}$ and $R_{34}$ substituents when taken in combination, form a fused 6-membered aromatic ring that is optionally further substituted by carboxylic acid.

16. The compound of claim 1 wherein $R^E$ is

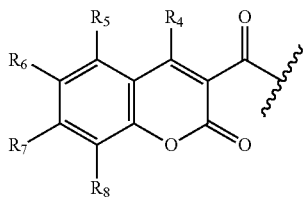

wherein
$R_4$ is H, OH, CN, $C_1$-$C_{18}$ alkyl, $C_1$-$C_{18}$ perfluoroalkyl, sulfomethyl, biologically compatible salt of sulfomethyl, halomethyl, or aryl;
$R_5$ is H or $C_1$-$C_6$ alkoxy;
$R_6$ is H, methyl, halogen, or $SO_3X$;
$R_7$ is H or $NR^1R^2$; wherein
$R_1$ and $R_2$ are independently H, $C_1$-$C_{18}$ alkyl, $C_6$-$C_{18}$ aryl, $C_1$-$C_{18}$ alkanoyl, $C_7$-$C_{18}$ arylalkanoyl;
or $R_1$ in combination with $R_2$ forms a saturated 5- or 6-membered heterocycle that is a piperidine, a morpholine, a pyrrolidine or a piperazine;
or $R_1$ is a 2-nitrobenzyloxycarbonyl of the formula

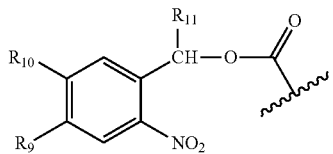

wherein
$R_9$ and $R_{10}$ are H, $C_1$-$C_6$ alkoxy, or $R_9$ and $R_{10}$ taken in combination are —O—$CH_2$—O—; and $R_{11}$ is H, $CH_3$, a carboxylic acid or a biologically compatible salt of a carboxylic acid;
$R_8$ is H, halogen, $SO_3X$, $C_1$-$C_6$ alkoxy or $C_1$-$C_6$ alkyl; and
X is H, or a biologically compatible cation.

17. A composition comprising one or more compounds of claim 1 in an amount effective for diagnosing, detecting, tracking, and/or competitively binding to HBV.

18. The composition of claim 16 further comprising one or more carriers, diluents, or excipients, or a combination thereof.

19. A method for detecting, diagnosing, and/or tracking HBV in cells and tissue, the method comprising the steps of:
a) incubating a mixture of cells and one or more compounds of claim 1 or a composition thereof in an amount effective for diagnosing, detecting, and/or tracking HBV;
b) washing away any excess of said one or more compounds;
c) providing a stimulus to the mixture to elicit a fluorescent signal; and
d) analyzing the stimulated mixture.

20. The method of claim 19, wherein the cells are from tissue culture, fresh biopsy, fixed section, or other source.

21. The method of claim 19, wherein analyzing is accomplished by examining bulk fluorescence, by examining individual cells by fluorescence microscopy, by cell sorter, or by another mechanism.

22. A method for detecting, diagnosing, and/or tracking HBV cores in solution, the method comprising the steps of:
a) incubating a solution comprising clarified serum, growth medium, or other liquid to be tested and one or more compounds of claim 1 or a composition thereof in an amount effective for diagnosing, detecting, and/or tracking HBV;
b) adjusting ionic strength, if necessary, to induce e-antigen assembly for the purpose of detecting said assembly;
c) separating unbound said one or more compounds from said one or more compounds bound to HBV cores to create an unbound phase and a bound phase, respectively; and
d) analyzing the fluorescence associated with the unbound and bound phases.

23. The method of claim 22, wherein separating unbound compounds from compounds bound to HBV cores is accomplished by gel permeation chromatography, ultrafiltration, centrifugation, or other technique.

24. A method for conducting anti-HBV drug discovery, the method comprising the steps of:
a) incubating a mixture of an anti-HBV drug candidate, pre-assembled HBV cores and one or more compounds of claim 1 or a composition thereof in an amount effective for detecting competitive binding by the anti-HBV drug candidate to the HAP pocket of HBV;
b) measuring a change in the fluorescence of said one or more compounds; and
c) analyzing the mixture for competitive binding by the anti-HBV drug candidate to the HAP pocket of HBV.

25. A method for conducting anti-HBV drug discovery, the method comprising the steps of:
a) incubating a mixture of an anti-HBV drug candidate, pre-assembled HBV cores and one or more compounds of claim 1 or a composition thereof in an amount effective for detecting competitive binding by the anti-HBV drug candidate to the HAP pocket of HBV;
b) separating unbound said anti-HBV drug candidate and unbound said one or more compounds from said anti-HBV drug candidate and said one or more compounds bound to HBV cores to create an unbound phase and a bound phase, respectively;
c) measuring the fluorescence associated with the unbound and bound phases; and
d) analyzing the mixture for competitive binding by the anti-HBV drug candidate to the HAP pocket of HBV.

26. The method of claim 25, wherein separating unbound compounds from compounds bound to HBV cores is accomplished by gel permeation chromatography, ultrafiltration, centrifugation, or other technique.

27. A kit for detecting, diagnosing, and/or tracking HBV, and/or identifying compounds that competitively bind to the HAP pocket of HBV, the kit comprising:
   a) one or more compounds of claim 1 or a composition thereof; and
   b) a solvent.

28. The compound of claim 1 wherein Q is $Ar^1$, where $Ar^1$ is pheny, 2-pyridyl, 3-pyridyl, or 4-pyridyl.

* * * * *